(12) United States Patent
Uehara

(10) Patent No.: US 10,292,647 B1
(45) Date of Patent: May 21, 2019

(54) SYSTEM AND METHOD FOR DEVELOPING CORE MUSCLE USAGE IN ATHLETICS AND THERAPY

(71) Applicant: Alert Core, Inc., Kailua, HI (US)

(72) Inventor: Gregory Takeo Uehara, Kailua, HI (US)

(73) Assignee: Alert Core, Inc., Kailua, HI (US)

( * ) Notice: Subject to any disclaimer, the term of this patent is extended or adjusted under 35 U.S.C. 154(b) by 338 days.

(21) Appl. No.: 15/164,681

(22) Filed: May 25, 2016

Related U.S. Application Data

(63) Continuation-in-part of application No. 14/789,136, filed on Jul. 1, 2015, now Pat. No. 9,706,962, which is a continuation-in-part of application No. 14/132,808, filed on Dec. 18, 2013, now Pat. No. 9,226,706.

(Continued)

(51) Int. Cl.
*A61B 5/00* (2006.01)
*A61B 5/11* (2006.01)
*A63B 24/00* (2006.01)

(52) U.S. Cl.
CPC ............ *A61B 5/486* (2013.01); *A61B 5/0013* (2013.01); *A61B 5/0077* (2013.01); *A61B 5/1107* (2013.01); *A61B 5/1116* (2013.01); *A61B 5/1121* (2013.01); *A61B 5/1128* (2013.01); *A61B 5/6831* (2013.01); *A61B 5/7425* (2013.01); *A61B 5/7435* (2013.01); *A61B 5/7475* (2013.01); *A63B 24/0062* (2013.01); *A61B 2503/10* (2013.01); *A61B 2560/0475* (2013.01)

(58) Field of Classification Search
CPC ..... A61B 5/486; A61B 5/0013; A61B 5/0077; A61B 5/1107; A61B 5/1116; A61B 5/1121; A61B 5/1128; A61B 5/6831; A61B 5/7425; A61B 5/7435; A61B 5/7475; A61B 2503/10; A61B 2560/0475; A63B 24/0062
See application file for complete search history.

(56) References Cited

U.S. PATENT DOCUMENTS 4,664,130 A * 5/1987 Gracovetsky .......... A61B 5/103 600/546
5,474,083 A * 12/1995 Church ................ A61B 5/0488 600/546

(Continued)

*Primary Examiner* — Jonathan M Dunlap
*Assistant Examiner* — Philip L Cotey
(74) *Attorney, Agent, or Firm* — Staniford Tomita LLP

(57) ABSTRACT

A wearable device has a core contraction sensor and a movement sensor which transmits signals to a processor which analyzes the signals. The core contraction signal may determine if the user's core is contracted or relaxed. A video camera on a smart device may be used with the wearable device to record video of a user while data from the sensors on the wearable device are also recorded. The core contraction and movement sensor data may be sent to and viewed on the smart device display together with video of the user performing a movement. The simultaneous viewing of the video and sensor data may provide immediate feedback to the user regarding the timing of core contractions with body movements in an athletic, training, or therapeutic movement to allow the user to modify and improve coordination of core contraction with body movements to improve movement performance and achieve better results.

20 Claims, 36 Drawing Sheets

Related U.S. Application Data

(60) Provisional application No. 62/166,093, filed on May 25, 2015, provisional application No. 61/739,160, filed on Dec. 19, 2012.

(56) References Cited

U.S. PATENT DOCUMENTS

| | | | | |
|---|---|---|---|---|
| 5,823,913 | A * | 10/1998 | Aruin | A63B 23/0244 482/4 |
| 6,185,451 | B1 * | 2/2001 | Richardson | A61B 5/0488 600/546 |
| 7,733,224 | B2 * | 6/2010 | Tran | G06F 19/3418 340/540 |
| 8,167,799 | B2 * | 5/2012 | Ronchi | A61B 5/0488 600/301 |
| 8,461,988 | B2 * | 6/2013 | Tran | G06F 19/3418 340/540 |
| 9,775,520 | B2 * | 10/2017 | Tran | G06F 19/3418 |
| 2002/0143277 | A1 * | 10/2002 | Wood | A61B 5/1071 600/595 |
| 2002/0170193 | A1 * | 11/2002 | Townsend | A61B 5/1116 33/512 |
| 2002/0177882 | A1 * | 11/2002 | DiLorenzo | A61B 5/048 607/45 |
| 2003/0065365 | A1 * | 4/2003 | Zhu | A61N 1/36542 607/17 |
| 2003/0135140 | A1 * | 7/2003 | Bosco | A61H 23/02 601/46 |
| 2005/0043661 | A1 * | 2/2005 | Nashner | A61B 5/1038 602/26 |
| 2006/0276701 | A1 * | 12/2006 | Ray | A61B 5/0816 600/354 |
| 2007/0167879 | A1 * | 7/2007 | Cochran | A61B 5/11 600/595 |
| 2008/0001735 | A1 * | 1/2008 | Tran | G06F 19/3418 340/539.22 |
| 2008/0234113 | A1 * | 9/2008 | Einav | A61B 5/103 482/66 |
| 2009/0005834 | A1 * | 1/2009 | Weintraub | A61H 23/0263 607/48 |
| 2009/0131759 | A1 * | 5/2009 | Sims | A61B 5/1135 600/301 |
| 2010/0240495 | A1 * | 9/2010 | Law | A63B 21/0004 482/9 |
| 2011/0172060 | A1 * | 7/2011 | Morales | A63B 69/004 482/8 |
| 2011/0184318 | A1 * | 7/2011 | Kodama | A61B 5/033 600/588 |
| 2011/0230782 | A1 * | 9/2011 | Bartol | A61B 5/0488 600/546 |
| 2011/0269601 | A1 * | 11/2011 | Nelson | A47C 7/021 482/8 |
| 2011/0270135 | A1 * | 11/2011 | Dooley | A61B 5/1121 600/595 |
| 2012/0116256 | A1 * | 5/2012 | Stavdahl | A61B 5/04888 600/595 |
| 2012/0215076 | A1 * | 8/2012 | Yang | A61B 5/0205 600/301 |
| 2012/0259648 | A1 * | 10/2012 | Mallon | G06F 19/3418 705/2 |
| 2014/0163412 | A1 * | 6/2014 | Jacobson | A61B 5/0488 600/546 |
| 2014/0174174 | A1 * | 6/2014 | Uehara | A61B 5/227 73/379.01 |

* cited by examiner

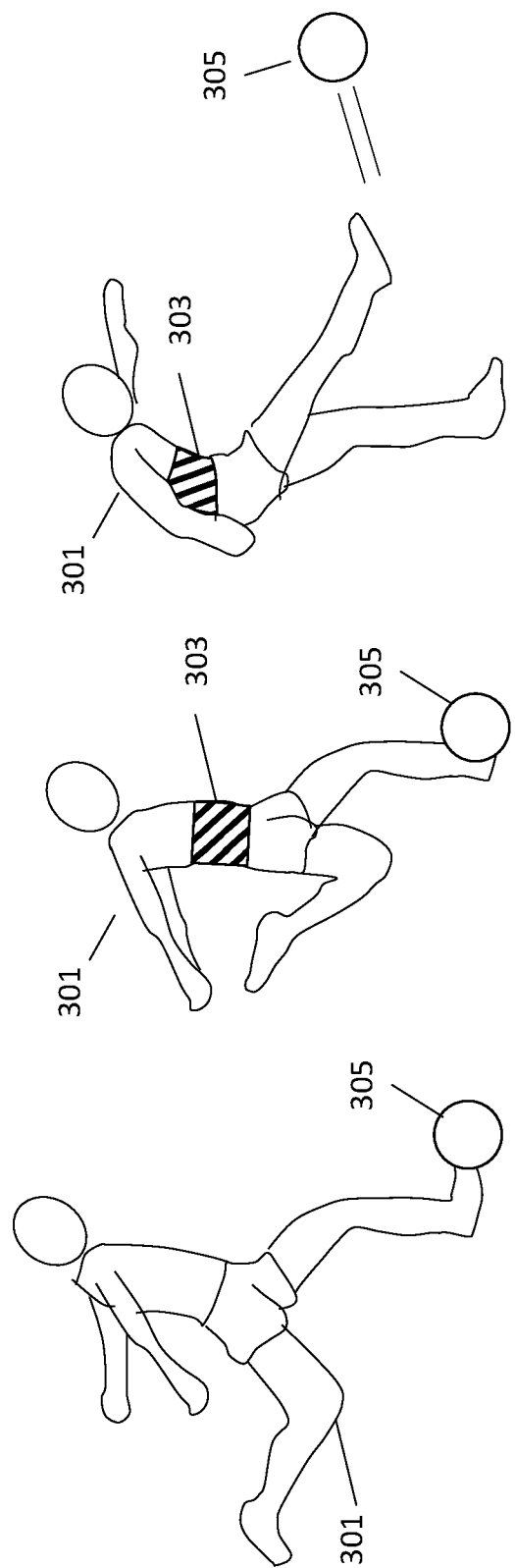

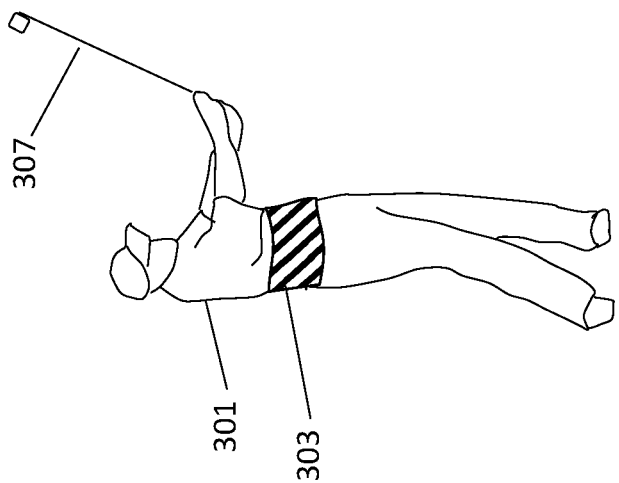
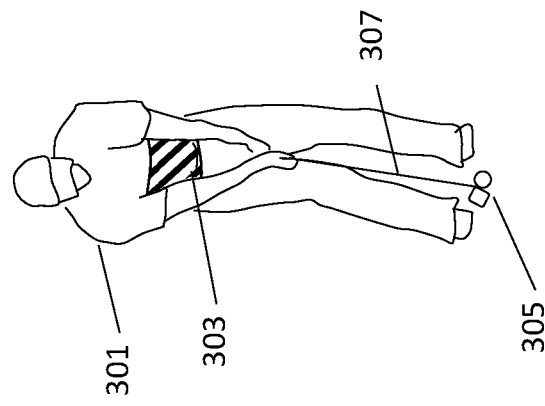
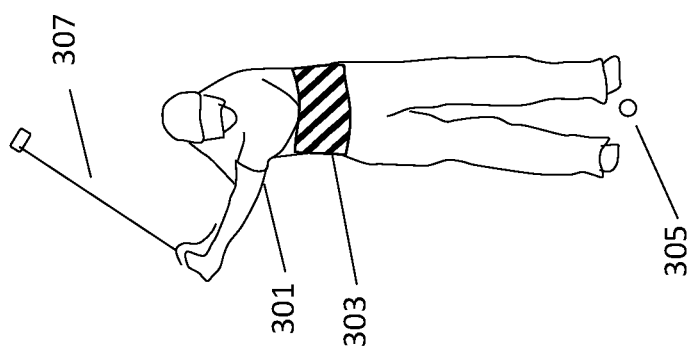

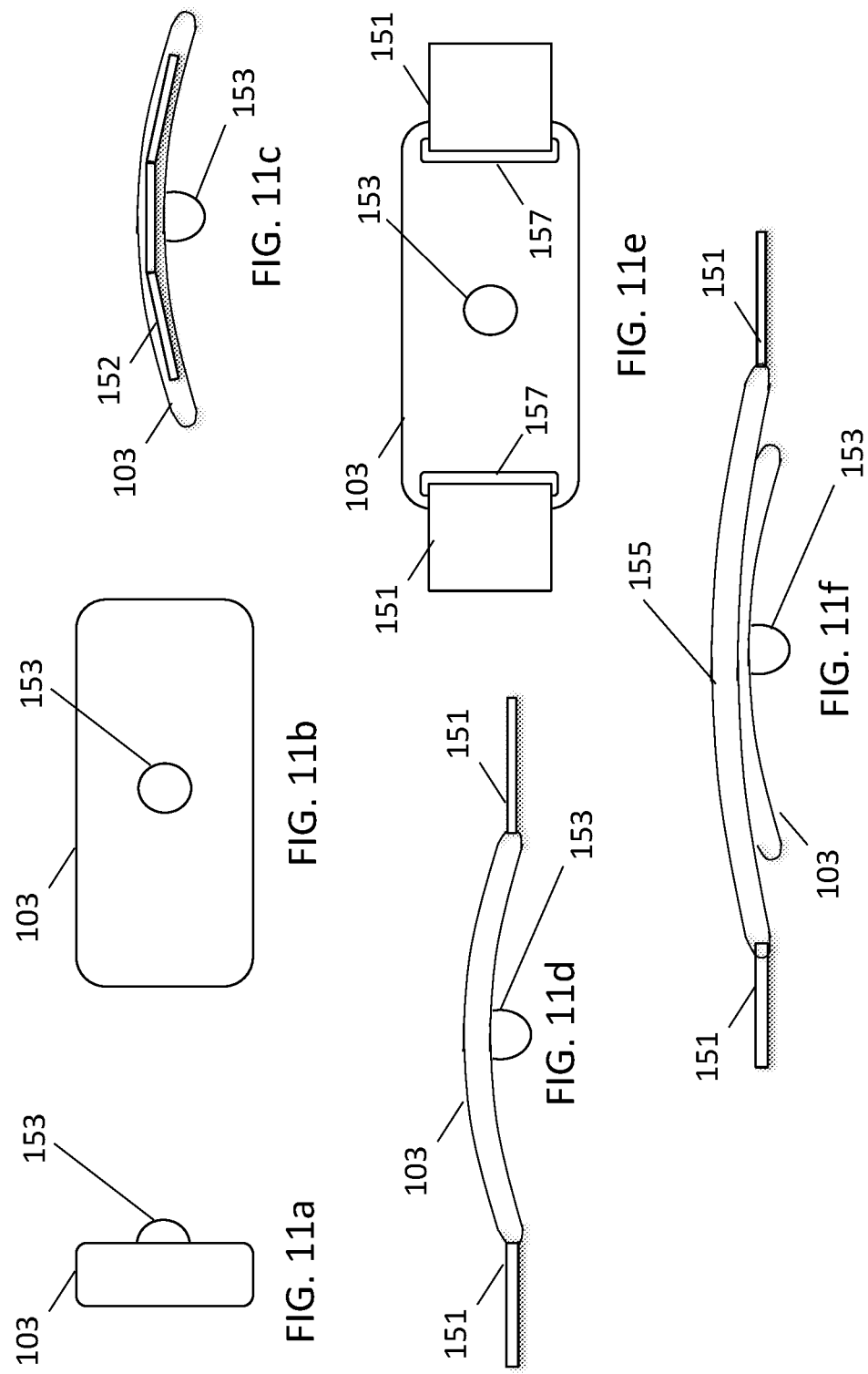

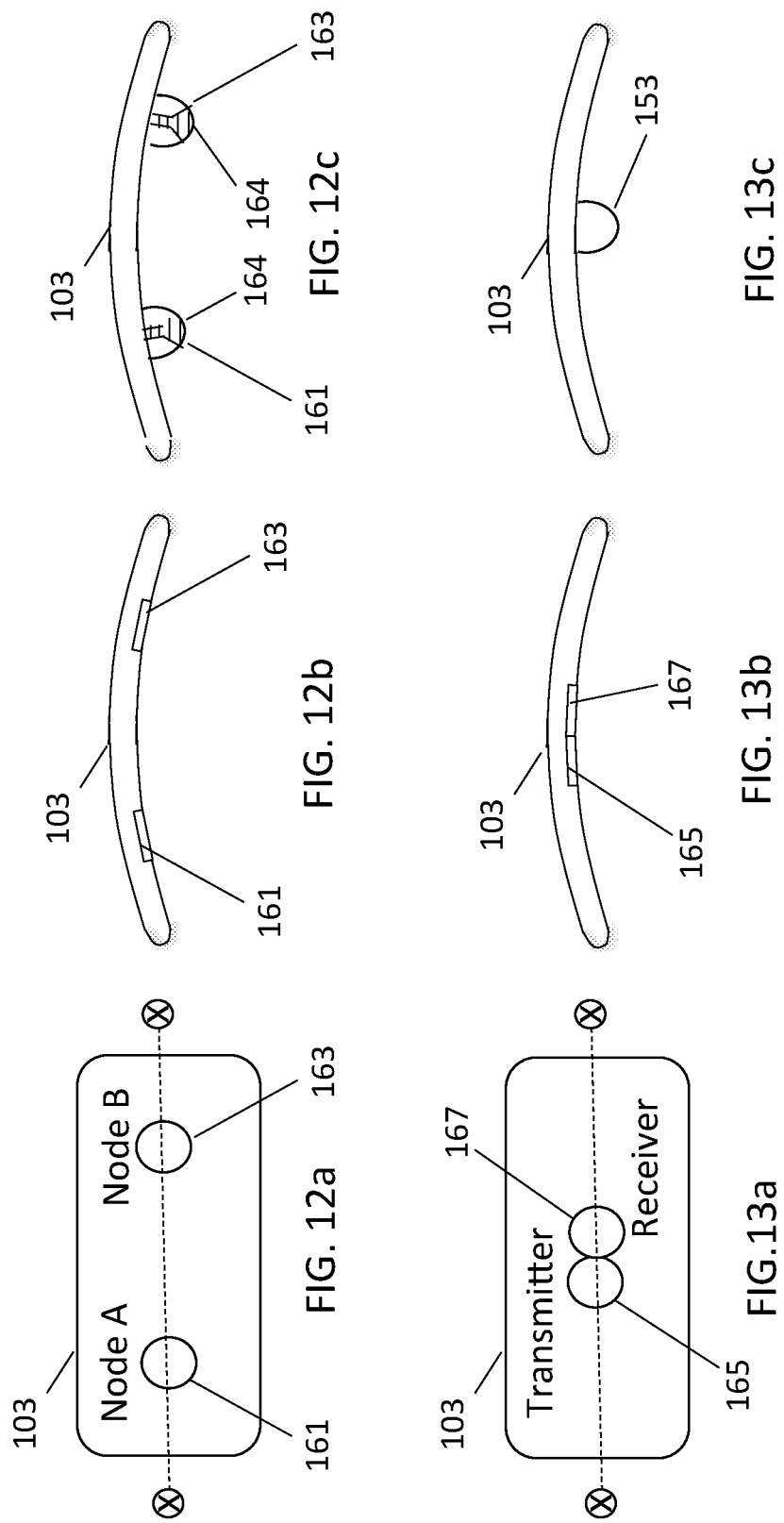

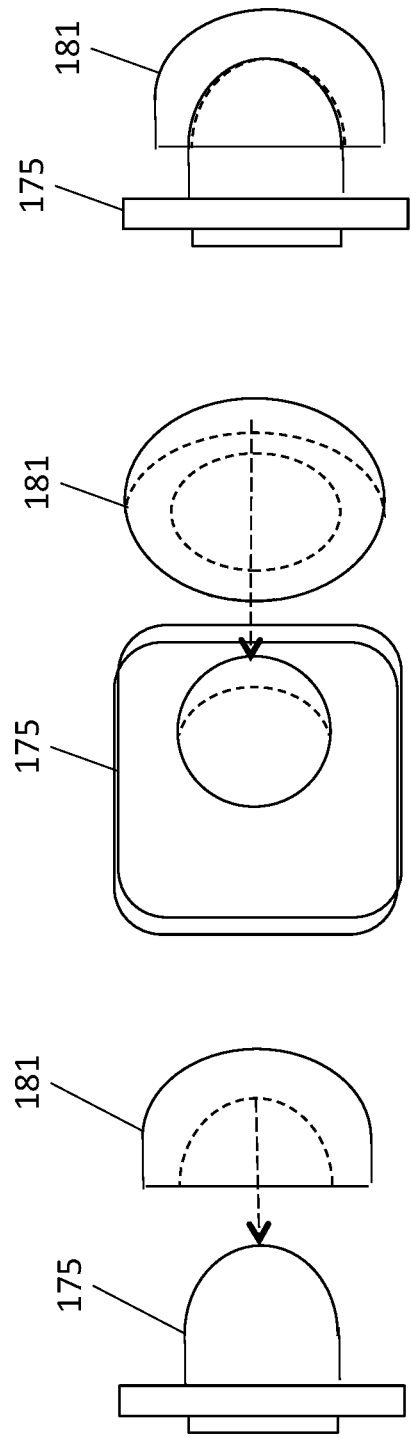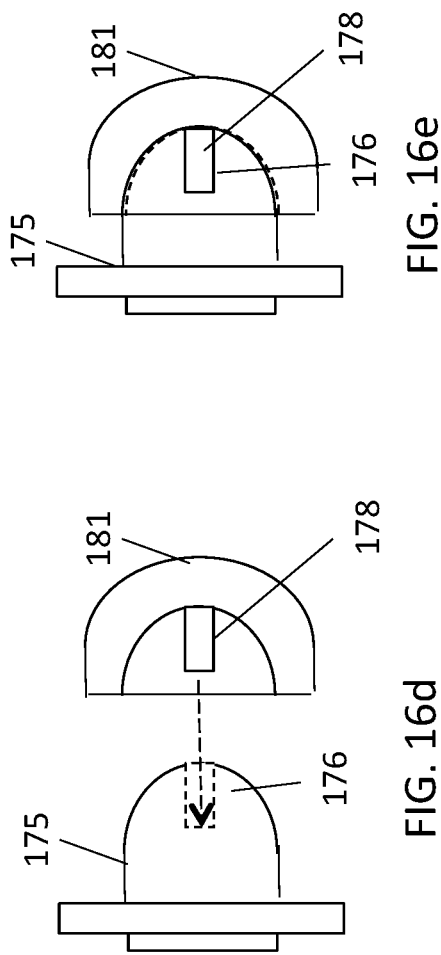

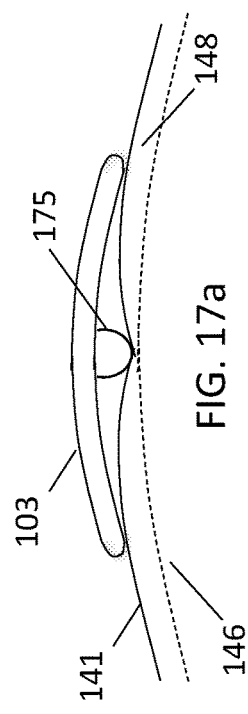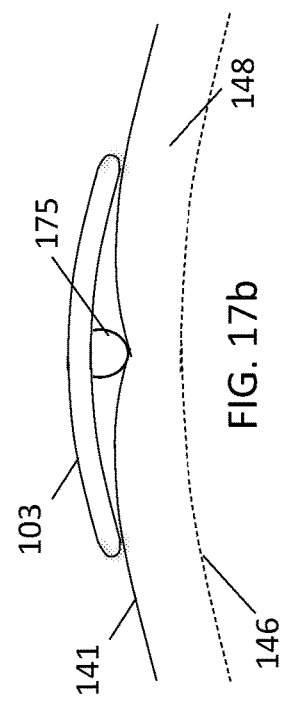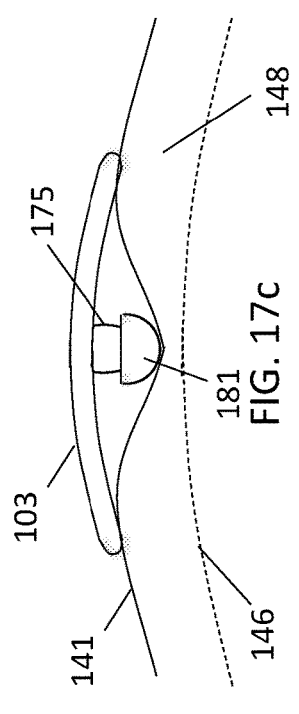

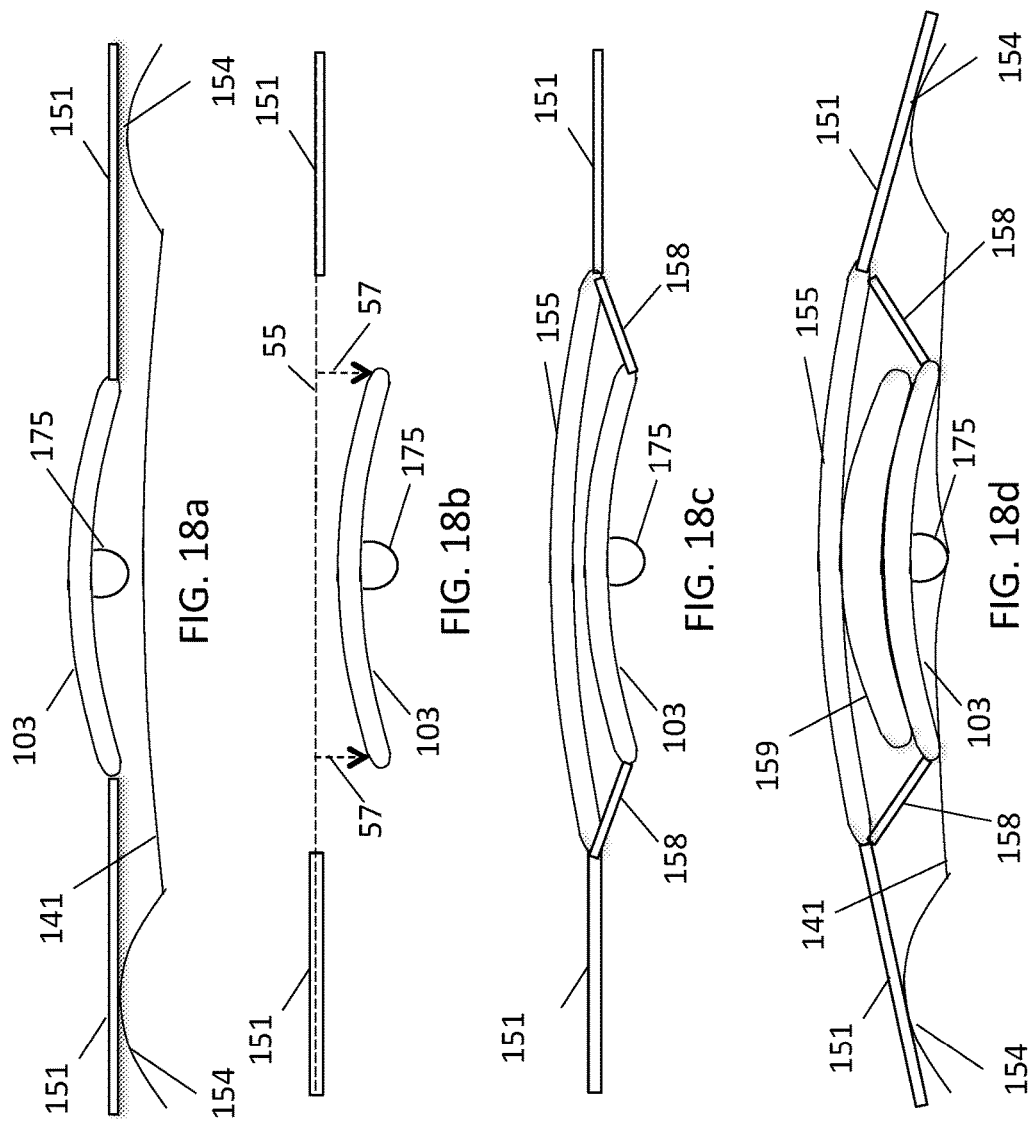

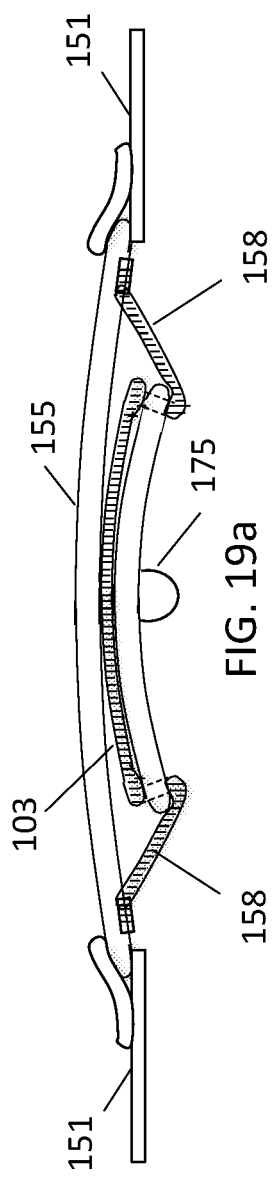
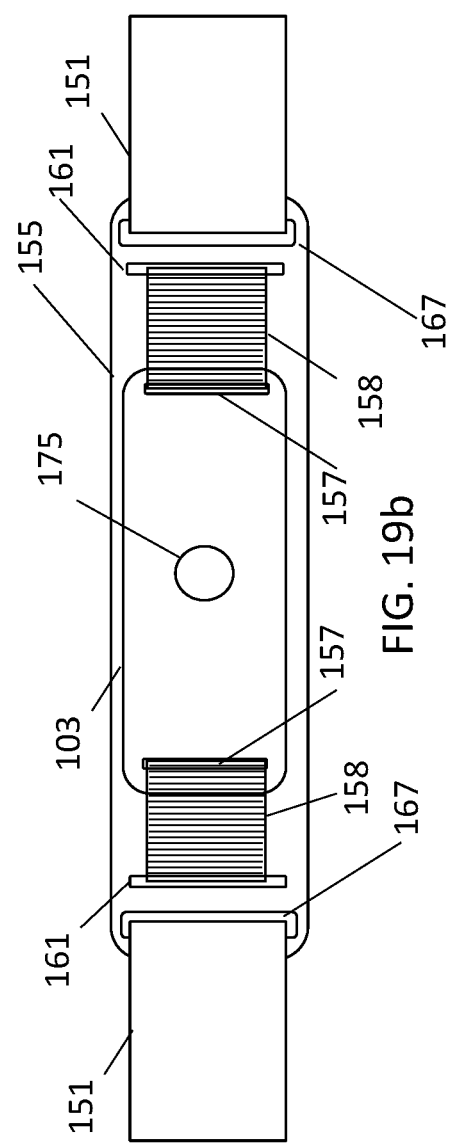

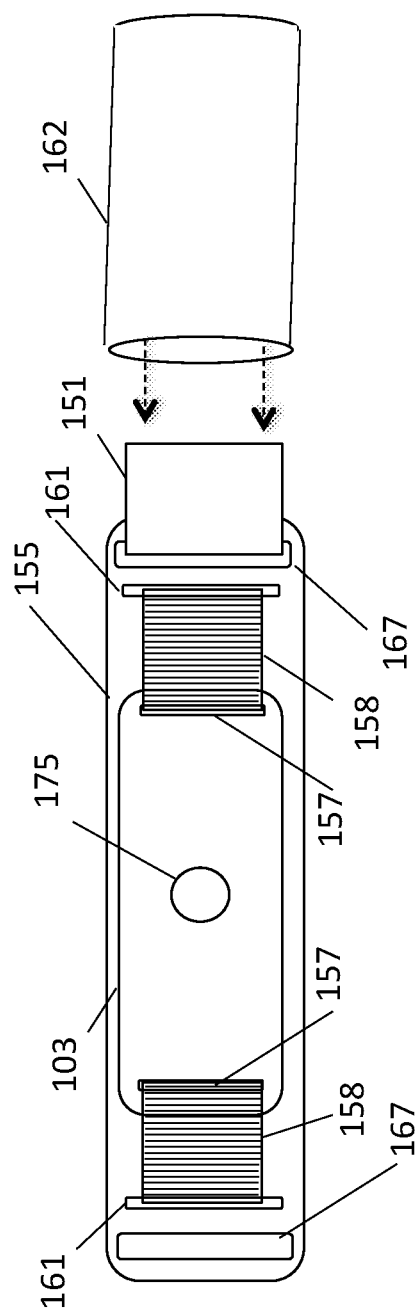
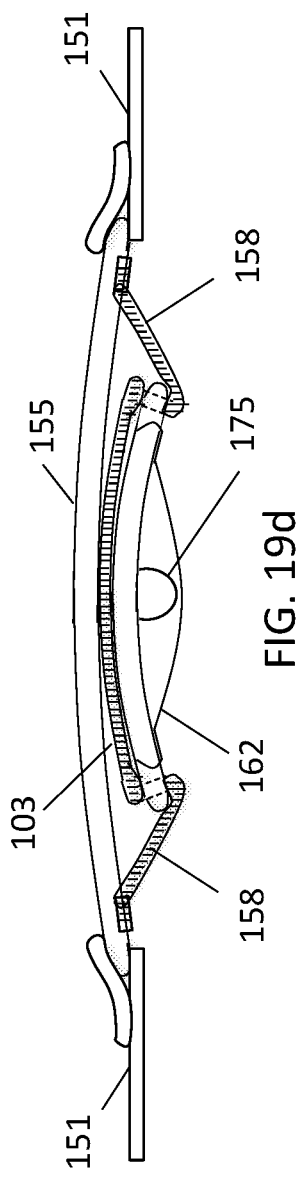
FIG. 19c
FIG. 19d

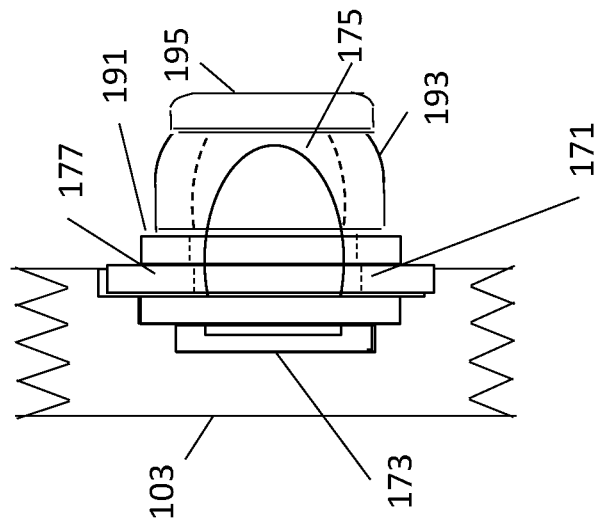
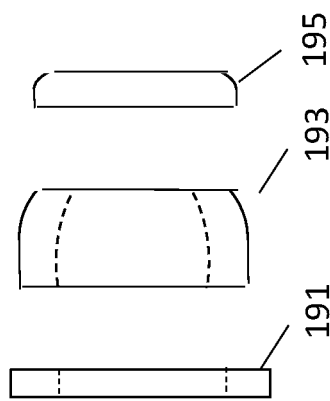
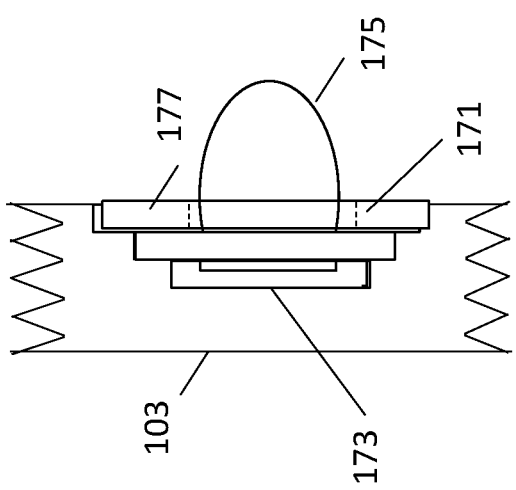
FIG. 20b
FIG. 20a

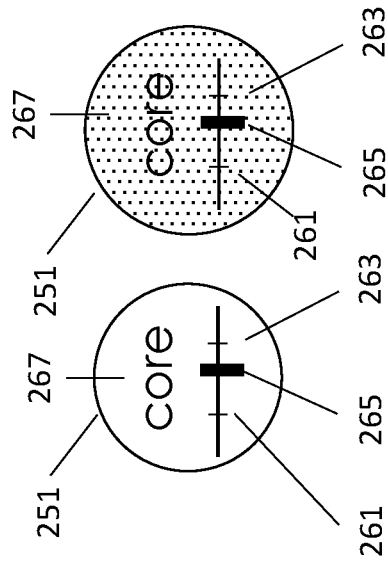
FIG. 26d
FIG. 26c
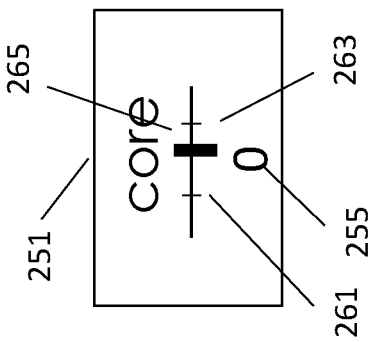
FIG. 26b
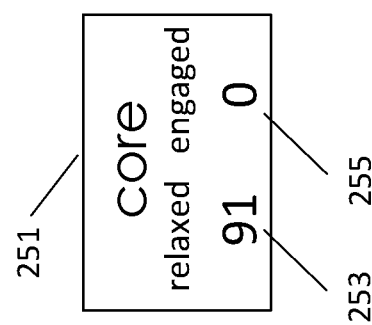
FIG. 26a

SYSTEM AND METHOD FOR DEVELOPING CORE MUSCLE USAGE IN ATHLETICS AND THERAPY

CROSS-REFERENCE TO RELATED APPLICATIONS

This application also claims priority to U.S. Provisional Application No. 62/166,093, entitled "System For Teaching And Improving Athletic Performance Utilizing Wearable Device Worn Over The Core Muscles", filed May 25, 2015. This application is also a continuation in part of U.S. patent application Ser. No. 14/789,136, entitled "Apparatus And Method For Teaching And Algorithms For Identifying Qualifying Movements", filed Jul. 1, 2015, which is a continuation in part of U.S. patent application Ser. No. 14/132,808, entitled "System, Apparatus, And Method For Promoting Usage Of Core Muscles And Other Applications", filed Dec. 18, 2013, now U.S. Pat. No. 9,226,706 which claims priority to U.S. Provisional Application No. 61/739,160, entitled "System For Promoting Usage Of Core Muscles And Other Applications", filed Dec. 19, 2012. The disclosures of U.S. patent application Ser. Nos. 14/132,808, 14/789,136, 14/652,542, 14/817,964, 61/739,160, and 62/154,626 are hereby incorporated herein by reference in their entirety.

FIELD OF THE INVENTION

Embodiments disclosed relate to apparatus, systems, and methods for improvement of athletic, therapeutic, and training movements with core muscle usage by using video in conjunction with detecting core muscle usage and body movements using a wearable device. Embodiments also relate to apparatus, systems, and methods for enabling recorded data from a wearable device and a smart device that may be out of communication range during the recording period to be viewed time-synchronized during a playback period. Using data from the sensors to identify movements and core muscle engagements, feedback is provided to the user regarding correct or incorrect core muscle use or preferred or unpreferred core muscle use. Embodiments disclosed also relate to apparatus, systems, and methods for improvement of athletic, therapeutic, and training movements with specific muscle usage by using video in conjunction with detecting specific muscle usage and body movements using a wearable device where the specific muscle may include the *vastus medialis* oblique (VMO).

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be embodiments of the invention.

In recent years, there has been explosive growth in the number of portable and handheld devices that include but are not limited to sensors such as accelerometers, gyros, magnetometers, altimeters, and/or pressure sensors. Examples of such devices include smart phones, cell phones, gaming devices, and wearable devices (or wearables).

In gaming devices, tilt or angles of rotation are often tracked and used to control elements of the game. A large number of wearables target health and fitness applications where steps taken and flights of stairs taken by device users are tracked utilizing accelerometers and altimeters.

Inertial navigation is a method utilizing accelerometers, gyroscopes or gyros, and a microprocessor contained on a moving object to continuously calculate device positions utilizing dead reckoning the position, orientation, and velocity of the object. Dead reckoning is the process of calculating the current position by using a previously determined position and advancing that position based on estimated speeds over known elapsed time. A system implementing inertial navigation is self-contained and requires no external references. Inertial navigation has generally been used by aircraft, spacecraft, guided missiles, and ocean craft. Inertial navigation may be used in embodiments of the inventive concepts described in this disclosure targeting systems and devices for the wearables market.

Most health and fitness wearables on the market today may track one or more of the following: steps taken, number of stairs taken, heart rate, movement activity, and sleep patterns. These devices generally utilize accelerometers, altimeters, light sources and sensors, and voltage sensors to sense and detect the parameters they measure and track.

Back injuries are a common problem. Core muscle based support can be used as a means for improving back strength, supporting the lumbar spine, and preventing back injuries. While there has been much attention in exercise and rehabilitation environments to strengthening the core muscles through various exercises, very little emphasis has been placed on developing the habit for deliberate contraction and use of the core muscles in every day activities. What is needed for exercise and rehab is a system and method for improving core based support through core muscle contraction exercise. Such a system and method may encourage users to develop neural patterning to contract core muscles deliberately when the support provided by the core muscles may be beneficial. This system and method may further develop neural patterning to coordinate the contraction of the core muscles before and during body movements.

Core muscle strengthening is emphasized for athletic performance improvement. What is needed for applications in athletics is a system and method for improving core based support in situ during athletic movements.

SUMMARY OF THE INVENTION

In U.S. Pat. No. 9,226,706, entitled "System, Apparatus, And Method For Promoting Usage Of Core Muscles And Other Applications", an inventive system is presented including a wearable device which monitors a user's movements for Qualifying Movements (QM), where a QM is a movement for which support from contraction of the core muscles may be beneficial to the lumbosacral junction and lumbar spine. When a QM is identified, the system determines whether or not the QM is protected or not protected based on the status of the user's core before, during, and after the QM. Objectives of the system include: having the user contract their core muscles during the time the stress on the lumbar spine and lumbosacral junction is greatest during a QM; and having the user develop the habit of contracting their core muscles during QMs such that they continue this beneficial practice even without the system. In general, if the core is contracted before and during the QM, the QM may be considered protected. However, since it is protecting the lumbosacral junction and lumbar spine when the stress is greatest that matters most, having the core contracted during periods when, for example, the acceleration or deceleration is greater than a threshold may also result in a QM being considered protected. An overall objective of the system is to provide system and method for developing core muscle usage employing video together with data from the wearable device. A movement, for example, an athletic movement such as serving a volleyball may be video recorded and the sensor data from the wearable worn on a portion of the athlete's core muscles may simultaneously record data from a core contraction sensor and a movement sensor. This combination data of video and sensor data, including data derived from the sensor data may be displayed at the same time in slow motion. This may help the athlete practice different strategies for coordinating core muscle contraction with athletic body movements.

The wearable device and app described in this and U.S. Pat. No. 9,226,706 have been described to develop usage of the core muscles. The wearable and app may also be used to monitor other muscles and other body movements. For example, after a knee surgery, the *Vastus Medialis* Oblique (VMO) muscle in the thigh will tend to atrophy. The described device may be used in a modified strap that is then placed over the VMO. The core contraction sensor becomes a muscle contraction sensor where in this case, the muscle is the VMO. As the user changes from the seated position to the standing position, it may be desirable that the user engages the VMO prior to and through the movement from seated to standing. The monitoring of the movement of the thigh may be performed by the movement sensor and contraction of the VMO may be monitored using the muscle contraction sensor. Feedback may be provided based on the timing relationship between contraction of the VMO and movement of the thigh.

Knee and body pain is sometimes attributable to locking or hyperextending one's knees during their gait. In this abnormal gait, the knee joint moves past its normal range of motion, opposite to the direction they are stepping and locks, while the person transfers weight over this locked leg and forward. This may cause knee pain and instability. By monitoring the timing of contraction of the VMO relative to movements identified by the movement sensor, a correct step may be identified by a peak in the muscle contraction sensor as the movement sensor detects that the device is substantially horizontal as the body rolls over the leg being monitored. An incorrect step involving a hyperextended knee may be identified by little or no peak during the same instant as the movement sensor detects that the device is substantially horizontal as the body rolls over the leg being monitored. The peak of the muscle contraction sensor may occur at a different moment in the gait. The magnitude of the muscle contraction sensor peak may also be much less than the magnitude of the muscle contraction sensor peak during a correct step. In some embodiments, the system may be used to detect a muscle or core contraction before or during a movement. In another embodiment, the system may be used to detect a preferred execution of a movement from an unpreferred execution of a movement based on the time location of the muscle or core sensor characteristics such as a contraction peak, at specific monitoring moments related to a specific time in a movement as identified by the data derived from the movement sensor.

The present description will focus mainly on development of the core muscles during athletic movements, fitness training, and movements in rehab. However, the inventive concepts described here and in the other descriptions may be applied to the development and training of other muscles. The VMO is one example.

A sequenced core may refer to core muscles that are contracted deliberately and where the core contractions or core engagements are coordinated with other body movements. For example, a person practicing a sequenced core may engage their core muscles while seated, and hold the engagement while transitioning from the seated to the standing position. Once standing, the person may then relax their core muscles. A benefit for the person practicing the sequenced core during the sit-to-stand movement is their lumbar spine receives protective support from the contracted core muscles.

Athletes of many types of sports are strongly encouraged to perform exercises to strengthen their core muscles. In some applications, athletes are being encouraged to utilize a sequenced core, that is one engaged deliberately and where the engagement or contraction is coordinated with other body movements, in this case, athletic movements. In athletic applications, an engaged core provides stiffness in the torso region that allows power from movement in the legs and lower body to be transferred to the upper torso and eventually the arms and hands. Without an engaged core, energy from the leg movements may be lost during the athletic movement. Examples of athletic movements that may benefit from an engaged core include a golf, baseball, tennis, or cricket swing, a throw, a volleyball spike, or a soccer kick. In athletic applications, a sequenced core may provide a number of benefits including: a. Stability and Balance—the engaged core wraps around the torso and hips helping to establish the torso region as a center of gravity; this may keeps the athlete from becoming top heavy during upper body thrusting; and allow for example, a football running back quick side to side movements since their body weight is not committed to one side or the other; b. Power Transfer—weight shifts from left to right foot as well as hip rotation which may transfer energy from the ground through the feet and legs and up through the core region to the upper body, and finally to the arms and hands may benefit from a sequenced core; c. Protection of the Spine and Torso—injury mitigation due to support of the spine and avoidance of awkward and out-of-control positioning may be encouraged with a sequenced core; and d. Consistency and Repeatability of Athletic Movements—may be increased with a sequenced core that may encourage the athlete to rely less on quick and sometimes jerky movement of the arms and hands to generate power to a movement that includes the larger muscles of the legs and torso to generate power where this power is transferred from the lower body to arms and hands through a sequenced core.

Since engaging the core during an athletic movement requires energy from the athlete, it is critical to incorporate the timing of the engagement into the sequence of the athletic movement. The stiffness provided by the engaged core needs to be timed appropriately to achieve the maximum benefit.

The use of video recording is very widespread and commonplace with good quality video cameras on smart devices and specialized cameras for athletics and active lifestyle activity video recording. Video feedback of an athlete may be very valuable for numerous reasons including that it allows the observation of subtle movements and changes in position and weight distribution. On the other hand, video recording is quite costly in terms of storage or memory space requirements. When using video as a tool for coaching and athletic performance improvement, care must be taken to reduce storage requirements.

In some sports such as running track, small subtle changes in techniques accumulate over the course of a race. For example, large left to right rotations during the course of a run can slow a runner down and keep them from moving forward at their best speed. A contracted core may reduce the magnitude of such rotations while supporting the lumbar spine. The core contraction sensor and the movement sensor on the wearable device may be used to record data associated with the core and movements throughout a run. Video recording may be used to monitor form throughout the run. This data may be used after a run to identify changes and areas of improvement. In an embodiment, the wearable device may provide feedback during the run to inform the athlete via buzzing or reporting to a smart watch or other handheld device. In this situation, the athlete may wear the wearable device while a coach controls a camera that records video of the athlete. After the athletic event, in this case which is a run, the athlete and coach may review the technique used and sensor data immediately following the run. This may allow the athlete to try several strategies in a short period of time and record the results, including run times, and data from the worn sensors and video.

In an embodiment, the system disclosed in this application provides data to a user to improve the use of core muscles during an athletic, training, or rehab movement. In addition to core contraction and movement data taken by the wearable device, a video of the athlete performing the athletic movement is recorded. This data may be played back as selected by the user to observe the timing of the core contraction, together with other movement data, and video of the athlete. Comments by the user or coach may be recorded and stored along with the recorded data for further later analysis. Viewing this data just after an athletic movement is performed may provide immediate feedback to the athlete user and coach to modify, for example, the timing of core contractions and how it is integrated with other parts of the movement. Other parts of the movement may include weights shifts, rotations, movements in 3 dimensions, as recorded by the movement sensors and video of the athlete.

In an embodiment, the system disclosed may use data from the core sensor and movement sensor to determine moments of pause by the athlete, and the start of movements and end of movements by the athlete. These pauses and identified movement starts and movement ends may be used to determine the start and stop times for recording the sensor and video data. In an embodiment, if the duration between a start and stop is less than a minimum duration, the recording may be discarded. In an embodiment, if no movement is detected by the movement sensors, the recording may be discarded. In another embodiment, if a core contraction is not identified during the movement, the recording may be discarded.

In an embodiment, a wearable device with a core contraction sensor and movement sensor where both sensors are coupled to a first memory may be worn on an athlete, for example, a runner. A video camera coupled to a second memory may be controlled by a coach. Before the runner begins running, the wearable device and video camera begin recording data, the wearable device storing data in the first memory and the video camera storing data in the second memory. At the end of the run, the wearable device stops storing data to the first memory and the video camera stops storing data to the second memory. The data from the first memory and second memory may be combined on to one device. And the selected sensor data and video data may be played back on a device with a display. In an embodiment, the wearable device and the video camera synchronize to establish a common time base before the start of the run. This common time base is used to time stamp data stored in the first memory and the second memory. This may facilitate the joint playback of sensor data and video data so that they are substantially time synchronized.

In another embodiment, the wearable device and the video camera may perform a first synchronization to establish a common start time before the start of the run and begin separate timers on the wearable device and the video camera. If there is any difference in the frequency of the timing reference blocks on both devices, the timers will have increasingly different values as time transpires. At the end of the run, the wearable device and video camera may both stop their respective timers. Any difference in the timing reference blocks on the wearable device and the video camera will reflect in a difference in the ending timer values on the wearable device and the video camera. The time difference at the end of the run may be combined with the time transpired since the first synchronization to determine a time offset between the timing reference blocks on the wearable device and the video camera. This time offset may be used to correct the time stamps on one or both of the first memory and the second memory in order to improve the synchronicity between the data from the first memory and the second memory where the sensor data on the wearable device is stored in the first memory and the video data from the video camera is stored in the second memory. In an embodiment, instead of changing time stamps, data may be duplicated or removed from one of the memories to account for differences in the timing reference blocks.

In another embodiment, other equivalent techniques may be used to time synchronize the data from the first memory and second memory. In an embodiment, time reference oscillator on the wearable device or the video camera may be modified to minimize frequency error between the reference oscillator on the wearable device and the video camera.

In an embodiment, the portions of video data that is saved maybe identified as occurring between pauses as identified by the core contraction sensor and the movement sensor.

In an embodiment, video movement and identification techniques may be applied to determine movement direction, axes of rotation, and moments of pause and incorporated into feedback to the user.

In an embodiment, certain athletic movements may be identified as qualifying movements. The algorithms and techniques for identifying protected qualifying movements and unprotected qualifying movements and providing immediate feedback may be utilized.

The core contraction is useful in performing protected qualifying movements which are qualifying movements that are performed with the core muscles properly contracted during the qualifying movements. The protected qualifying movements and contraction sensor wearable devices are described in more detail in U.S. Pat. No. 9,226,706.

A comprehensive method to teach users to contract their core during athletic, fitness and strength training, and rehab may be beneficial to users. A simple to use device and system that shows core muscle usage with together with video of a user performing athletic or training movements or athletic events may provide immediate and continuous feedback during training and practice sessions to allow real time modifications to the timing of core engagements coordinated with other body movements. Such real-time modifications may be beneficial to optimize and improve the timing of core usage during athletic and training movements or athletic events. Core contraction identification with the identification of other metrics such as body movement, body positioning, body rotation with simultaneous video of the user may be beneficial to users, as well as coaches, therapists, trainers, and others teaching the development of the sequenced core to athletes, clients, and patients.

BRIEF DESCRIPTION OF THE DRAWINGS

Other objects and features of the present invention will become apparent from the following detailed description considered in connection with the accompanying drawings which disclose several embodiments of the present invention. It should be understood, however, that the drawings are designed for the purpose of illustration only and not as a definition of the limits of the invention.

FIGS. 3a-3c illustrate a segment of a soccer kick sequence.

FIGS. 4a-4c illustrate a segment of a gold swing sequence.

FIG. 11a illustrates a side view of an embodiment of the wearable device and core sensor interface.

FIG. 11b illustrates a front view of an embodiment of the wearable device and core sensor interface.

FIG. 11c illustrates a top view of an embodiment of the wearable device and core sensor interface showing an internal compartment to house electronics, sensors, and a battery.

FIG. 11d illustrates a top view of an embodiment of the wearable device and core sensor interface attached to a belt.

FIG. 11e illustrates a front view of an embodiment of the wearable device and core sensor interface attached to a belt.

FIG. 11f illustrates a top view of an embodiment of the wearable device and core sensor interface attached to a strap with the strap attached to a belt.

FIG. 12a illustrates a front view of an embodiment of the wearable device and core sensor interfaces utilizing two nodes for core contraction sensing.

FIG. 12b illustrates a top view of an embodiment of the wearable device and core sensor interfaces utilizing two non-protruding sensing nodes.

FIG. 12c illustrates a top view of an embodiment of the wearable device and core sensor interfaces utilizing two protruding sensing nodes.

FIG. 13a illustrates a front view of an embodiment of the wearable device and core sensor interfaces for core contraction sensing having a transmitter and a receiver.

FIG. 13b illustrates a top view of an embodiment of the wearable device and core sensor interfaces for core contraction sensing using non-protruding sensor interface structures having a transmitter and a receiver.

FIG. 13c illustrates a top view of an embodiment of the wearable device and core sensor interface for core contraction sensing using a combined protruding sensor interface structure having a transmitter and a receiver.

FIG. 16a illustrates an embodiment of a bumper with an extender cap.

FIG. 16b illustrates a perspective view of an embodiment of a bumper with an extender cap.

FIG. 16c illustrates an embodiment of a bumper with an extender cap placed on the bumper.

FIG. 16d illustrates an embodiment of a bumper with an additional cavity and an extender cap with an additional extrusion to fit into the additional cavity in the bumper.

FIG. 16e illustrates an embodiment of the bumper and the extender cap placed on the bumper.

FIG. 17a illustrates a cross sectional view of an embodiment of the device and bumper placed on the core section showing the user's skin and underlying core muscles for a user with less body fat.

FIG. 17b illustrates a cross sectional view of an embodiment of the device and bumper placed on the core section showing the user's skin and underlying core muscles for a user with more body fat.

FIG. 17c illustrates a cross sectional view of an embodiment of the device and bumper with an extender cap placed on the core section showing the user's skin and underlying core muscles for a user with more body fat.

FIG. 18a illustrates a cross sectional view of an embodiment of the device, bumper, and belt on a user with prominent hip bones.

FIG. 18b illustrates a cross sectional view of an embodiment of the device separating from the adjoining line and toward the core muscles.

FIG. 18c illustrates a cross sectional view of an embodiment of the device with a strap connecting both ends of a belt and gap extenders connecting to the device to enable the device to separate from the adjoining line toward the core.

FIG. 18d illustrates a cross sectional view of an embodiment of the device with a gap filler for holding the device against the core on a user with prominent hip bones.

FIG. 19a illustrates a top view of a cross section of an embodiment of the device, bumper, strap, gap extender, and belt.

FIG. 19b illustrates a front view of an embodiment of the device, bumper, strap, gap extender, and belt.

FIG. 19c illustrates a front view of an embodiment of the device, bumper, strap, gap extender, and belt with a tubular shaped material to slide over the device and bumper.

FIG. 19d illustrates a top view of a cross section of an embodiment of the device, bumper, strap, gap extender, and belt with a tubular shaped material positioned over the device and bumper.

FIG. 20a illustrates a cross section of the FSR, bumper, and frame in place with the addition of a flat donut ring and mushroom cap to be placed on the bumper head external to the device.

FIG. 20b illustrates the cross section with the ring and mushroom cap in place.

FIG. 26a illustrates a button implementation for the app using numbers for the sensorEngaged and sensorRelaxed.

FIG. 26b illustrates a button implementation for the app using a slider for sensorRelaxed.

FIG. 26c and FIG. 26d illustrates a circular button implementation for the app where the radius of the circle changes as the core is engaged.

DETAILED DESCRIPTION

Figure 1A:
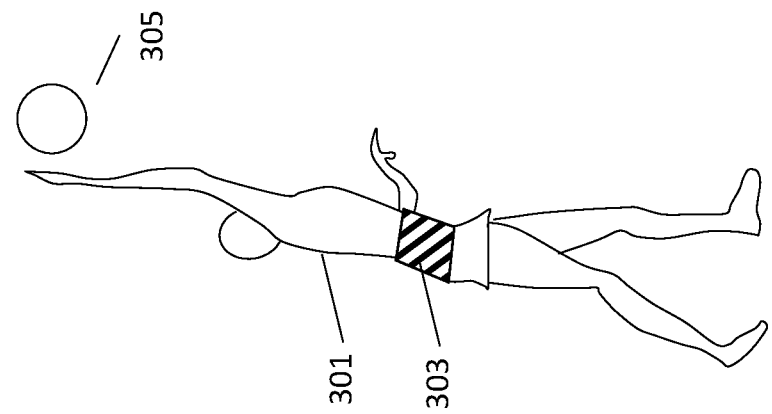
FIGS. 1a-1c illustrate a segment of a volleyball serve sequence.

In U.S. Pat. No. 9,226,706, an inventive device and system is described, one embodiment of which enables real-time tracking of the inner core muscles. The inventive device and system encourage the development of procedural memory for usage of the core muscles. The core contractions can then be used during Qualifying Movements (QM) which are defined as movements for which contraction of the core muscles may be beneficial in supporting the lumbosacral junction and lumbar spine. The wearable device and system are described to provide feedback to a user as to whether or not the user has engaged their core muscles to stabilize their torso during a golf putting stroke. The description in said patent utilizes the wearable device and a second device that may be worn on the wrist.

In this current description, the use of video recording is used to complement sensor data taken by the wearable device. By viewing a user performing a movement together with an indicator displaying the status of the user's core muscles simultaneously during playback wherein the indicator displaying the status of the user's core muscles may include whether the core muscles are engaged or relaxed and may include the degree of the contraction, the user may use this information to improve the timing and the degree of the core contraction during the movement. Data from the movement sensor on the wearable device may be used to derive orientation information that may be displayed with the video recording. Examples of orientation information may include rotation and movement. In different applications, different preferred orientation information may be displayed. Sensor data or sensor data samples in this description may refer to raw data taken from the sensors without processing or include data derived from the sensors after signal processing algorithms have been applied.

Many athletic movements may be identified as qualifying movements, where a qualifying movement is a movement in which the lumbar spine may benefit from the support provided by engaged core muscles. In addition to receiving recorded video and selected sensor data including core contraction data, the system may inform the user when movements are identified as protected or unprotect qualifying movements. The feedback provided by the system informing of a protected or unprotected qualifying movements may in some applications be immediate, and in some applications, may be provided during playback of the video, contraction sensor, and movement sensor data.

Movement applications that may benefit from a system that utilizes data taken simultaneously by the wearable device including the core contraction sensor and movement sensor, and a video recorder include the improvement of athletic movements, strength and fitness training, physical therapy, occupational therapy, rehab, and occupation related movements. Other applications may also benefit from the system including the wearable device and video camera. Many occupations require lifting of heavy objects. For example, airline check-in attendants lift suitcases and boxes onto conveyor belts; super market and big box store stockers lift boxes filled with products to get products onto store shelves; military personnel lift equipment and weaponry; and carpenters, plumbers, and refrigeration technicians lift building materials appliances. The system employing the wearable device and the video recording device may be used in training and as a reminder in the field for many occupations requiring heavy and regular lifting. Athletes in many sports develop back and disk problems. In some cases, these problems arise due to years of performing athletic movements that are qualifying movements. By learning early in the development of their basic skills how they might protect qualifying movements with an engaged core, the number of back and disk problems for athletes may be reduced.

Emphasis in this description may be directed toward athletic applications. However, the system may be applied to the many applications described above, as well as others including regular movements that may be considered qualifying movements.

A Sequenced Core may refer to core muscles that are contracted deliberately and where the core contractions or core engagements are coordinated with other body movements. The protection of qualifying movements may said to be protected by a sequenced core. For example, a person practicing a sequenced core may engage their core muscles while seated, and hold the engagement while transitioning from the seated to the standing position. Once standing, the person may then relax their core muscles. A benefit for the person practicing the sequenced core during the sit-to-stand movement is their lumbar spine receives protective support from the contracted core muscles.

Athletes of many types of sports are often encouraged to perform exercises to strengthen their core muscles. In some applications, athletes are being encouraged to utilize a sequenced core, that is one engaged deliberately and where the engagement or contraction is coordinated with other body movements. In athletic applications, an engaged core provides stiffness in the torso region that allows power from movement in the legs and lower body to be transferred to the upper torso and eventually the arms and hands. Without an engaged core, energy from the leg movements may be lost during the athletic movement. Examples of athletic movements that may benefit from an engaged core include a golf, baseball, tennis, or cricket swing, a throw, a volleyball spike, or a soccer kick. In athletic applications, a sequenced core may provide a number of benefits including: a. Stability and Balance—the engaged core wraps around the torso and hips helping to establish the torso region as a center of gravity; this may keeps the athlete from becoming top heavy during upper body thrusting; and allow for example, a football running back quick side to side movements since weight is not committed to one side or the other; b. Power Transfer—weight shifts from left to right foot as well as hip rotation which may transfer energy from the ground through the feet and legs and up through the core region to the upper body, and finally to the arms and hands may benefit from a sequenced core; c. Protection of the Spine and Torso—injury mitigation due to support of the spine and avoidance of awkward and out-of-control positioning may be encouraged with a sequenced core; and d. Consistency and Repeatability of Athletic Movements—may be increased with a sequenced core that may encourage the athlete to rely less on quick and sometimes jerky movement of the arms and hands to generate power to a movement that includes the larger muscles of the legs and torso to generate power where this power is transferred from the lower body to arms and hands through a sequenced core.

Since engaging the core during an athletic movement requires energy from the athlete, it is critical to incorporate the timing of the engagement into the sequence of the athletic movement. The stiffness provided by the engaged core may be timed appropriately to achieve the maximum benefit.

The use of video recording is very widespread and commonplace with good quality video cameras on smart devices and specialized cameras for athletics and active lifestyle activity video recording. Video feedback of an athlete may be very valuable for numerous reasons including that it allows the observation of subtle movements and changes in position and weight distribution. On the other hand, video recording is quite costly in terms of storage or memory space requirements. When using video as a tool for coaching and athletic performance improvement, care must be taken to reduce storage requirements.

In some sports such as running track, small subtle changes in techniques accumulate over the course of a race. For example, large left to right rotations during the course of a run can slow a runner down and keep them from moving forward at their best speed. A contracted core may reduce the magnitude of such rotations. The core contraction sensor and the movement sensor on the wearable device may be used to record data associated with the core and movements throughout a run. Video recording may be used to monitor form throughout the run. This data may be used after a run to identify changes and areas of improvement. In an embodiment, the wearable device may provide feedback during the run to inform the athlete via buzzing or reporting to a smart watch or other handheld device. In this situation, the athlete may wear the wearable device while a coach controls a camera that records video of the athlete. After the athletic event, in this case which is a run, the athlete and coach may review the technique used and sensor data immediately following the run. This may allow the athlete to try several strategies in a short period of time and record the results, including run times, and data from the worn sensors and video.

During the practice of developing neural patterning to employ a sequenced core to protect qualifying movements, a user may repetitively execute a movement. For example, a user may execute ten stand-sit movements or soccer passes. Data from the wearable device sensors and video recording of the user may be stored in memory. The identification of an unprotected qualifying movement may result from the user failing to engage their core muscles at all during the movement, or from the user engaging their core muscles too late in the movement. When an unprotected qualifying movement is identified, the user may view at regular speed or in slow motion the video of the movement and have displayed at which time their core muscles were engaged if at all during the movement. Algorithm feedback which may include a buzz on the wearable device or an audible or visual feedback from the app, combined with visual feedback from the video may be useful combination of feedback to learning preferred timing of a sequenced core for that movement. In an embodiment, when a protected movement is identified, the video and sensor data associated with that particular repetition of the movement may be discarded while a data outcome may be retained. For example, a piece of data outcome may included the count of the protected movement. Another example of a data outcome may include the time difference between the start of the core contraction and the start of the movement or some other timing relationship between the core contraction and a specific aspect of the movement.

In an embodiment, the recorded core contraction data and video data of the user may be viewed by the user and coach or therapist who may then critique the timing and intensity of the core contraction with respect to the movement and provide immediate feedback and corrective actions to improve coordination of the core engagement during the movement on the next execution.

Generally, individual movements may have a distinct start and a distinct end. Many movements may have substantially continuous movement between the start and end of the movement. Short pauses may occur during some movements. By measuring the duration of pauses and having a priori knowledge of the application, pauses that occur during a movement may be differentiated from pauses that occur before and after a movement. Once the pauses that occur before and after a movement are identified, movements may be isolated. Sensors on the wearable device may be used to identify pauses. For example, when the change in the output of an accelerometer is below a threshold for a specified period of time or when the output of a gyro is below a value for a specified period of time, a pause in the user's movement may be identified for that period of time. When the pause before a movement and a pause following a movement may be identified, then the movement may be isolated and the algorithm may be designed to record or keep data associated with the movement. The start of a movement may be identified by the change in the output of an accelerometer exceeds a threshold or when the output of a gyro exceeds a threshold. The end of a movement may be identified by the slowing of the change in position derived from movement sensor data. Other approaches may be utilized to identify the start and end of a movement. By identifying the start and end of a movement, the amount of data that must be stored may be minimized. In some applications where specific movements that may be identified with the available algorithms may be the critical data to be stored, the video and sensor data around that portion of the movement may be stored, further minimizing the storage requirements. In some applications, the system may record data continuously, and after a start and end of a movement is identified, discard data appropriately to minimize data storage. In this description, storage of sensor data and video data into memory is described. This may be a simplified abstraction since the video file may be stored separately, and in a different format from sensor data. Appropriate programming approaches may be used to resolve any such differences to implement the simplified abstraction. For example, if one takes a one minute video recording, the frame that occurs at the midpoint may coincide with the frame 30 seconds into the recording. This frame may be identified without explicit SMPTE or time-stamping of the video frames. SMPTE timecode contain binary coded decimal in a format hour: minute:second:frame identification for use by users. The model of time stamping or SMPTE may be only an abstraction that may facilitate coordinating video playback and sensor data playback to be coordinated in time. This may allow the application of the embodiments in this description to be used with different recorded video formats.

Figure 1B:
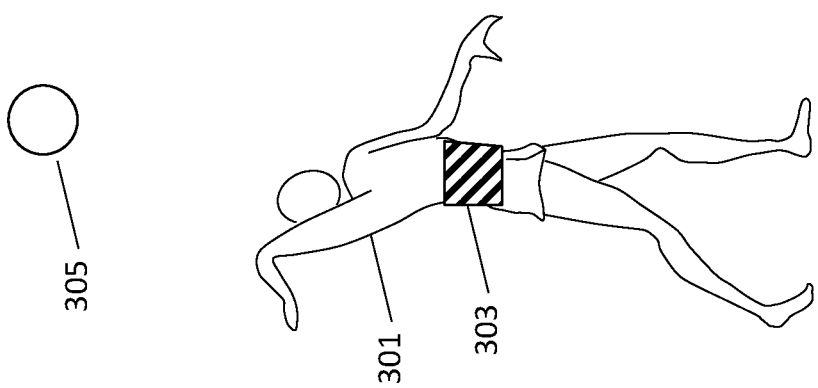
Figure 1C:
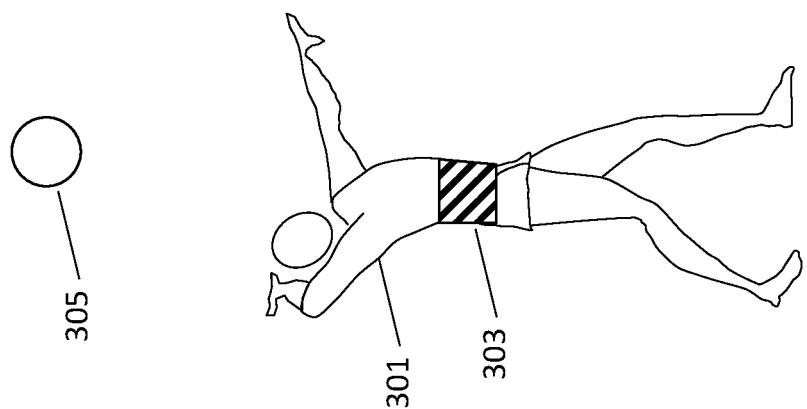

With reference to FIG. 1a-1c, a time sequence of an athlete 301 performing a volleyball serve is shown. Note that as the hips turns counter clockwise while the weight shifts from back (right) foot to front (left) foot, the engaged core 303 indicated by the striped pattern may help to translate this energy from the lower body to the upper body to create momentum and force forward as the palm strikes through the ball 305. The engaged core 303 provides stability and keeps the athlete from twisting as the hand strikes the ball. It also supports transfer of the power from the weight shift forward to the upper body and then the arm and palm. Next, by minimizing twisting at the waist, the lumbar spine is supported throughout the movement. And finally, taken together, the movement will be more repeatable and consistent by reducing torso twisting and generating power from the legs and torso which is transferred to the arm and then palm as opposed to generating power from arm slapping at the ball 305.

Figure 2B:
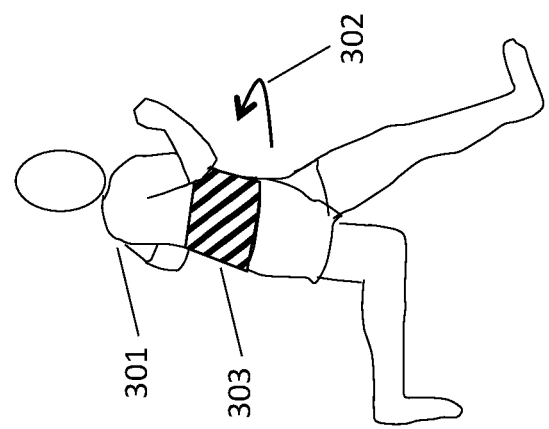
FIGS. 2a and 2b illustrate two strides of a runner.
Figure 2A:
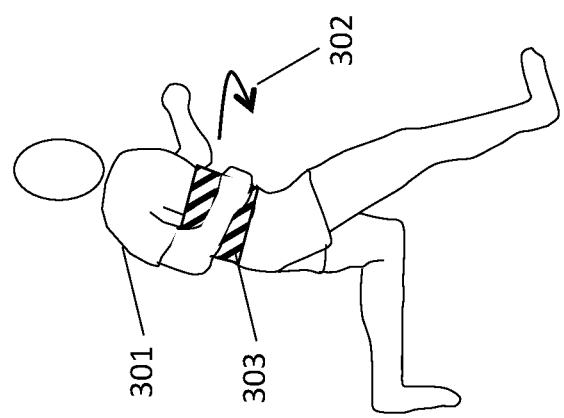

With reference to FIGS. 2a and 2b, a runner 301 is shown before right foot strike in FIG. 2a and before left foot strike in FIG. 2b. For many runners, there is a natural rotation around the torso from stride to stride as indicated by arrows 302. Excessive rotation left and right may slow the runner's movement forward. An engaged core 303 may help to minimize torso rotation. Further, it may support the lumbar spine, resulting on less back pain after running for some runners. Chi running developed by Danny Dreyer is a running technique where the core is utilized for body support.

With reference to FIGS. 3a, 3b, and 3c, the engaged core may be used as part of a soccer ball kick. In FIG. 3a, athlete 301 approaches the soccer ball 305 just before the athlete's left foot strikes the ground. The core may be at this point relaxed, it may be starting to engage, or it may be engaged. In FIG. 3b, with left foot planted on the ground, the athlete 301 may engage core 303 as the right foot swings forward to kick the ball 305. In FIG. 3c, the athlete 301 follows through as the ball 305 is kicked with core still engaged 303. In this case, the contracted core may assist in combining the athlete's 301 forward momentum and torso rotation to propel the right foot forward through the ball 305 before and through impact. The contracted core 303 may support the athlete's 301 lumbar spine throughout the movement of the kick. The contracted core 303 may help the athlete 301 maintain balance through the kick. And through providing balance and increasing efficiency in the kick, the contracted core 303 may increase repeatability and consistency in kicking performance. The use of the core may be applied to other movements in soccer such as passing.

With reference to FIGS. 4a, 4b, and 4c, the engaged core 303 may be part of a golf swing. In this sequence of illustrations, the golfer 301 is performing a golf chipping movement. In FIG. 4a, the golfer 301 is shown at the top of the backswing with club 307 at its highest point with the golfer's 301 core already engaged 303. In FIG. 4b, the golfer 301 is about to strike the ball 305 with club 307 with core still engaged 303. In FIG. 4c, the golfer 301 finishes the swing follow through with the core shown as engaged 303 just before it is relaxed. Some golfers are teaching to engage the core at the start of the golf swing before taking the club 307 back. An engaged core may support the golfer 301 with balance; back support; transfer of energy from the hip turn to the arms, hands, and finally to the golf club head 307, resulting in club head speed and control; and swing repeatability and consistency.

These are a few examples of the advantages and performance improvements that may result from a sequenced core in athletics.

Figure 5C:
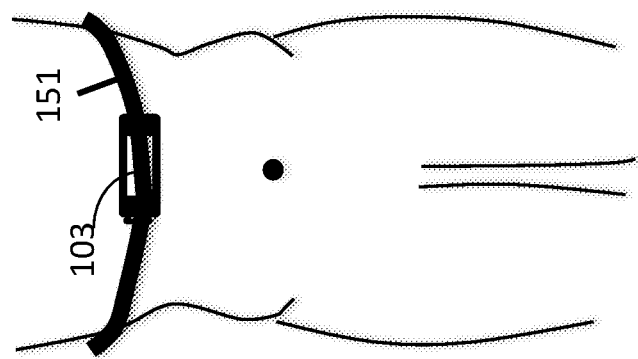
FIGS. 5a-5d illustrate a front view of a user wearing an embodiment of the inventive device worn by a user.
Figure 5B:
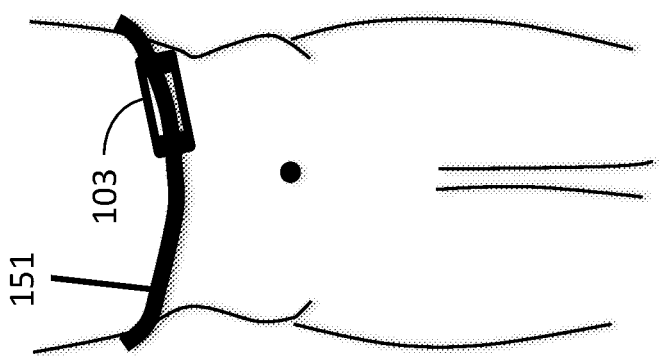
Figure 5A:
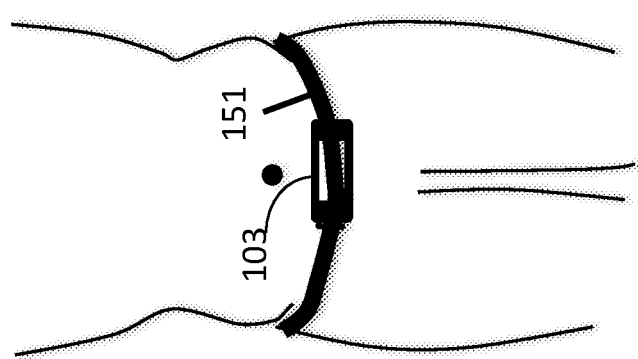
Figure 5E:
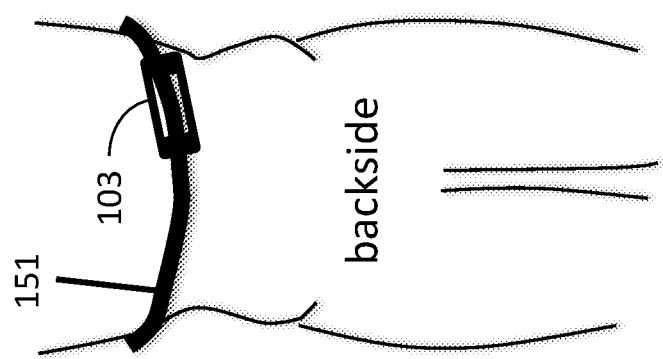
FIG. 5e illustrates a back view of a user wearing an embodiment of the inventive device worn by a user.
Figure 5D:
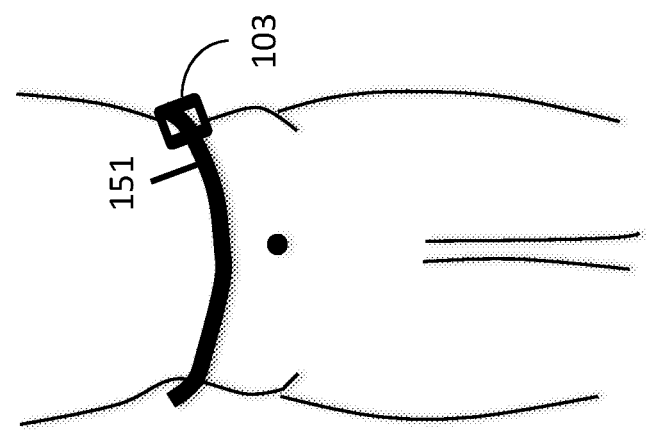

With reference to FIGS. 5a, 5b and 5c, torsos of users are illustrated with core contraction sensors attached to a wearable device 103 with a belt 151 around the torso of the user are illustrated. In FIG. 5a, the wearable device 103 with the core contraction sensor is illustrated below the navel of the user. FIG. 5b illustrates the wearable device 103 with the core contraction sensor below the left ribs of the user and FIG. 5c illustrates wearable device 103 with the core contraction sensor below the solar plexus of the user. FIG. 5d illustrates the wearable device 103 on the side of the user between the ribs and the hip. FIG. 5e illustrates the wearable device 103 on the lower back of the user below the right ribs. The wearable devices described in U.S. Pat. No. 9,226,706 include a core contraction sensor.

Figure 6A:
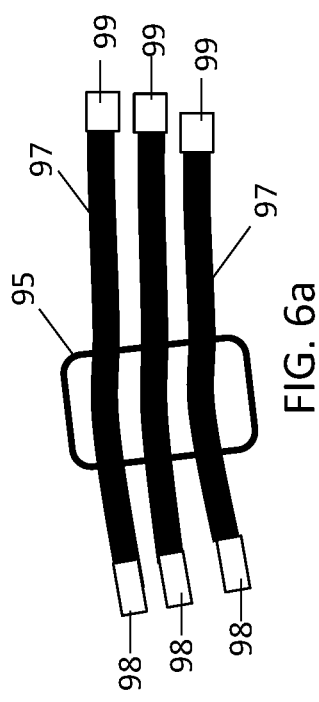
FIG. 6a illustrates an outside view of the strap and belt system for the wearable device to be worn over the VMO.
Figure 6B:
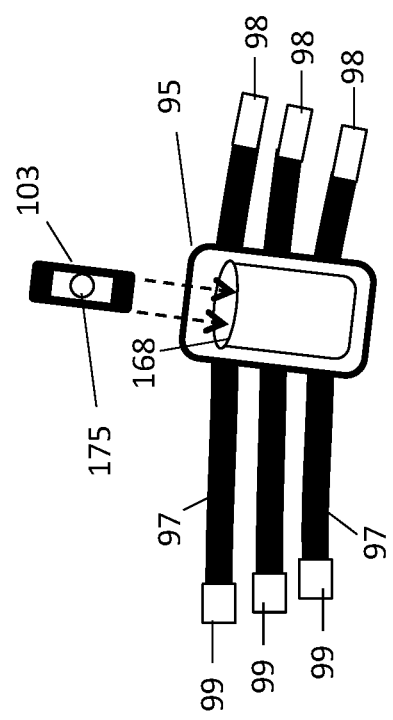
FIG. 6b illustrates the inside view of the strap and belt system and a pocket for the device to slip into.
Figure 7B:
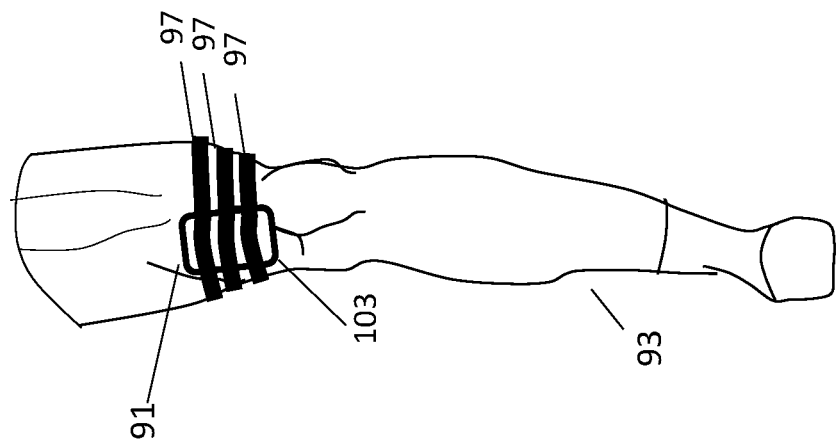
FIG. 7b illustrates the wearable device in a modified strap worn over the VMO.
Figure 7A:
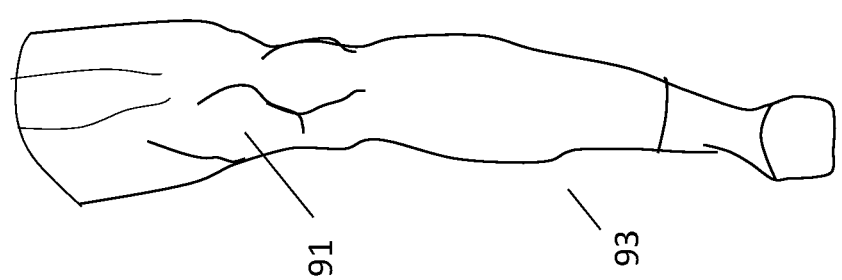
FIG. 7a illustrates the front view of a left leg.

An embodiment is shown in FIG. 6a and FIG. 6b, which includes a sock 95 that can have a pocket 168 that holds the wearable device 103, belt straps 97, interlocking connectors 98, 99, device 103, and contraction sensor bumper 175. This embodiment may be appropriate to monitor the Vastus *Medialis* Oblique (VMO) muscle. The VMO is one of the quadriceps muscles in the front thigh. FIG. 6a illustrates the side worn away from the body and FIG. 6b illustrates the side worn against the body. The wearable device and application software described in this patent application and U.S. patent application Ser. No. 14/132,808 have been described as a device to develop usage of the core muscles. The wearable device and app may be used to monitor other muscles and other body movements. For example, after a knee surgery, the VMO muscle may tend to atrophy. The inventive apparatus and system may be used in a modified strap as shown in FIG. 6a and FIG. 6b that is placed around the thigh and that positions device 103 over the VMO to allow muscle contraction sensor bumper 175 to detect changes in firmness of the VMO as it transitions from a relaxed condition to an engaged condition. Referring to FIG. 7a, a user's left leg 93 is illustrated from the front view. Toward the inside of the left thigh is the VMO 91. FIG. 7b illustrates how the modified straps 97 and the wearable device 103 may be placed around the thigh, and how the device 103 may be positioned over the VMO 91.

As the user changes from the seated position to the standing position, it may be desirable that the user engages the VMO prior to and during the seated to standing movement. The monitoring of the movement of the thigh and contraction of the VMO may performed in a manner similar to monitoring movement of the body and contraction of the core during a qualifying movement. For example, when the user is seated, device 103 in position over the VMO may be substantially parallel to the floor under the user. When the user is standing, device 103 may be substantially perpendicular to the floor. Using a movement sensor in the device 103, this change in orientation of the device may be identified similar to the way a qualifying movement is identified. The contraction sensor may be used to identify an engagement of the VMO muscle instead of the core muscles. The processor in the device may process the signals from the movement sensor and the contraction sensor, evaluate relative timing between the signals from the sensors, and provide feedback to the user to aid in physical therapy, rehab, or muscle and movement training.

Figure 8A:
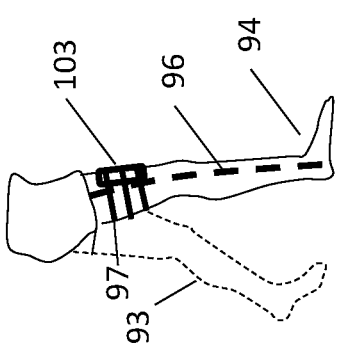
FIG. 8a-8c illustrates the right left stepping forward during a normal gait.
Figure 8B:
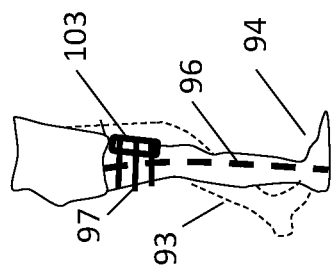
Figure 8C:
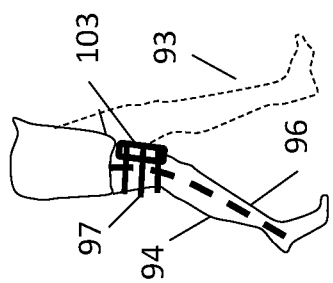
Figure 8D:
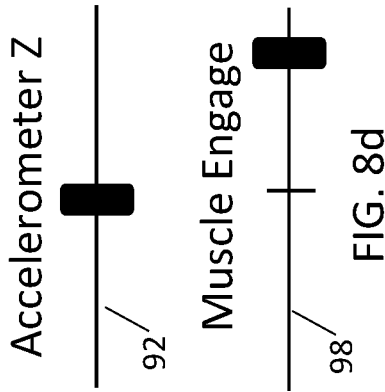
FIG. 8d illustrates an example display showing the output of the muscle contraction sensor and a movement sensor during a normal gait.
Figure 9A:
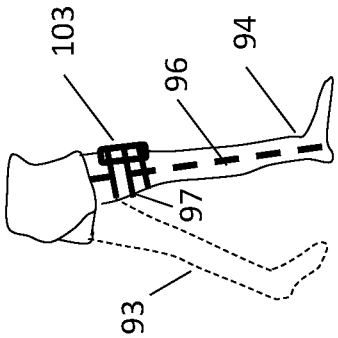
FIG. 9a-9c illustrates the right left stepping forward during an abnormal gait.
Figure 9B:
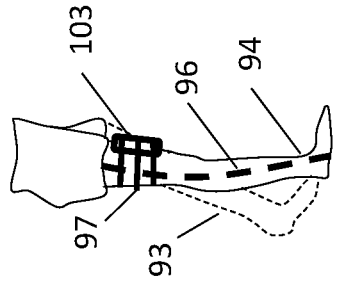
Figure 9C:
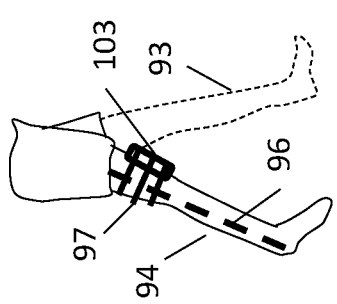
Figure 9D:
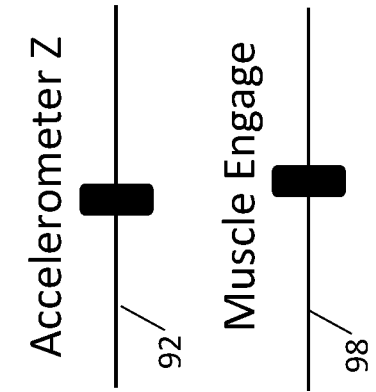
FIG. 9d illustrates an example display showing the output of the muscle contraction sensor and a movement sensor during an abnormal gait.

Referring to FIGS. 8a-8d and FIGS. 9a-9d, an embodiment in which sensor data may be used to differentiate between a preferred movement and unpreferred movement will be described. Knee and body pain is sometimes attributable to locking or hyperextending one's knees during their gait. The right leg step in a normal gait is shown in FIGS. 8a-8c. In FIG. 8a, right leg 94, wearing the device 103 on modified strap 97. The left leg 93 is shown with a dashed line. Leg bend 96 is shown with the thick dashed line illustrating the line from the upper leg (thigh) to the lower leg (calf and shin). Let us define leg bend 96 with the vertex of the leg bend 96 forward as a positive leg bend 96. The position in which the person's weight is over the right leg 94 is shown in FIG. 8b. A slight positive leg bend 96 is shown, indicating a small bend in the knee with the knee slightly forward. After the body rolls over the right leg 94, the right foot is now behind and the left foot has moved forward as shown in FIG. 8c. Wearable device 103 may include an accelerometer as one of the movement sensors. We may define the direction forward as the z-direction. When the user's right leg 94 is perpendicular to the ground as shown in FIG. 8b, the z-direction accelerometer may indicate zero 92 as shown in FIG. 8d. When the user's right leg is stepped forward as shown FIG. 8a, the z-direction accelerometer 92 may indicate a positive value. When the user's right leg is stepped backward as shown in FIG. 8c, the z-direction accelerometer 92 may indicate a negative value. Shown along with the z-direction accelerometer output 92, the muscle engage value from the muscle engage sensor output 98 (also the core contraction sensor) may also be shown as illustrated in FIG. 8d. The data shown FIG. 8d is the data from the leg being in the position shown in FIG. 8b. The z-direction accelerometer output 92 indicates the device and thigh being perpendicular to the ground, and a large positive value on the muscle engage sensor output 98 shows that the VMO is engaged. This combination of near zero value of z-direction accelerometer output 92 and large positive value on the muscle engage sensor output 98 may occur during a preferred gait. This example of an unpreferred gait is shown in FIGS. 9a-9c. In the abnormal gait involving hyperextension of the knee, the knee joint moves past its normal range of motion, opposite to the walking direction. Further, the knee may lock in this hyperextended position while the person transfers weight over this locked leg and forward. This may cause knee pain as well as knee instability. The right step forward with this unpreferred gait is shown in FIG. 9a. Leg bend 96 is shown slightly negative, indicating the knee beginning hyperextension. In FIG. 9b, the right thigh is in its most upright position with a majority of the body weight on the right leg 94. The leg bend 96 is clearly negative and the knee is in hyperextension. The person then rolls their body weight over the right foot as the left foot strides forward as shown in FIG. 9c. In FIG. 9d, the z-direction accelerometer 92 and muscle engage sensor 98 are shown associated with the leg position in FIG. 9b. Similar to FIG. 8d, the z-direction accelerometer indicates a near zero value due to the position of the wearable device 103 at that instant. However, unlike the muscle engage sensor 98 of FIG. 8d being at a positive peak value, the muscle engage sensor 98 of FIG. 9d is near zero. Since the weight is being supported by the locked knee, the muscles in the thigh do not strongly engage.

By monitoring the timing of contraction of the VMO relative to movements identified by the movement sensor, a correct step may be identified by a peak in the muscle contraction sensor as the movement sensor detects that the device is substantially horizontal as the body rolls over the leg being monitored. An incorrect step involving a hyperextended knee may be identified by little or no peak during the same instant as the movement sensor detects that the device is substantially horizontal as the body rolls over the leg being monitored. The peak of the muscle contraction sensor may occur at a different moment in the gait. The magnitude of the muscle contraction sensor peak may also be much less than the magnitude of the muscle contraction sensor peak during a correct step. In some embodiments, the system may be used to detect a muscle or core contraction before or during a movement. In another embodiment, the system may be used to detect a preferred execution of a movement and an unpreferred execution of a movement based on the timing relationship between movement sensor data signals and the muscle contraction (or core contraction) sensor data signal.

Figure 10B:
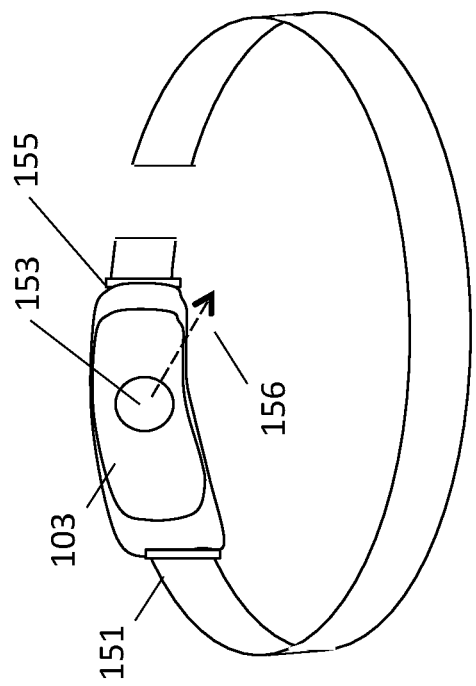
FIG. 10b illustrates an embodiment of a core sensor interface and a wearable device attached to a strap coupled to a belt.
Figure 10A:
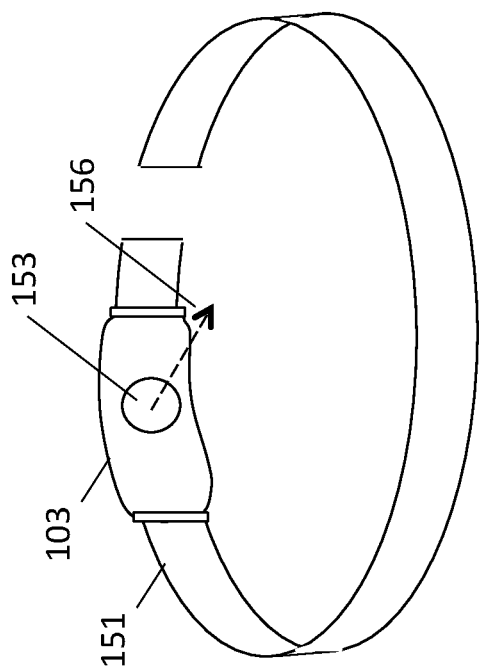
FIG. 10a illustrates an embodiment of a core sensor interface and a wearable device attached to a belt.

An embodiment of the wearable device is shown in FIG. 10a including a core sensor interface 153, device 103, and belt 151. This embodiment may be appropriate to monitor the core muscles. The core sensor interface 153 may couple to the user's core muscles in the direction shown by the arrow 156. The device 103 may include a printed circuit board (PCB) and may contain sensors, a processor, power management electronics, communication electronics, and a battery. The belt 151 may be adjustable in length. In an embodiment, the belt 151 may have at least a portion of a length that is elastic. In another embodiment, the belt 151 may be substantially elastic. In another embodiment, the belt 151 may have no portion that is elastic.

Details of the sensor interface 153 will depend on the specific type or types of sensors used to monitor the core muscles. Some users may have core muscles that are more developed while others may have core muscles that are less developed. Some users may have more body fat over the core muscles while others may have less body fat over the core muscles. In an embodiment, the sensor interface 153 may extrude from the face of the device 103 and may be referred to as a bumper. In an embodiment, the bumper may couple to the core muscles. In an embodiment, the bumper may have a variable height to accommodate variations from user to user in the amount of body fat over the core muscles as well as differing amounts of core muscle development. In an embodiment, the bumper may couple to the user's core muscles in the target core sensing area. The inner core muscles generally co-contract, meaning the muscles contract together. While the target core sensing area is an attractive location for attaching the wearable device 103, other locations may be utilized. For example, when the transversus abdominus contracts, the diaphragm may also contract. In an embodiment, the location of the solarplexus below the lungs, between the ribs, and above the abdominal section may be used as the attachment location of the wearable 103.

Another embodiment of a wearable device is shown in FIG. 10b. The primary difference compared with the embodiment shown in FIG. 10a is the device is attached to an additional element we may refer to as a strap 155. The strap may then connect to the belt 151. The strap 155 may bring benefits to the inventive system that will be described later. Some embodiments of the wearable device 103 may be attached with a belt with a means to control a variable length of the belt 151. Fitting the wearable device may include modifying the adjustable elements to achieve a preferred combination of sensitivity and comfort.

As described in U.S. Pat. No. 9,226,706, a number of technologies may be used in core sensing to identify a core contraction. For example, a force sensor or pressure sensor may be used. By applying pressure to a device attached against the core muscles, engagement or contraction of the core muscles may result in a pressure change on the device which may be detected by a force sensor or pressure sensor. An embodiment of the device utilizing a force sensor is shown in FIGS. 11a-11f. In another embodiment, movement sensors may be utilized to detect movements associated contraction of the core muscles. In another embodiment, electromyography or EMG or other sensing techniques utilizing similar principles may be utilized. Electrical current flows into a muscle in order to contract the muscle, and this current may be detected with electrical sensors. The current may be detected by measuring a voltage difference between two points on the skin. In an embodiment of EMG, fine needles may be placed into the muscles being tested. The use of needles directly into the muscles may be more accurate than monitoring the muscles from the surface of the skin. However, needles are quite intrusive for a system that may be used in a variety of settings and by users with little training on how to attach and remove needles. An embodiment of the device utilizing voltage sensing or principles of EMG using sensing on the skin is shown in FIGS. 12a-12c. In another embodiment, the principles of backscattering may be used. In backscattering, a source signal is transmitted by a transmitter and the reflection of the signal back in the direction from which it was transmitted is measured by a receiver. When the core muscles are contracted, blood flows to the muscles, resulting in changes in the reflected signal. These changes may be identified and associated with core muscle contraction. A number of different types of signals may be used. For example, ultrasound, infrared, and electromagnetic energy may be used. An embodiment of the device utilizing backscattering is shown in FIGS. 13a-13c. In other embodiments, other sensing technologies may be used. Appropriate modifications may be needed to the system to accommodate specific details associated with the implementation of different techniques and technologies.

An example of the system utilizing a force sensor in the form of a force sensing resistor or FSR is shown in FIGS. 11a-11f and will now be examined in more detail. The side view of the device 103 is shown in FIG. 11a, the front view of the device 103 which is the side of the device which will press up against the user's core enabling the core sensor interface 153 to couple to the user's core is shown in FIG. 11b. The top view of the device is shown in FIG. 11c. The curve shown in FIG. 11c may have varying degrees of curvature in different embodiments. In an embodiment, device 103 may have a bendable structure. In an embodiment of the bendable structure, the device may be substantially continuously bendable. In another embodiment, the device may bend in bendable locations. For example, the device may have three sections and bend in the locations between sections. In another embodiment, there may be no curvature. The device may have a cavity 152 to house sensors, electronics, a battery and other components. In FIG. 11d, both sides of the device are shown connected to a belt 151. There are number of ways to connect the belt to the device. For example, there may be pass through slits in the device 157 to allow the belt 151 to pass through and connect back to itself as shown in FIG. 11e. The belt 151 may connect back to itself using, for example, magnets, clips, snaps, Velcro, or some other fastener. The device 103 may also connect to a strap 155 and the strap 155 may connect to the belt. The strap may be made from a bendable and soft material, or it may be made from a hard material like plastic. Alternatively, it may be made out of a combination of materials. For example, the device 103 may snap into a plastic element that is overmolded by a rubber or other bendable material. Many combinations are possible and may be utilized to meet the requirements of different applications.

Referring to FIGS. 12a-12c, an embodiment of the device utilizing EMG for the core sensor is shown. Since a potential difference between two nodes may be measured, two conductive ports Node A 161 and Node B 163 may be utilized. A top view of an embodiment shown in FIG. 12b shows Node A 161 and Node B 163 as conductive ports embedded in the surface of the device 103. An embodiment shown in FIG. 12c shows Node A 161 and Node B 163 as bumpers extruding from the face of the device. In an embodiment, the bumpers are fully conductive. In another embodiment, the bumpers are partially conductive. For example, the bumpers may be conductive at or near the tips of the bumpers and these conductive tips may connect to a conductive section that may connect to electronics within the device. An example of bumpers with conductive tips attached to a conductive center 164 are shown in FIG. 12c.

Referring to FIGS. 13a-13c, an embodiment of the device 103 utilizing backscattering for the core sensor is shown. Backscattering utilizes at least one transmitter 165 and at least one receiver 167. Both are shown as independent ports 165, 167 in FIGS. 13a and 13b. It is shown as a single port 153 in FIG. 13c, with both transmitter and receiver combined in a single bumper. The transmitter signal may be audible, for example ultrasound; light, for example infrared; radio frequency or RF; or some other readily creatable signal that may backscatter differently when core muscles are relaxed and contracted. The design of the bumpers may be optimized for the nature of the signals being used.

Figure 14:
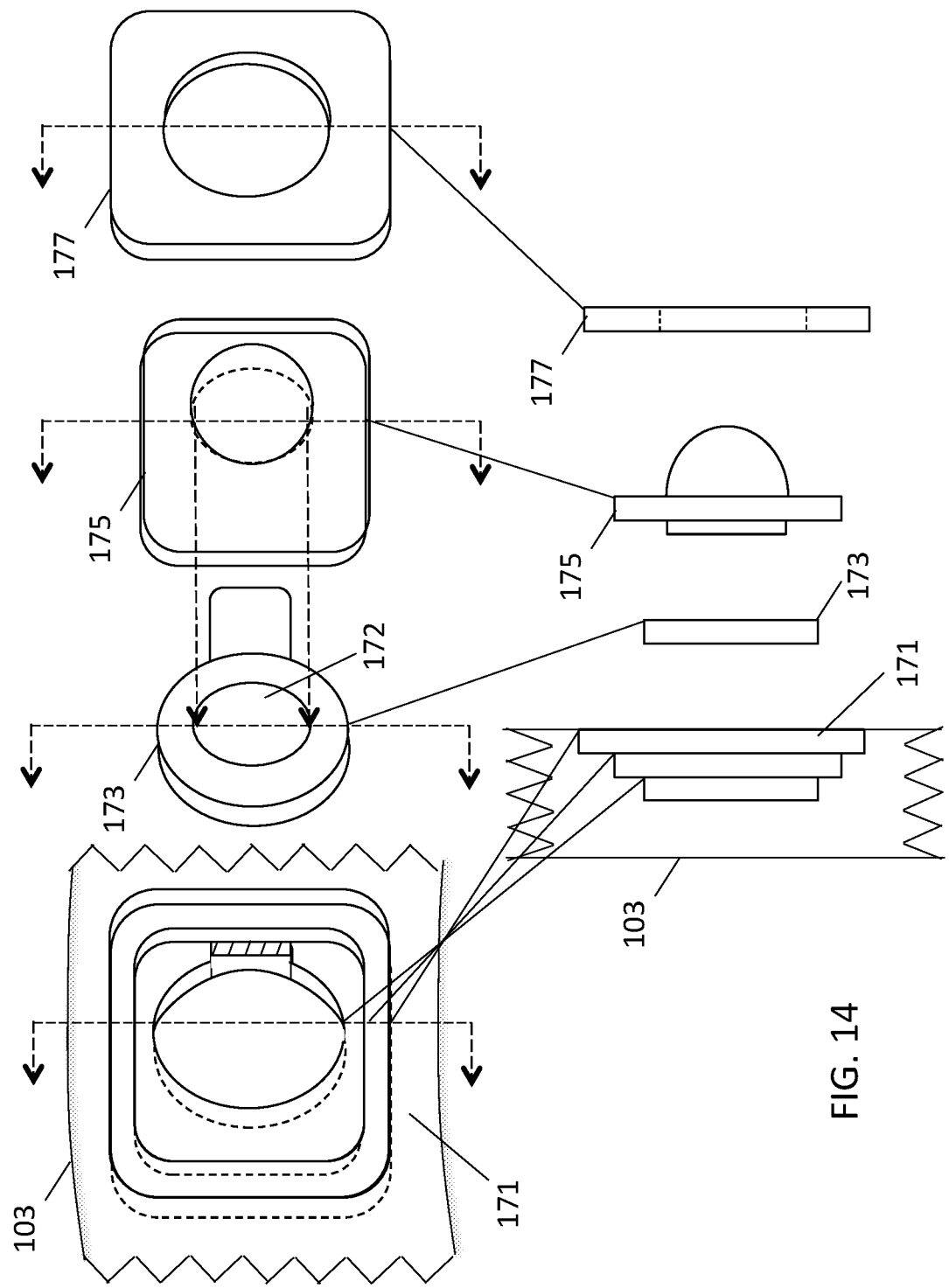
FIG. 14 illustrates an exploded view and a cross-sectional view of an embodiment of a core contraction sensor assembly.

Referring to FIG. 14, an exploded view of an embodiment utilizing an FSR 173 is shown on the top of the figure while a cross-sectional view is shown at the bottom of the figure. Starting at the upper left and moving to the right, the exploded view includes the device 103 with volume removed 171 to custom fit a force sensing resistor 173 with active area 172, a bumper 175 that may be implemented with a rubber or rubber-like material with a brim, and a frame 177 that holds the force sensing resistor or FSR 173 and bumper 175 in place by holding the brim in place. The frame 177 may be attached to the device using glue or one or more screws or other attachment materials. Additional features may be designed into the brim of the bumper including an O-ring in order to promote water resistance in the design. In the cross-sectional view, the deepest cavity is where the FSR 173 may reside. Above the cavity for the FSR 173 is a cavity where the brim of the bumper 175 may reside. Above the bumper brim is a cavity to fit the frame 177. Note in the cross-sectional view that the bumper 175 may have a small extrusion underneath it to interface to the active portion of the FSR 173. In an embodiment, the feature of the bumper 175 that interfaces to the user's 103 core may be shaped to achieve the objectives of comfort and sensitivity. In the example shown, the section of the bumper that will interface to the user's core is shown to be rounded. In an embodiment, the bumper may have a substantially flat area on the tip that interfaces to the user's core muscles while having a rounded top rim.

Figure 15B:
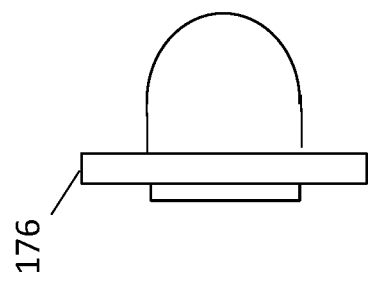
FIG. 15b illustrates an embodiment of a bumper with a second height.
Figure 15A:
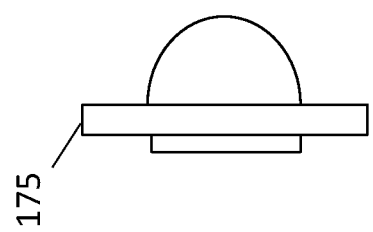
FIG. 15a illustrates an embodiment of a bumper with a first height.

Referring to FIGS. 15a and 15b, an embodiment may have bumpers with differing height to accommodate the body types of different users. A user with more body fat may benefit from a longer or taller bumper 176 as shown in FIG. 15b compared with the shorter bumper 175 shown in FIG. 15a.

Referring to FIG. 16a, an embodiment of an extender cap 181 which may be added to the top of the bumper 175 to further extend the effective height of the bumper 175. In FIG. 16b, an angled view is shown to further illustrate the extender cap 181 design to extend the effective height of the bumper. A side view of the cap 181 sitting on the bumper 175 is shown in FIG. 16c. In an embodiment, different sized caps 181 may be used to provide further variability in order to achieve greater measurement sensitivity while maintaining user 101 comfort. Different techniques may be used to attach a cap to the bumper. For example, the cap 181 may be sized to snuggly fit over the bumper 175 requiring no additional material or elements. Adhesive or double stick tape may be used to connect the cap 181 to the bumper 175. An additional extrusion may be designed into the bottom of the cap 181 to fit into an additional cavity in the bumper 175 as shown in FIG. 16d to provide additional stability for the combined structure including the cap 181 and bumper 175 as shown in FIG. 16e.

A device 103 with a small sized bumper 175 is shown in FIGS. 17a and 17b. In FIG. 17a, a depiction of a user with less body fat 148 is shown and in FIG. 17b, a depiction of a user with more body fat 148 is shown. In FIG. 17a, the bumper 175 is near the core muscles whereas the bumper 175 is shown to be far from the core muscles in FIG. 17b. In FIG. 17c, a taller bumper 175 with a cap 181 is shown with the depiction of the user with more body fat 148. Note that the larger bumper 175 and additional cap 181 enables the sensor interface 153 to reach deeper and nearer to the core muscles.

Referring to FIG. 18a, a condition is shown where a user with a small amount of body fat also has prominent hip bones 154. When the belt 151 is used to hold the device 103 near the body, the belt 151 rests on the hip bones 154 which keeps the device 103 a distance away from the core so the bumper 175 is not able to properly contact the target core sensing area. Referring to FIG. 18b, a conceptual solution is proposed. With belt 151 effectively sitting on the prominent hip bones 154, conceptual adjoining line 55 connects the right and left side belt segments. Conceptually, the inventive solution enables the device 103 to move away from the adjoining line 55 and toward the body as indicated by the arrows 57. Using this approach, the gap between the adjoining line 55 and the target core sensing area may be filled. In FIG. 18c, a strap 155 is introduced to continue the adjoining line between the belt segments and the device is attached to the strap 155 via connecting structures referred to as gap extenders 158. Introduction of the strap 155 and gap extenders 158 enables a gap filler 159 to be added between the device 103 and strap 155, which has the effect of pushing the device 103 and subsequently, the bumper 175 toward the user's core muscles as shown in FIG. 18d. The gap filler 159 may be made of different types of material, depending on the design choices of the other components. For example, the gap filler 159 may be made of rubber or plastic or an additional appropriate material or materials. The gap filler 159 may be attached using connectors such as clips, Velcro, magnets, snaps, or other attachment techniques such as tongue-in-groove structures.

An embodiment showing all connections of the inventive device packaging is shown from top view in FIG. 19a and shown from the front in FIG. 19b. Slits 167 are cut out of strap 155 to allow the belt 151 to loop through the slits 167 and connect back to itself. It may be sewed to itself, connected by Velcro, or attached by a number of other attachment methods. Slits 167 may be seen in FIG. 19b, while the looping back of the belt to connect to itself is shown in FIG. 19a. The gap extender 158 may be a thin, light, and bendable material which starting from the left side may be attached 161 to the strap 155, pass through slit 157 in the device, pass around between the device 103 and the strap 155, then back through the slit 157 on the right side, and attach on the right side to the strap 155 at location 161 on the right side of the device shown in FIG. 19b. In an embodiment, a very thin material is used for the gap extender 158 to minimize its contribution to thickness between the device 103 and strap 155, and to keep it from keeping the ends of device 103 from contacting the user's core section. In FIG. 19b, the connecting structure 158 is drawn for illustrative purposes thicker than may be desired. In an embodiment, the gap extender 158 may be elastic or partially elastic. In an embodiment, the gap extender 158 may be made of the same or similar material to the strap 155.

In applications where the bumper makes direct contact to a user's skin or to certain materials of clothing, the bumper may stick or grab on to the user's 101 skin or clothing for some angles and amounts of pressure. Referring to FIGS. 19c and 19d, a soft buffer material 162 resistant to sticking or grabbing may be placed over the location where the bumper couples to the user's 101 core muscles. In an embodiment, the stick resistant buffer material 162 may be cotton, polyester, nylon, microfiber or other material, or may be made from a blend of different types of materials. A number of materials are being used and developed for high performance athletic apparel. These materials may be appropriate for stick resistant buffer material 162. In an embodiment, the stick resistant buffer material 162 may be a type or combinations of types of rubber. In an embodiment, buffer material 162 may be manufactured into the bumper 175 via a surface layer that may be resistant to sticking or grabbing.

Several implementations may be used to hold the buffer material in place. For example, the buffer material 162 may be designed into a tubular shape that slips over the device 103 or portions of or all of the strap 155 which may include the gap extender 158. FIG. 19c shows an example of a tubular shape forming a stick resistant sock 162 to the right of the wearable 103 before it is slipped over the device 103. FIG. 19d shows the stick resistant sock 162 in position over the bumper. In an embodiment, the buffer material 162 may be made from a stretchable material, allowing it to stretch to accommodate different bumper heights. In another embodiment, the buffer material may be made from a material or materials with water resistant qualities. In an embodiment, the stick resistant sock 162 may be made from a material or materials with water resistant qualities, and designed to fit snuggly on both ends over the wearable device 103 as shown in FIG. 19d. The snug fit on the ends of sock 162 may be implemented in a number of ways. An embodiment may utilize a material that stretches. Making the entire sock 162 with stretchable material and designing said sock to fit snugly may result in snug ends when the sock 162 is on the device 103 and the stretchable material may stretch over the bumper to accommodate different bumper heights. Another embodiment may utilize elastic or a material with qualities of elastic that are sewn in or attached to the ends of the sock. Another embodiment may utilize rubber or a material with qualities of soft bendable rubber that may be molded to fit over the device 103, fit snugly on the ends, and have a stretchable area over the bumper or designed with extra volume to accommodate different bumper heights. By combining a design in which all openings to the cavities of the device fit within or under the coverage of the stick resistant sock 162, and making the sock 162 from a material or materials with water resistant qualities with a snug fit on the ends, the combined structure including the device and stick resistant sock 162 may be substantially splash proof from water or other liquids including a user's perspiration. In said design, the strap 155 may have design features to support keeping the sock 162 in position over the device. In an embodiment, the stick resistant sock 162 may be made from a low-cost water resistant material and be designed for a limited number uses and be disposable for certain applications. For example, after using the wearable device with a user during a therapy session, the therapist 107 may remove a limited use and disposable stick resistant sock 162 and put on a new sock 162 for a next user.

Figure 19E:
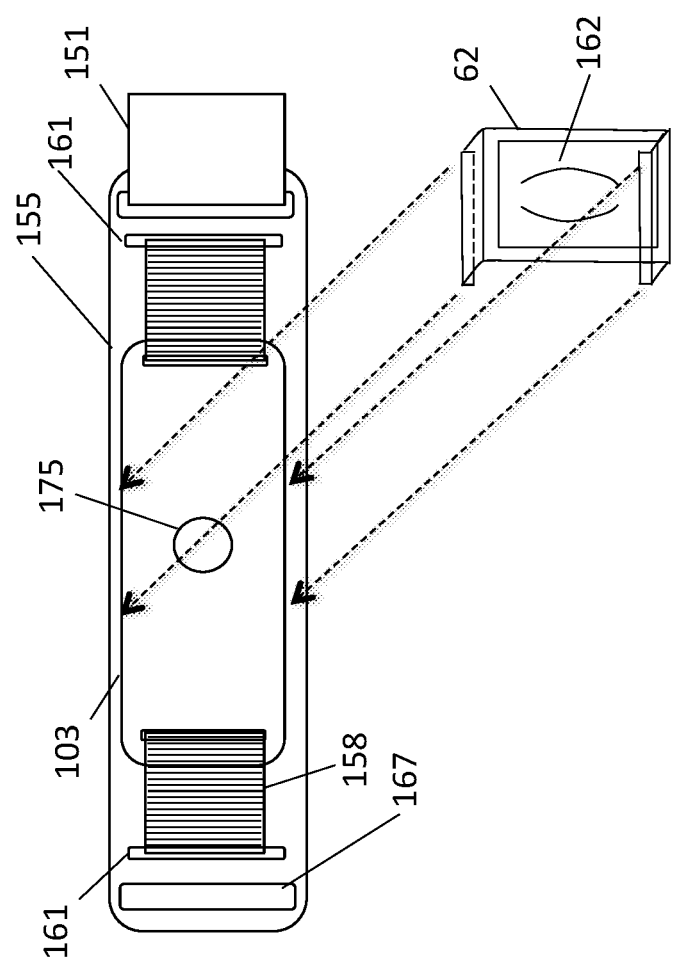
FIG. 19e illustrates an additional element that may snap or clamp onto the face of the device in order to hold material over the bumper.

In other embodiments, the buffer material 162 may be fitted onto an additional element 62 that may snap or clamp on over the face of the device, allowing the bumper 175 to be covered by the buffer material 162 as shown in FIG. 19e. Element 62 may be made out of metal, plastic, or other firm and bendable material. Buffer material 162 may be attached to element 62 using glue, thread (sewed on), or other attachment techniques or materials. In these embodiments, use of water resistant materials for the buffer material 162 and appropriate placement of the element 62 over the device openings may combine to result in a splash resistant wearable device 103. Openings into the device may include an opening to place the PCB, battery, and sensors which may be covered with a fitted cover and held in place by one or more screws, glue, or other attachment devices or materials; ports for battery charging; a communications interface connector which may additionally support battery charging such as USB; and a sensor interface port which may be covered by a frame and held in place by one or more screws, glue, or other attachment devices or materials.

The inventive sock 162 is an example of a buffer that may be used between the bumper and the user's core. Design elements of the buffer as described may be applied to other implementations to achieve similar objectives. A summary of key design element of the inventive sock 162 may include: a. provides stick or grab resistance between the bumper and the user's skin or clothing; b. with appropriate design of the sock 162 and device 103, the combination may be splash proof; furthermore, the strap 155 and gap extender 158 may be designed to support maintaining the sock 162 in position over the device; c. accommodates different bumper heights or may be designed to fit certain ranges of bumper heights; d. can be made with relatively low material and manufacturing cost and using plastic wrap or thin rubber material may be made disposable; e. may be made from materials used in high performance athletic apparel and may be washed and re-used; and f simple to remove and replace so may be used by a therapist for multiple users and a new or clean sock 162 may be put on for the start of each user session.

In FIG. 20a, an alternative embodiment to extender cap is illustrated that is similar to the extender cap 181 shown in FIGS. 16a-16e. The extender cap may increase both height and girth of the bumper. Mushroom cap 193 is similar to extender cap with the feature that the height of the bumper may not be appreciably increased. In an embodiment, the mushroom cap 193 increases the girth but not the height of the bumper. The mushroom cap 193 may result in greater comfort to the user by reducing the sharpness of the bumper. In an embodiment, a flat ring 191 may be placed around the bumper on the face of the wearable device. The ring 191 may keep the mushroom cap 193 from pressing down into the face of the wearable device 103 when pressure is placed on the mushroom cap 193. In an embodiment, the ring 191 may be made from a firm pliable material such as felt, neoprene, or material with similar properties. In some applications, an extender feature may be added to the top of the mushroom cap 191 and bumper 175 in order to increase the height of the contraction sensor. In an embodiment, this feature may be an extender disc 195 as illustrated in the figure. The ring 191, mushroom cap 193, and extender disc 195 can have circular outer circumferences. The ring 191 and mushroom cap 193 can have circular inner diameter center holes. FIG. 20b illustrates the ring 191 and mushroom cap 193 placed around and on the bumper 175. Extender disc 195 is shown sitting on top of mushroom cap 193. The mushroom cap 193 may be held in place via a snug fit or with an adhesive such as glue, double stick tape, or other adhesive. Extender disc 195 may be attached using an adhesive such as glue, double stick tape, or other adhesive. In an embodiment, additional features may be designed into the components to facilitate attaching the extender disc 195 or extension feature to the mushroom cap 193.

Figure 21A:
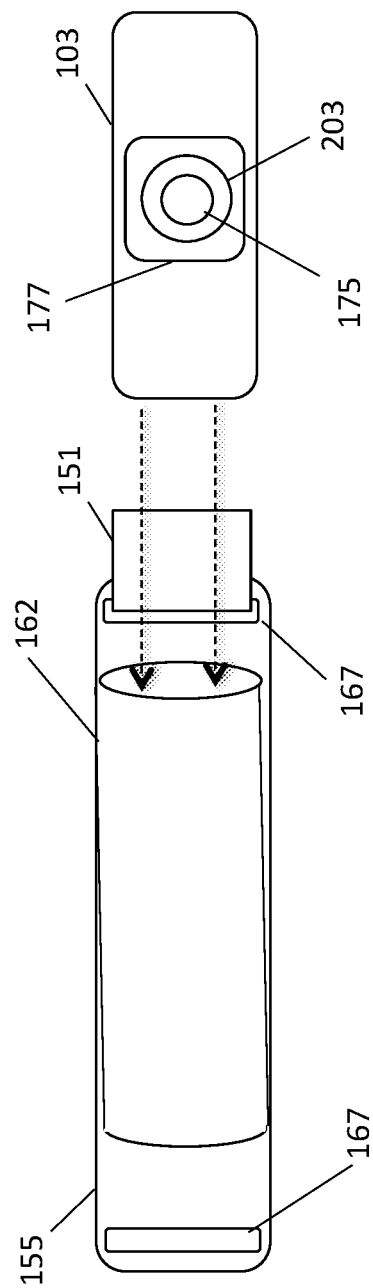
FIG. 21a illustrates a sock attached directly to the strap allowing the device to be easily slipped into and out of the sock.
Figure 21B:
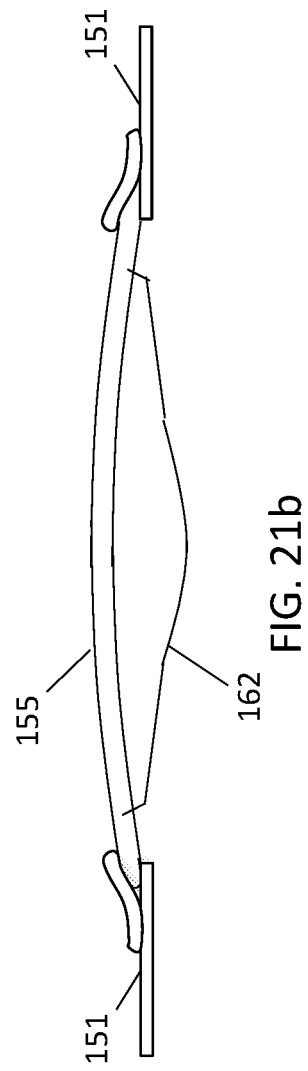
FIG. 21b illustrates a top view of the device sitting in the sock, attached to the strap and belt.

In FIG. 21a, an embodiment with sock 162 attached directly to the strap 155 is shown. Device 103 simply may be slipped into sock 162 with no additional strapping or connecting steps required. Sock 162 may provide splash proof qualities, while providing the buffer role between the device 103 and the user's body or clothing. FIG. 21b illustrates a top view of the device 103 sitting in the sock 162 attached to the strap 155. The sock 162 may be attached to the strap 155 by sewing, gluing, Velcro, magnets, or other means of securing or attaching.

Figure 22:
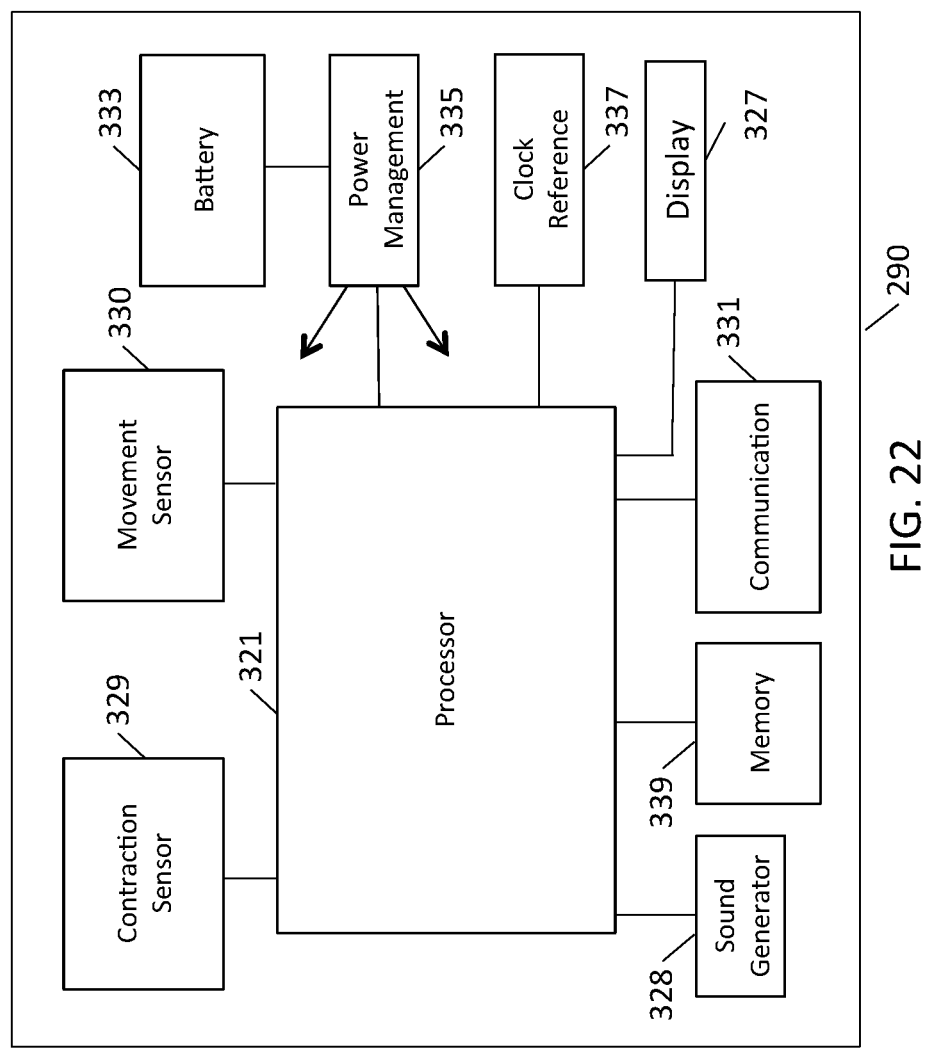
FIG. 22 illustrates a block diagram of the wearable device.

With reference to FIG. 22, a block diagram of an embodiment of the wearable device 290 is illustrated. The processor 321 can also be coupled to various output devices which can provide information to the user which can include one or more of: a sound generator 328 which can emit output signals to the user that indicating correct core contractions during musical tones/notes or incorrect core contractions. In different embodiments, different output devices can be selected. For example, a buzzer or sound generator 328 can be useful at home, but these audio output devices may not be appropriate at an office where other employees will hear the output sounds. An output device such as a light or visual output can be a visual display 327 such as a touch screen which may be useful providing core contraction, music information and feedback to users in areas where others noise can be disruptive to others.

The processor 321 can also be coupled to a communications device 331 that can transmit information to other devices through a wired or wireless communications connection, for example the communications device 331 can be a Bluetooth device that provides wireless communications to other devices. A battery 333 can be coupled to a power management module 335 which can control the distribution of electrical power to the system components. The battery 333 can be rechargeable and capable of being charged with a charger. The processor 321 can also be coupled to a memory 339 which can store musical tone and note information and record user core contraction data. The system can also include a clock reference 337 which can provide a system reference clock to the processor which may also be used to derive sampling clocks for the core contraction sensor 329. If the system has a minimum of intermittent access to date and time information, for example through a cellular system, the clock reference 337 may be utilized in an algorithm using such date and time information so that recorded movements and core contractions can be stored with time stamps.

When a user engages or contracts a muscle, the surface skin region over the muscle being engaged may become firm to the touch and less compressible. When the wearable device is placed on a belt over a muscle that transitions from relaxed to engaged, the change in firmness as the muscle transitions from relaxed to contracted may result in an increase in pressure on the contraction sensor and result in an increase in the contraction sensor value. If a user engages their core muscles employing the technique of hollowing, the contraction sensor value may decrease. Users that utilize the technique of bracing may also have the contraction sensor value decrease when their core is engaged due to body composition and the manner in which they engage their core muscles. In the following, we will assume that when a user engages their core muscles or other muscle being monitored by the wearable device, the contraction sensor value increases. The algorithms may be modified to accommodate the contraction sensor value decreasing when the core muscles or other muscles being monitored are engaged.

The performance of core engagement identification algorithm is critical to the user experience with the wearable device. Let us now investigate some of the important considerations and some inventive embodiments. False positive core engagement identification and missed valid core engagements may be found frustrating to a user and negatively impact the user experience. The inventive approaches described may reduce the frequency that false positives and missed valid core engagements occur.

Figure 23:
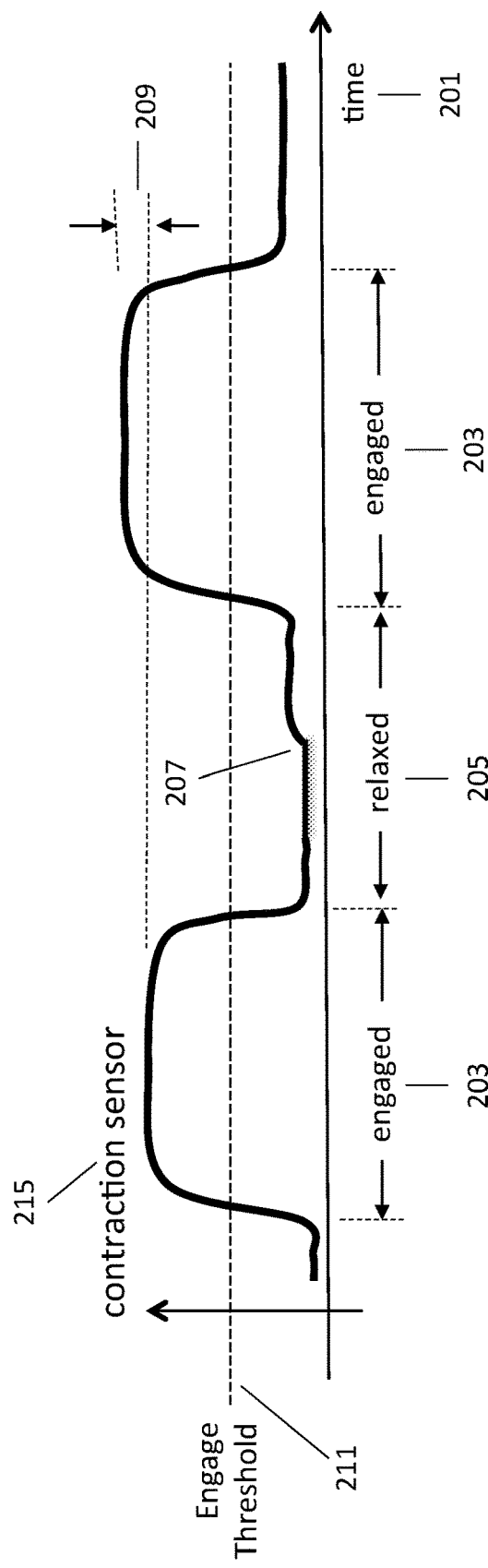
FIG. 23 illustrates features of a signal received from a contraction sensor.

An example of the signal received from the contraction sensor 215 (vertical Y-axis) over time 201 (horizontal X-axis) is shown in FIG. 23. In the example shown, when the user engages the core muscles, the contraction sensor value increases. A sequence of the user's core transitioning from the conditions of engaged 203, to relaxed 205, followed by engaged 203 is shown. In the middle of the relaxed period 205, a small change 207 in the contraction sensor value is shown. This may be the result of the user changing their body position while keeping their core relaxed. This change in body position may change the incident pressure on the contraction sensor which equivalently is the contraction sensor bumper. Highlighted in the illustration is the change from the first engaged value to the second 209. This change may result from at least two sources. First, this may be due to a change in core engagement intensity from engagement to engagement. Second, it may be due to different incident pressures of the body on the contraction sensor due to the first engagement being performed in one position, for example sitting, to a second position, for example, standing.

In an embodiment, the Engage Threshold 211 is the level which may define the engaged or relaxed condition. If the contraction sensor value equals or exceeds the Engage Threshold 211, the core may be identified by the algorithm to be engaged. If the contraction sensor value is less than the Engage Threshold 211, the core may be identified by the algorithm to be relaxed. In the illustration of FIG. 23, Engage Threshold 211 is a constant fixed value. The Engage Threshold 211 can be an output signal from the core contraction sensor which can be an electrical resistance value from an FSR. In other embodiments, the Engage Threshold 211 can be any other metric which corresponds to core contraction value such as a digital, force, electrical, pressure, etc. that can be detected or output by the contraction sensor.

Due to the variation in relaxed values due to different body positions and varying belt tightness, the fixed threshold may on the one hand result in false positive core engagement identification, or on the other hand, make difficult getting an engaged core to trigger a core engagement identification. For example, a body movement may result in a larger incident pressure on the contraction sensor moving the relaxed value close to the threshold. As a result, body movements may increase the contraction sensor value above Engage Threshold 211, creating a "false positive" core contraction identification. In another example, with a relaxed core, if a user moves in such a way to decrease pressure on the contraction sensor, then when the user engages their core muscles, the resulting contraction sensor value may be insufficient to exceed Engage Threshold 211.

Figure 24:
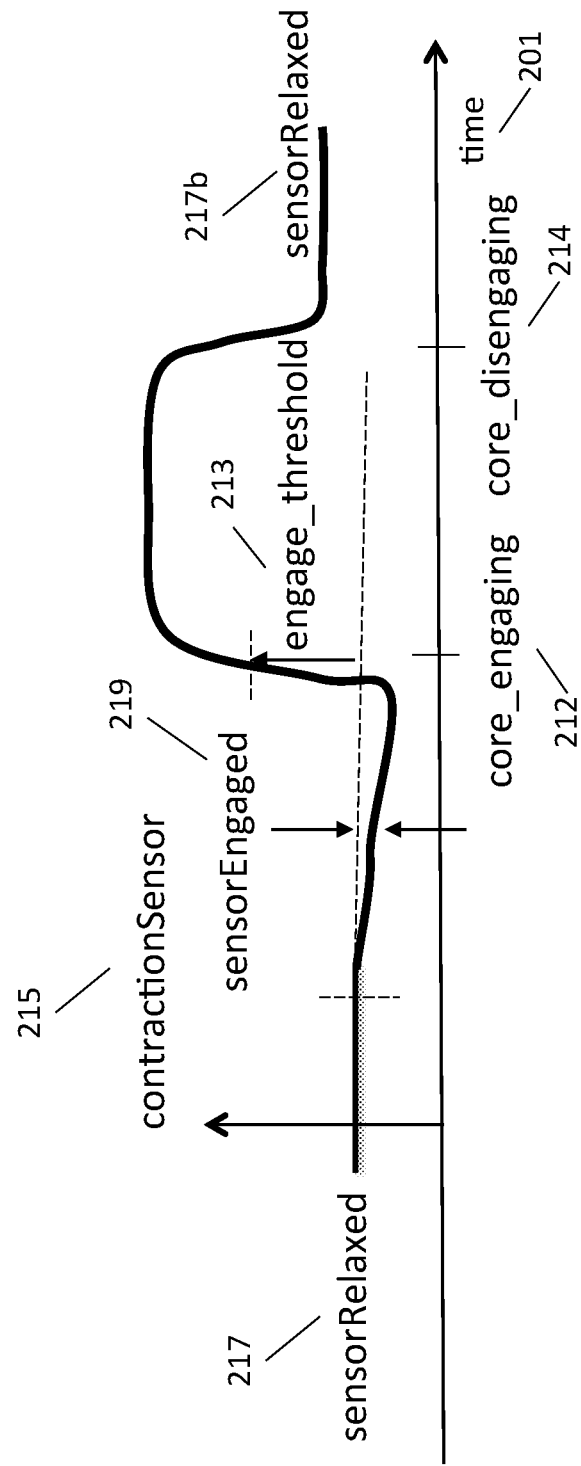
FIG. 24 illustrates features of the signal received from a contraction sensor for identifying a core engagement.

In an embodiment, the core engagement identification algorithm may track a current relaxed value of the core and changes from this value. Referring to FIG. 24, let us refer to the instantaneous value of the contraction sensor value as contractionSensor 215 (vertical Y-axis) plotted as a function of time 201 (horizontal X-axis) starting with the core relaxed. The core contractionSensor 215 then reduces in value prior to increasing during a core engagement. Some users may move their core section such that the pressure on the contraction sensor moves first in the opposite polarity before moving in the polarity of their engaged core, resulting in the contractionSensor 215 shape shown in the figure. This may result from different ways a user may engage his or her core. For example, a user may slightly firm or contract the core muscles, pulling the contraction sensor gently in before firming and pushing slightly outward. This embodiment of core contraction detection processing handles many possible core contraction situation sequences effectively.

Let us refer to the value of contractionSensor 215 when the core is relaxed as sensorRelaxed 217. Let us refer to the deviation of contractionSensor 215 away from sensorRelaxed 217 as sensorEngaged 219. The value of sensorEngaged 219 is referenced to the value of sensorRelaxed 217. In an embodiment, these parameters may be related through the equation:

contractionSensor=sensorRelaxed+sensorEngaged.

When sensorEngaged 219 equals zero, sensorRelaxed 217 equals contractionSensor 215. Finally, engage_threshold 213 may be defined as the threshold for sensorEngaged 219 that when equal to or exceeded, the core is identified as engaged and when not exceeded, the core is identified as relaxed. Since in this embodiment, sensorEngaged 219 is referenced to sensorRelaxed 217 before changes in sensorEngaged 219 occur, it allows different paths or trajectories for sensorEngaged to exceed the engaged_threshold 213.

Figure 25:
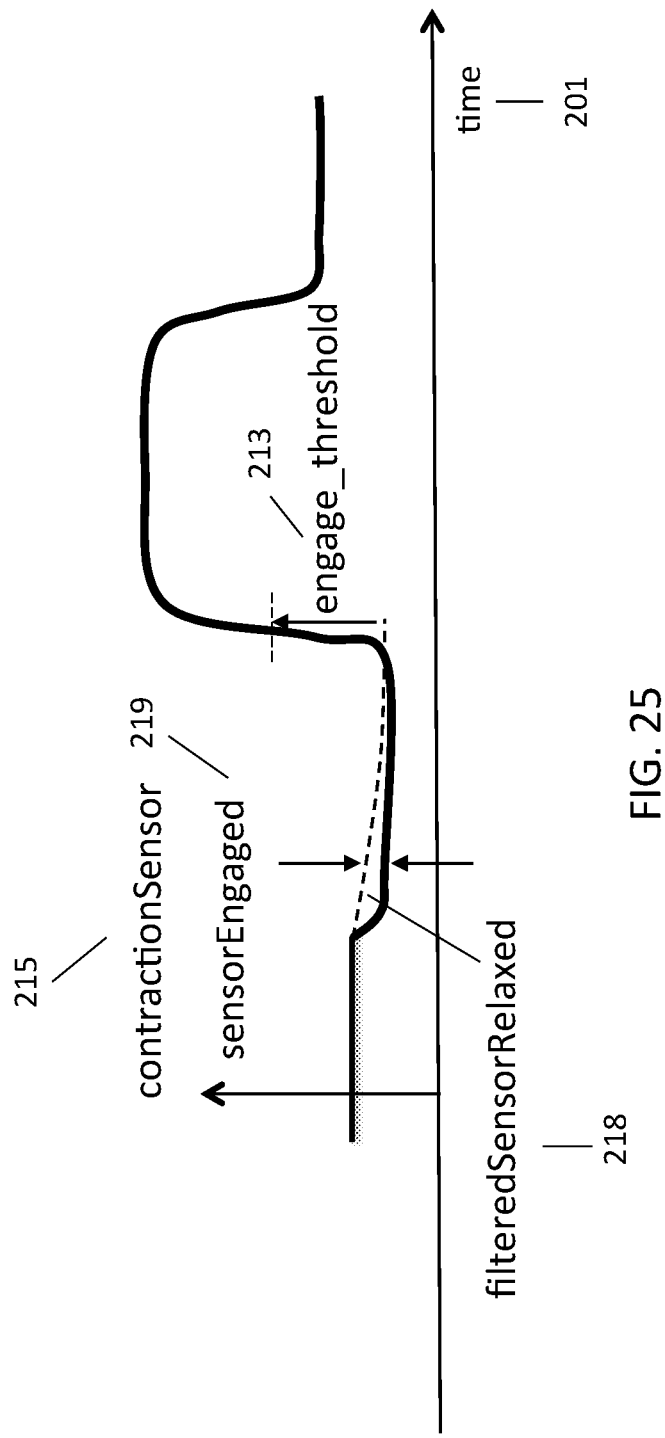
FIG. 25 illustrates filtering the contraction sensor value when the core is relaxed.

Referring to FIG. 25, an embodiment is illustrated where contractionSensor 215 (vertical Y-axis) is plotted as a function of time 201 (horizontal X-axis). During the time the core is identified as relaxed, contractionSensor 215 is passed through a filter. The filter output is filteredRelaxedSensor 218. Parameter engage_threshold 213 is then added to filteredRelaxedSensor 218. When sensorEngaged is equal to or exceeds engage_threshold 213, the core is identified as engaged. In an embodiment, the filter may be implemented as a signal processing block that may include a lowpass filtering to reduce high frequency transients. The signal processing block may include linear or non-linear filtering. Other non-linear signal processing techniques may be utilized.

For some applications, design of the filter may pose a difficult and non-obvious challenge. The wider the filter bandwidth, the better the filter output may track transients due to body movement. But it may also be difficult to differentiate between a movement transient and a valid core engagement. Some users may take longer to engage their core. Some may be fairly quick to engage their core. As mentioned earlier, some may move their core inward before firming. This may reduce the effectiveness of this approach to be effective for a broad range of user variability. In an embodiment, this may be addressed with a programmable or adaptive filter. Later in this description, we will present a different embodiment to address tracking body movements when the core is relaxed.

Using the wearable device described in U.S. patent application Ser. Nos. 14/132,808, 14/789,136, 14/652,542, and 14/817,964 and U.S. Pat. No. 9,226,706, adjustment parameters for the device on a user in an appropriate sensing position include belt adjustment and bumper height. The belt may be adjusted to result in a firm, yet comfortable fit on the user. The bumper height may be adjusted to press through body fat or clothing to the underlying muscle. A user with a higher degree of body fat or a less developed muscle may benefit from a higher bumper height.

It may be beneficial to provide the user with quantifiable measures to help with adjusting both the belt tightness and bumper height. Quantitative measures may be provided to the user through an app running on a smart device via a display or speaker on the smart device. These measures may be provided by the core engagement identification algorithm to aid in the adjustments of both the belt and bumper.

In an embodiment, parameters sensorRelaxed 217 and sensorEngaged 219 from the core engagement identification algorithm may be utilized to aid in belt and bumper adjustment through the app. Parameter sensorRelaxed 217 may be utilized for belt adjustment. A recommended belt adjustment range may be identified by the app and output to the user through the user interface. If sensorRelaxed 217 is less than the lowest value of the belt adjustment range, the recommendation may be to tighten the belt. If sensorRelaxed 217 is above the top of the range, the recommendation may be to loosen the belt. Once sensorRelaxed 217 is in the appropriate range, sensorEngaged 219 may be used to adjust the bumper height. The user may be recommended to place the device over an appropriate area to monitor the core muscles using the smallest available bumper. In the case where a mushroom cap 203 or a similar component is available, it may be used. The user may then engage their core muscles and observe sensorEngaged 219. If sensorEngaged 219 is larger than a target, no changes may be needed to the bumper. If the target cannot be met with a comfortable degree of core contraction, then a bumper extender may be recommended. The user may be informed of multiple alternative locations that may be appropriate for core contraction sensing by the app through a user interface output such as a visual display. Furthermore, the app can also recommend that the user work with a licensed physical therapist or physician, or certified fitness trainer for coaching and guidance. If the bumper height is changed during this fitting procedure, the belt adjustment procedure should be repeated prior to checking the new bumper height.

Let us further examine possible features of the core contraction identification algorithm implementations. A summary of desirable elements and design challenges with implementing a core engagement identification algorithm may include the following:

1. Engage threshold tracks the relaxed core value so the change in pressure on the contraction sensor from an engaged core triggering a positive core engagement identification is relative to the relaxed core value (met using sensorEngaged 219);

2. Engage threshold may be user adjustable or identified via a calibration procedure (met using engaged_threshold 213);

3. When the core is relaxed, the algorithm may get stuck in a condition that even valid core contractions do not move the algorithm to a condition where identifying a core contraction is possible with normal usage; provision is needed to exit this condition using a reset;

4. When the core is relaxed but the algorithm identifies the core as being engaged, the algorithm may get stuck in that condition and not recover with normal usage; provision is needed to exit this condition using a reset;

5. When the device is first placed on a user, the algorithm may get stuck in an undesired state requiring a reset; a button or switch on the wearable to implement the reset may be undesirable; provision is needed to exit this condition using a reset;

6. Efficient way to report sensorRelaxed and sensorEngaged to the user through the app;

7. Desirable to identify core engagement that increases the pressure on the contraction sensor as well as core engagement that decreases the pressure on the contraction sensor (support bracing and hollowing);

8. Desirable to identify when the core is engaged and when it is relaxed to allow duration of a core engagement to be measured;

9. Provision to provide a sound or buzz upon core engagement; the same or another identifiable sound or buzz during the core engagement; and a same or another identifiable sound or buzz during the core disengagement, that is, as the core transitions from the engaged to the relaxed condition;

10. While a user has their core engaged and performs a movement, the movement of the wearable device may result in changes in pressure on the contraction sensor during the movement; these changes in pressure may result in a disengage; and 11. Accommodate various ways a user may transition from a relaxed core to an engaged core.

In an embodiment, the derivative of contractionSensor at time n can be defined as $$derivContractionSensor[n]=contractionSensor[n]-contractionSensor[n-1]$$

If we sum derivContractionSensor[n], we are effectively observing only changes in the contractionSensor from the time index we begin the summation.

In one embodiment, when the core is identified to be relaxed, we may begin the summation, and the result may be sensorEngaged[n] which is sensorEngaged 219 at time index n wherein:

$$sensorEngaged[n] = \sum_{k=Start_{Relaxed}}^{n} derivContractionSensor[k]$$

This implementation of sensorEngaged[n] 219 may have desirable qualities. As described earlier, the sensorRelaxed 217 is removed from the contractionSensor 215 so only changes from sensorRelaxed 217 are tracked. A second desirable quality is that sensorEngaged 219 may be reset back to zero at any time. Therefore, if a change in sensorRelaxed 217 occurs, by starting the summation at the time instant that the new relaxed value is identified, the sensorEngaged 219 may be evaluated relative to this new value of sensorRelaxed 217.

Referring to FIG. 24, we may refer to the time index where sensorEngaged equals or exceeds engage_threshold 213 as core_engaging 212 wherein the user's core is identified as being engaged. Similarly, when the user's core is engaged, we may refer to the time index where sensorEngaged 219 reduces below engage_threshold 213 as core_disengaging 214 wherein the user's core is identified as being relaxed. After sensorEngaged 219 reduces below the engage_threshold 213 the muscle being monitored will reduce in firmness until it reaches the relaxed condition. The result is contractionSensor 215 will decrease and at a time sample, will stop decreasing. Alternatively, contractionSensor 215 may decrease beyond the point that sensorEngaged 219 equals zero and then increase back to a relaxed state sensorRelaxed 217b where this value may be different from sensorRelaxed 217 before the core engagement. In other words, contractionSensor 215 may overshoot sensorRelaxed 217b and bounce back. By monitoring contractionSensor 215, we may identify the core to be relaxed 205 when the current value contractionSensor[n] 215 is greater than or equal to the previous value contractionSensor[n-1] 215.

In an embodiment, after the core muscles are relaxed and the core_disengaging 214, and contrationSensor 215 returns to an identified relaxed value sensorRelaxed 217, we may update the value of sensorRelaxed 217 using the equation:

$$sensorRelaxed=contractionSensor-sensorEngaged.$$

In an embodiment, when the relaxed condition is identified, sensorEngaged 219 may be reset to zero, and sensorRelaxed 217 may be initialized to contractionSensor 215. This may result in sensorRelaxed 217 tracking changes in the relaxed value due to body movements and positioning from before a core engagement to after a core engagement.

In an embodiment, the engage_threshold 213 may be adjustable. The parameter engage_threshold 213 may be adjustable through the app. In an embodiment, an effective value for engage_threshold 213 may be identified via an auto-calibration procedure. The user may select a page in the app for auto-calibration of engage_threshold 213. A button on the GUI for the app may be touched to begin the auto-calibration routine. The user may be advised to begin with the core in the relaxed condition. Then, the app may instruct the user to transition the core to the engaged condition, held in the engaged condition for a specified time interval. For example, two seconds, then transition the core back to the relaxed condition. This sequence of transitioning the core from relaxed to engaged, and back to relaxed may be performed one or more times. If more than one sequence is advised and the core contraction signals during the calibration process can be monitored and observed by the app. With this core contraction calibration information, techniques such as averaging may be utilized. The app may identify a minimum value and a maximum value of contractionSensor 215. The minimum value may be identified as sensorRelaxed 217 and at the maximum value of contractionSensor 215, the difference between contractionSensor 215 and sensorRelaxed 217 may be identified as sensorEngaged 219. A predetermined fraction of sensorEngaged 219 signal value may be identified as engage_threshold 213. For example, in an embodiment fifty percent of sensorEngaged 219 may be identified by the app as the engage_threshold 213. In an embodiment in which multiple sequences are advised, for example, five trial sequences, the average value of multiple engage_thresholds 213 calculated during each core contraction calibration sequence may be stored and utilized by the app to determine the engage_threshold 213. In an embodiment, outlier values may be identified and removed from the evaluation. In an embodiment, if the values do not meet a certain criteria, for example, if the calculated values of engage_threshold 213 are below a minimum value, the user may be advised to repeat the calibration procedure. This process may allow other techniques and methods to be utilized to identify an appropriate value for engage_threshold 213. In an embodiment, the calibration procedure may be utilized to identify a starting value for engage_threshold 213 and the user may then modify this value via the app as part of a fine tuning procedure. Other heuristics may be utilized for different applications to determine the engage_threshold 213.

User experience or the perception a user has about the wearable device and the app is a critical consideration in development of the device, app, and algorithms that operate on the sensor data. It is important that the user perceive that the information being provided from the sensor data is accurate. To this point, it is critical that the algorithms minimize the instances in which the algorithms themselves may modify data as though operating on its own. In an embodiment, if the firmness of the muscles being monitored are not changing, the outputs of the core contraction algorithm should not be changing. However in some instances, it may be acceptable for the algorithm to make changes when the muscles are not changing. These instances may include situations where the algorithm is stuck in a state that normal use is not able to recover from. In an embodiment, when such instances may be identified, automatic or timed resets may be utilized. In these embodiments, calculating sensorEngaged 219 using the numerical summation algorithm by the app is convenient as it allows a reset to be implemented simply by resetting the summer to a known value. In some applications, the reset value may be zero.

As described in the other patent descriptions, the wearable device may be worn on an elastic belt. A user may place the wearable device into position over, for example, a core muscle, and let the elastic belt pull the device toward the body and into place. This may result in the device striking the body with a mild slap and cause a transient step on the contraction sensor. This step may be very large in magnitude and may place the algorithm parameters in relationships to one another or to values that keep normal operation from proceeding. In cases where the relationships of the parameters can be identified in unwanted states, the algorithm may reset sensorEngaged 219. A reset may include setting sensorEngaged 219 to zero and equating sensorRelaxed 217 to contractionSensor 215.

In an embodiment, when a user detects that the algorithm is in a stuck state and the parameters are not as expected, for example if sensorEngaged 219 is not zero when the core is relaxed, a manual reset may be implemented. It may be desirable to use the already available sensors on the device to implement the manual reset instead of requiring the addition of a switch or button. This may be implemented in a number of ways, depending on which sensor is utilized. In an embodiment, the user may firm their core and press and release on the device a number of times. For example, the user may press and release three times in succession. The algorithm may have a section of code designed to observe successively large and small values of contractionSensor 215. When a number, for example, three sets of large and small values are identified within a fixed period of time, for example one second, the app may cause a reset to occur.

When the core is in the relaxed condition and user moves, as described earlier, this may result in changes to sensorRelaxed 217. It may be desirable to have sensorEngaged 219 near a value of zero when the core is relaxed to maintain the required change on the contraction sensor greater than engage_threshold 213 to result in the identification of an engaged core. After a core engagement, sensorRelaxed 217 may settle on a value and sensorEngaged 219 may be equal zero. If the user's body moves, for example, suppose the user is seated and then leans forward, the sensorRelaxed 217 value may stay the same but sensorEngaged 219 may change to a non-zero value. If the user stays in that position, sensorEngaged 219 may maintain the non-zero value. If this condition persists, it may be desirable that the app perform a system reset to return sensorEngaged 219 back to zero. In an embodiment, the algorithm may observe the contractionSensor 215 value and identify when it stays within a range of values, for example, plus or minus one for a time period, for example, two seconds; when both the range and time period requirements are met, a reset may be triggered by the app. Since this reset may occur when the core is relaxed, this reset may be referred to as a Relaxed Reset. Both the range and time period may be fixed, adjustable, or they may be a function of the sensorEngaged 219 value at the start of an evaluated time period. In an embodiment, a lookup table may be used to identify the range and time period to be used for Relaxed Reset as a function of sensorEngaged 219. In an embodiment, Relaxed Reset may be turned on or off through the app and values for range and time period may be adjustable in the app.

When the wearable device is mounted on a user and the user moves or a movement happens such that a core engagement is identified by the algorithm and the user's core is in the relaxed condition, the identification of a core engagement may incorrectly occur and persist indefinitely. In one embodiment, when core_engaging 212 is identified, a timer begins counting. When a time limit is reached, a reset may be triggered by the app. Since this reset occurs when the core is identified to be engaged, this may be referred to as the Engaged Reset. In an embodiment, Engaged Reset may be turned on or off through the app and values for the time limit may be adjustable in the app.

In an embodiment, a settings parameter may be used to select between identifying a core contraction as when sensorEngaged 219 exceeds a positive engage_threshold 213 or when sensorEngaged 219 decreases below a negative value of engage_threshold 213. Exceeding a positive engage_threshold 213 has been called bracing in earlier patent descriptions. Decreasing below a negative engage_threshold 213 has been called hollowing in earlier patent descriptions. The algorithms described in this description are mainly described from the perspective of bracing core engagements. They can easily be modified to support hollowing.

In applications where core engaging 212 and core disengaging 214 are identified by the app which then, provides feedback to the user at the beginning of a core engagement (core engaging 212), at the end of a core engagement (core disengaging 214), and during a core engagement (between core engaging and core disengaging) may be facilitated. In one embodiment, the app and buzzer and sound devices on the wearable may be programmed to provide feedback to the user by identify core engaging 212, core disengaging 214, and core engaged independently with different sounds, buzz patterns, or beep patterns. The feedback signal for each aspect of the core engagement may be turned off and on independently. For example, the user may desire to have only the app provide a beep on core engaging 212 and be silent otherwise. In another instance, the user may desire to have the wearable device provide a single buzz on core engaging 212, and two short buzzes on core disengaging 214. Other combinations of feedback may be used, depending on the preferences of the user.

In an embodiment, a counter may be shown on the app to provide a core contraction and/or timing count. For example, the app may provide a core contraction recording and monitoring in seconds starting on core engaging 212 and ending on core disengaging 214. This may provide a feedback from the app to the user showing how long an individual core engagement may have lasted through a system output such as a GUI. Providing the feedback of the duration of core engagements may be part of a practice routine provided by the app to the user.

As a user performs a dynamic movement such as standing up from a seated position with an engaged core, core_disengaging 214 followed by core_engaging 212 may occur during the movement. The incorrect identification of core_disengaging 214 followed by core_engaging 212 may be confusing or irritating to the user, especially if the user receives two successive core_engaging 212 signals from the app or device when the core was engaged throughout the movement. This transient may occur if the contraction sensor 175 moves away from and back toward the body during the movement, if underlying muscles move during the movement causing a short drop in incident pressure on the contraction sensor 175, or from another short transient causing a short pressure drop. In an embodiment, the body movement sensors may set a body moving flag on a visual display output when the body is identified to be moving in a manner known to create this transient. The body moving flag may be used to inhibit the effect of the core_disengaging 214 signal while the flag is set. This may eliminate the effect of this undesired transient that may occur during a movement like standing up from a seated position.

The body moving flag may be set or body movement may be identified when the output of an accelerometer or gyro signals transmitted to a processor and processed by the app exceeds a predetermined or algorithm calculated threshold value. In some applications, the first or second integral of the accelerometer output or the first integral of the gyro output may be used to minimize false triggers and identify valid movements. In other applications, other signal processing techniques may be used on the movement sensor outputs to identify specific types of body movements.

Many core strengthening exercises, for example, planks, are performed preferably with little or no torso movement. One way a person may perform planks is to lie face down, place each hand thumbs up just under each respective shoulder, with elbows tucked close to the body, then contract the core region and balance on the toes, and elbows and forearms. This position with engaged core muscles may help to develop the core muscles that wrap around the region of the lumbar spine. A person may be encouraged to develop the ability to hold this position for many tens of seconds. Engaged Reset may not be useful in this app because having a time limit of, for example, 30 seconds may make Engaged Reset of little value. In an embodiment, Engaged Movement Reset may be utilized where a reset is triggered when the core is identified to be engaged and a body movement is identified by the movement sensors. Using Engaged Movement Reset, if the algorithm gets stuck in an engaged condition, any appreciable body movement may trigger a reset. In an embodiment, the threshold for identifying a body movement may be adjustable through the app.

In an embodiment, when a button is touched in GUI of the app, a reset may be triggered. In the app, a concise implementation of a reset button, a measure of sensorRelaxed 217, and a measure of sensorEngaged 219 may be desirable as these three items may be present on many pages of the app. Parameters sensorRelaxed 217 can quickly inform a user if the device belt tightness is appropriate, and changes in sensorEngaged 219 when the core is engaged may provide feedback about positioning of the device. A reset button actuation can allow the algorithm to be reset simply with the touch of a button. In FIG. 26a-FIG. 26c, different embodiments of these three items are shown. By placing the items within the area of the button, efficient use of visual space on the app GUI may be achieved. In the embodiment shown in FIG. 26a, a rectangular button 251 is shown. Touching anywhere on the rectangle may trigger a reset. Also shown are numerical values for sensorRelaxed (value "91") 253 and sensorEngaged (value "0") 255. In a second embodiment shown in FIG. 26b, a rectangular button 251 is again shown. In this embodiment, a thick vertical line bar slider 265 is used to represent sensorRelaxed. Two light vertical tick marks 261, 263 are shown. These may represent the boundary for acceptable tightness of the belt. The thick vertical line bar slider 265 represents sensorRelaxed. The thick vertical line bar slider 265 may move to the left as sensorRelaxed 217 decreases and move to the right as sensorRelaxed 217 increases. If sensorRelaxed 217 is outside the range defined by the two light vertical tick marks 261, 263, the user may be advised to adjust the belt tightness. If sensorRelaxed 217 is to the left of the left most light vertical tick mark 261, the user may be advised to tighten the belt. If sensorRelaxed 217 is to the right of the right most light vertical tick mark 263, the user may be advised to loosen the belt. The number "0" 255 may represent sensorEngaged 219. In another embodiment, the reset button is round as shown in FIG. 26c and FIG. 26d. Touching the circle 251 will trigger a reset. As the core is engaged, in one embodiment, the radius of the circle may increase and the color 267 may change as indicated by the dotted pattern. One or both of these changes to the circle may be used to illustrate the identification of an engaged core through the GUI to the user. The sensorRelaxed 217 value is again shown on the slider 265 similar to the configuration of FIG. 26b.

In an embodiment, sensorRelaxed 217 and sensorEngaged 219 may be presented to the user in the app as a color or gray shade changes of an element, on sliders, as numbers, element size changes, or may use another visual, audible, or other tactile means of providing feedback. These embodiments illustrate inventive presentations of some of the critical parameters from monitoring the core that may be used to provide feedback to the user. Additional parameters may be added to similar features for different applications.

Figure 27:
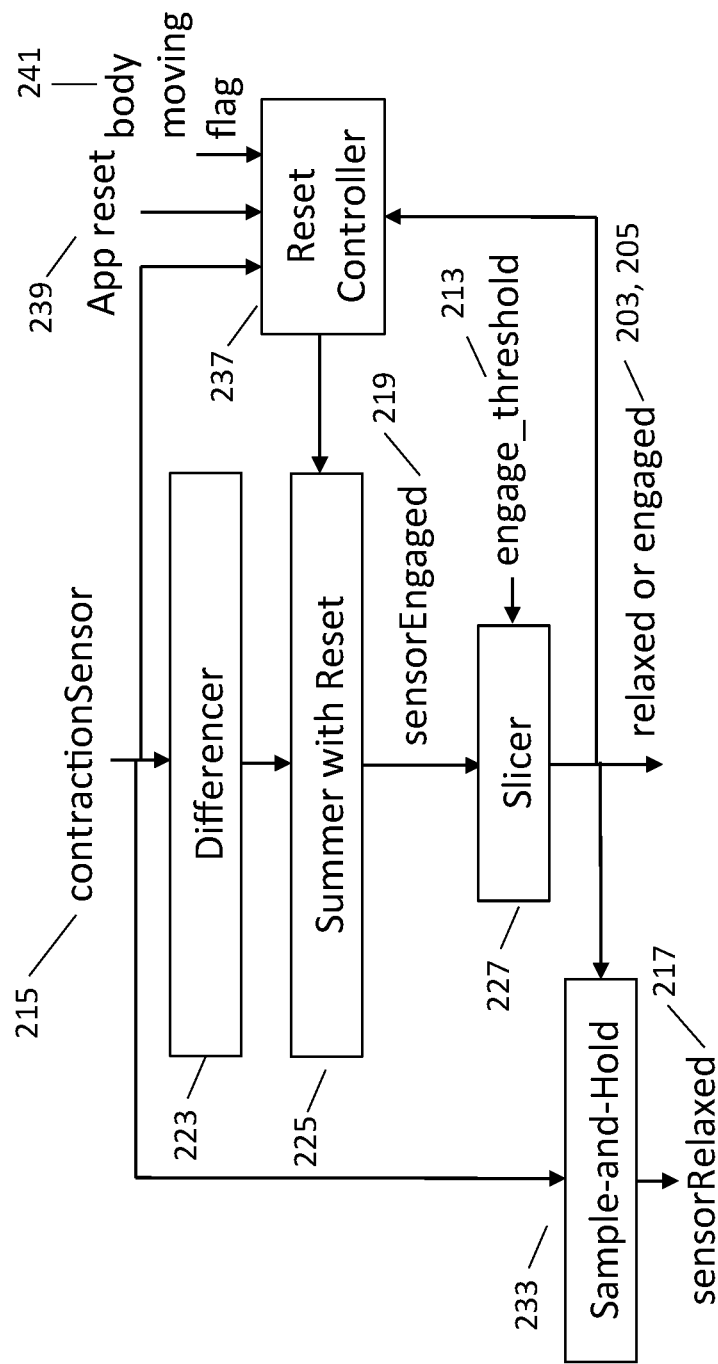
FIG. 27 illustrates a signal flow graph for the core engagement identification algorithm.

A signal flow diagram for an embodiment of the core contraction algorithm is shown in FIG. 27. Data from the contraction sensor contractionSensor 215 is the input. The system may be configured so that when the pressure increases on the contraction sensor, contractionSensor 215 increases.

The Differencer 223 block generates the difference between the current contractionSensor[n] and the contractionSensor[n−1]. The difference samples are input to the Summer 225 block. The output of the Summer 225 block is sensorEngaged 219. The Summer 225 may be reset by the output of Reset Controller 237. When sensorEngaged 219 passes through the engage_threshold 213, Slicer 227 identifies core_engaging and the core is identified as engaged. From the engaged condition, when sensorEngaged 219 goes negative and passes through the engage_threshold 213, core_disengaging is identified and the core is identified as relaxed. When the core first returns to relaxed, sensorEngaged 219 is reset to zero and the value of contractionSensor 215 is sampled and held by the Sample-and-Hold 233 block. The output of the Sample-and-Hold block 233 is sensorRelaxed 217.

There can be a number of inputs to the Reset Controller 237. The input data contractionSensor 215 is input directly and may trigger a reset when in one embodiment, the user engages the core and presses and releases quickly three times. This is one of many ways, the user may perform a manual reset. The app may have a button displayed on a GUI that when touched may trigger a reset. The relaxed 203 or engaged 205 condition may be an input to the Reset Controller 237. When in the relaxed 203 condition, a Relaxed Reset may be selected to occur. A Relaxed Reset may be triggered when the core is in the relaxed condition and contractionSensor 215 stays within predetermined value limits for a predetermined time period, both of which may be user specified through an input to the app. When in the engaged 205 condition, an Engaged Reset may be selected to occur. An Engaged Reset may be triggered after the core is engaged 205 for a time limit, which may be user specified. In an embodiment, both the Relaxed Reset and the Engaged Reset may be turned on or off via the GUI of the app. In an embodiment, when the body is identified to be moving via the movements sensor and movement sensor algorithm, a body moving flag 241 may be set and core_disengaging may be muted until the body moving flag is reset. This may be used to keep the core_engaging signal from signaling twice during a single movement such as standing up from a seated position.

The signal flow diagram in FIG. 27 is merely an example of an embodiment of a signal flow diagram utilizing the inventive concepts presented in this description.

In an embodiment, functional modes may be defined. Functional modes may be distinguished by a number or name. When a functional mode is selected, preset programmable configurations of the core contraction algorithm may be selected. In an embodiment, modes are numbered. In this embodiment, in Mode 1, Relaxed Reset and Engaged Reset may be turned off. Use of the body moving flag 241 may also be turned off. In Mode 2, both Relaxed Reset and Engaged Reset may be turned on and the timers may each be set for 2 seconds. Use of the body moving flag 241 may be turned off during Mode 2. In Mode 3, the Reset conditions of Mode 2 may be turned on, and use of the body moving flag 241 may also be turned on. Functional modes may make it simpler for the user to change programmable parameters based on specific use models. Settings may be selected to provide the user with an appropriate selection of parameters for specific activities. In an embodiment, the user may be allowed to modify parameters after a mode is selected.

In an embodiment, sensorRelaxed 217 may be presented to the user as a color or gray shade, or on a slider on a visual display of a GUI of the app, or using another visual, audible, or other tactile means of providing feedback. In an embodiment, sensorEngaged 219 may be presented to the user as a number, or on a slider, or changing the radius of a circle, or may use color or gray shade on an illustration, or use another visual, audible, or other tactile means of providing feedback.

Figure 28:
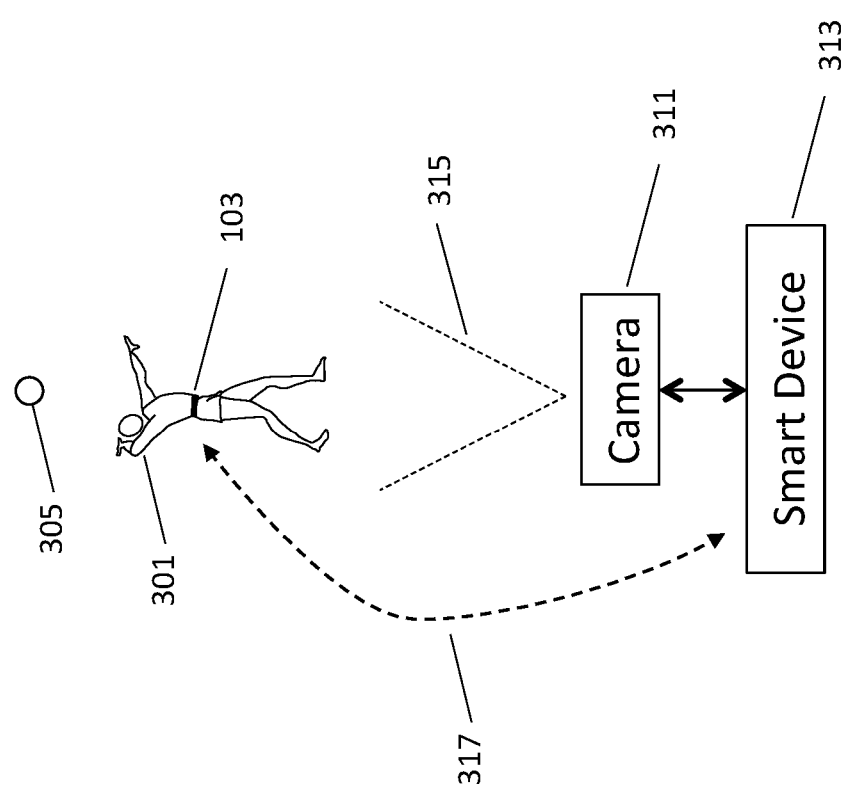
FIG. 28 illustrates the system including the wearable device on a volleyball player, camera, and smart device.

The wearable device may connect to a smart mobile computing device such as a smart phone, smart pad, PC, or dedicated device running an app. The app may run on the iOS or Android operating system, or it may run on a proprietary operating system. The app may be used to control the parameters of the wearable device and receive data and provide feedback from the device to the user. With reference to FIG. 28, an athlete 301 may wear wearable device 103. Camera 311 may be situated to place athlete 301 in camera view 315 to record movements of the athlete 301 throughout the substantial part or all of an athletic movement. In the example shown, the athlete 301 may be serving a volleyball 305. The camera 311 may be situated in close proximity to or part of the smart device 313. Wearable device 103 and smart device 313 may be connected via a wireless communication link 317. In this scenario, the wearable device 103 may be in proximity to the smart device 313 to maintain a constant communication link 317 throughout the athletic movement.

Figure 29:
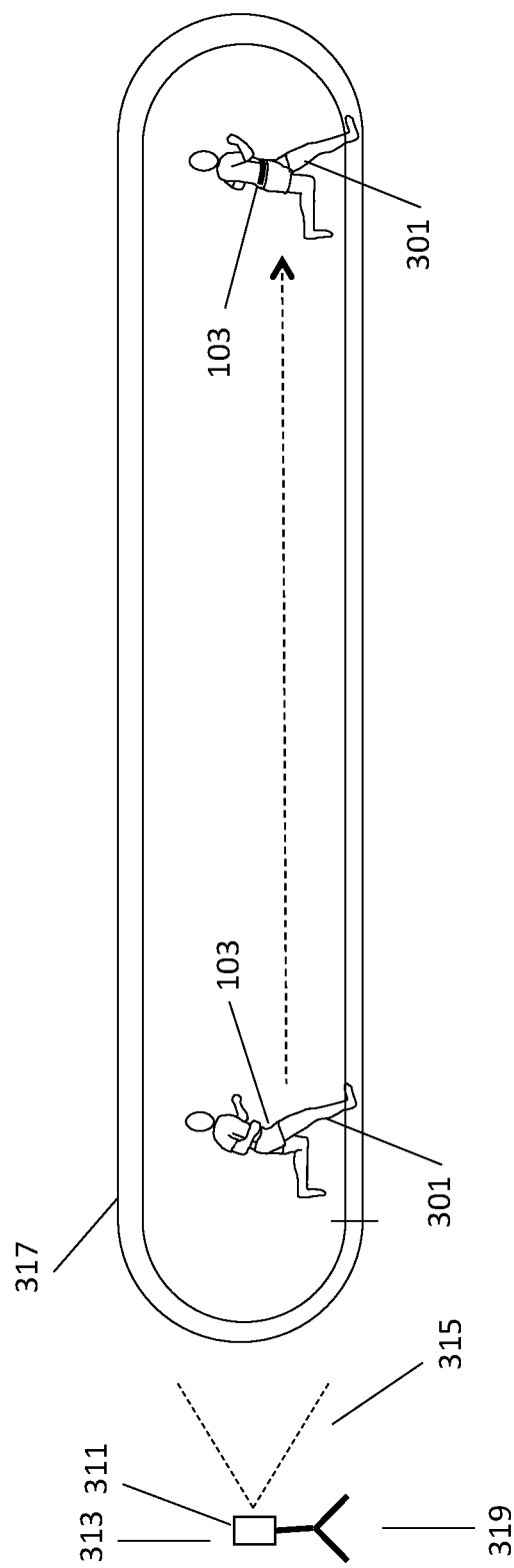
FIG. 29 illustrates the system being used on a runner on a track where the wearable device is on the runner, and the camera and smart device are located on one end of the track.

Another scenario is illustrated in FIG. 29 where runner 301 wearing wearable device 103 is running around a track 317. Camera 311 and smart device 313 are situated on one end of the track. Camera 311 is placed on tripod 319. The runner 301 may be placed in the camera view 315 for at least a portion of the athletic event which in this case is a run around a portion of all of the track. In this scenario, wearable device 103 may not maintain constant communication with the smart device 313. The wearable device 103 and smart device 313 may have communication before the start of the event and again at the end of the event when the two devices are again in close proximity.

Figure 30:
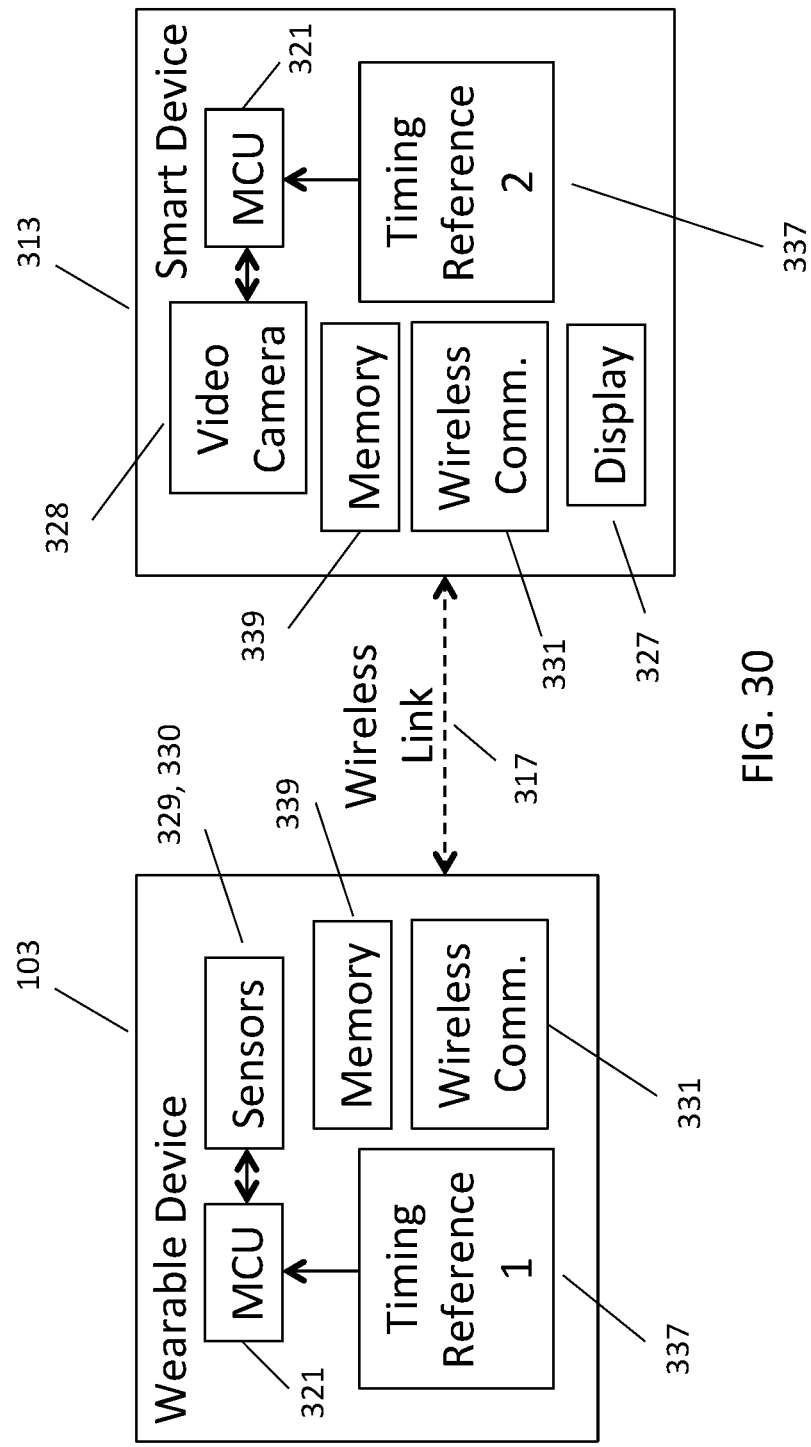
FIG. 30 illustrate a block diagram of an embodiment including a wearable device and a smart device connected via a wireless link where the camera is included in the smart device.

Referring to FIG. 30, simplified block diagrams of the wearable device 103 and smart device 313 are shown with critical blocks that support recording or storing of data including memory 339, timing references 337 which define sampling instants when the data is stored, communication link 331, microcontrollers MCU 321, sensors 329, 330 on the wearable 103, video camera 328 and display 327 on the smart device 313.

Figure 31:
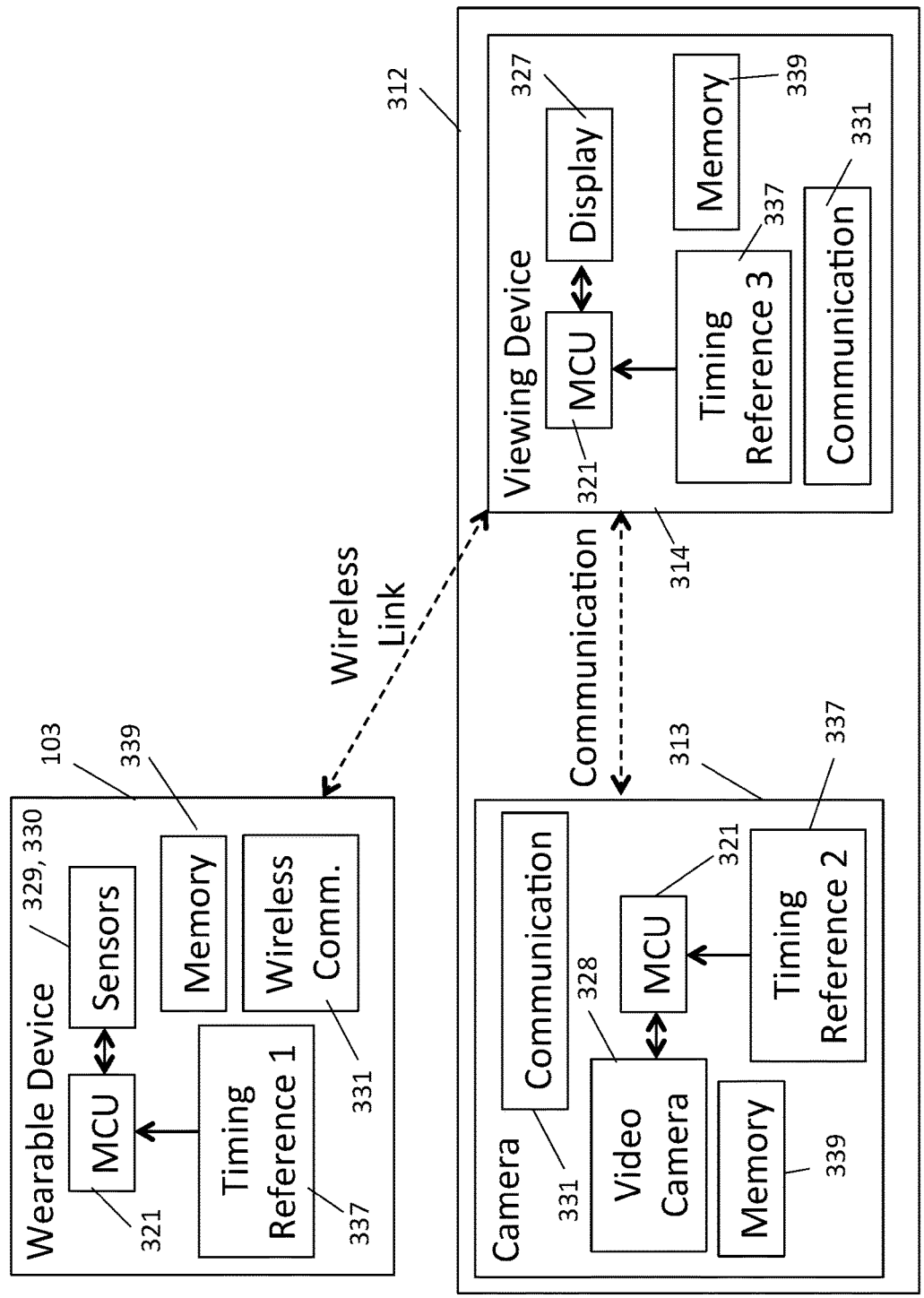
FIG. 31 illustrates a block diagram of an embodiment including a wearable device, a camera, and a viewing device where the smart device connects to the viewing device via a wireless link and the camera connects to the viewing device via a communications link which may be a wireless link or a wired link.

Referring to FIG. 31, simplified block diagrams for the scenario where the wearable device 103 is used in a system with a video camera 313 and a viewing device 314. A viewing device 314 will have a display 327 and may have an MCU 321, timing reference 3 337, communication link 331, and memory 339. Camera 313 will have video camera 328, communication link 331, memory 339, timing reference 2 337, and MCU 321.

The viewing device 314 and the camera 313 can be separate and distinct components. However, in an alternative embodiment, the viewing device 314 and the camera 313 can both be components of a single smart device 312. For low-cost and convenient to use implementations a smart device 312 containing both the camera 313 and display 314 are is attractive. This integrated combination with video camera 313 and display 314 will be used in the discussion that follows.

During playback, data from the sensors and video data may be played back simultaneously, to view the coordination of core or muscle contraction with other body movements. An important challenge that must be addressed is implementing the system to ensure that when sensor data is presented, the video frames that are displayed were taken at substantially the same instants. Different applications and different levels of athletic performance may dictate the need for higher sample rates which also may require better time alignment of sensor samples and video frame data. For example, for therapeutic applications, sample rates as low as 6 Hz may be acceptable. Whereas for athletic applications, sample rates of 30 Hz may be desirable. In some applications, rates of 60 Hz or higher may be desirable. As sample rates increase, it may be desirable to maintain time alignment between the sensor data and the video frame data to be on the order of the reciprocal of the sample rate.

There are two functions required in this processing flow: 1. Data acquisition and storage; 2. Processing to ensure time coordination of playback samples. At a high level, there are two scenarios to consider. The first is where the wearable device 103 and smart device 313 are in constant communication. In this scenario, the wearable device may stream data from the sensors 329, 330 and signal processing algorithms to the smart device 313. Assuming the latency from the sensor sample on the wearable 103 to the memory 339 of the smart device 313 is low, for example, on the order of the reciprocal of the sample rate, since the data is arriving to the smart device memory 339 with the video data, there is essentially a single timing reference Timing Reference 2 337 in FIG. 30 writing data samples to memory. Since a single timing reference is used, time stamps for sensor data and video frames are essentially the same since they come from the same timing source 337.

In the second scenario, the wearable 103 may be near the smart device 313 only at the start and end of the movement, for example, when the athlete takes a lap around a track. When devices are outside the range that communication is possible, the wearable device will rely on Timing Reference 1 337 for time-stamping sensor data samples and storing to its memory 339. Using the scenario of FIG. 30 for illustration, the smart device 313 includes the video camera 328 and uses Timing Reference 2 337 for time-stamping video frames as they are stored to memory 339. When the frequencies between Timing Reference 1 and Timing Reference 2 are different, and sensor data samples 393 and video frame samples 391 may continue to accumulate timing offset during playback, frequency difference correction may be used. In one embodiment of frequency difference correction, one of the devices, the first device provides a timing reference signal based on the timing reference 337 of the first device to the other, the second device to allow the second device to calculate any frequency difference between the timing reference 337 of the second device and the timing reference 337 of the first device. In an embodiment, the timing reference is a tone or continuous-wave signal. The frequency difference between the timing references 337 may then be accounted for during the playback of the sensor data and video frames. In most applications, the timing accuracy requirement may be on the order of the reciprocal of the minimum sample rate required to provide useful information to the user. In some applications, signal processing techniques such as interpolation and decimation may be used. In some applications, the frequency difference between timing references 337 may be resolved by eliminating data or repeated data intermittently when phase error accumulation due to the difference in timing references 337 accumulates beyond a threshold.

Consider another embodiment of frequency difference correction through the following example. Consider the scenario where the smart device 313 timing reference 337 is used during playback and the timing reference 337 of the smart device 313 is one percent slower than the wearable device 103. Consider further the scenario where the wearable device 103 is separated from the smart device 313 during the athletic event so that the sensor data samples are sent over the communication link 331 after recording of the event has stopped. When the data from the wearable device 103 played back on the smart device 313 with video frames sampled using the timing reference 337 of the smart device, if the timing reference 337 of the smart device is one percent slower than the timing reference 337 of the wearable device 103 and assuming the sample rates are the same, the algorithm may throw out one sample set of data from the wearable device every 101 samples of data from the wearable device 103.

In some applications, the sample rate used for sensor data may be different than the sample rate used for video frames. Appropriate signal processing methods may be used to resolve any systematic differences in sample rates. In some cases, similar techniques may be used to resolve sample rate difference as are used to resolve timing reference 337 frequency differences.

Figure 32:
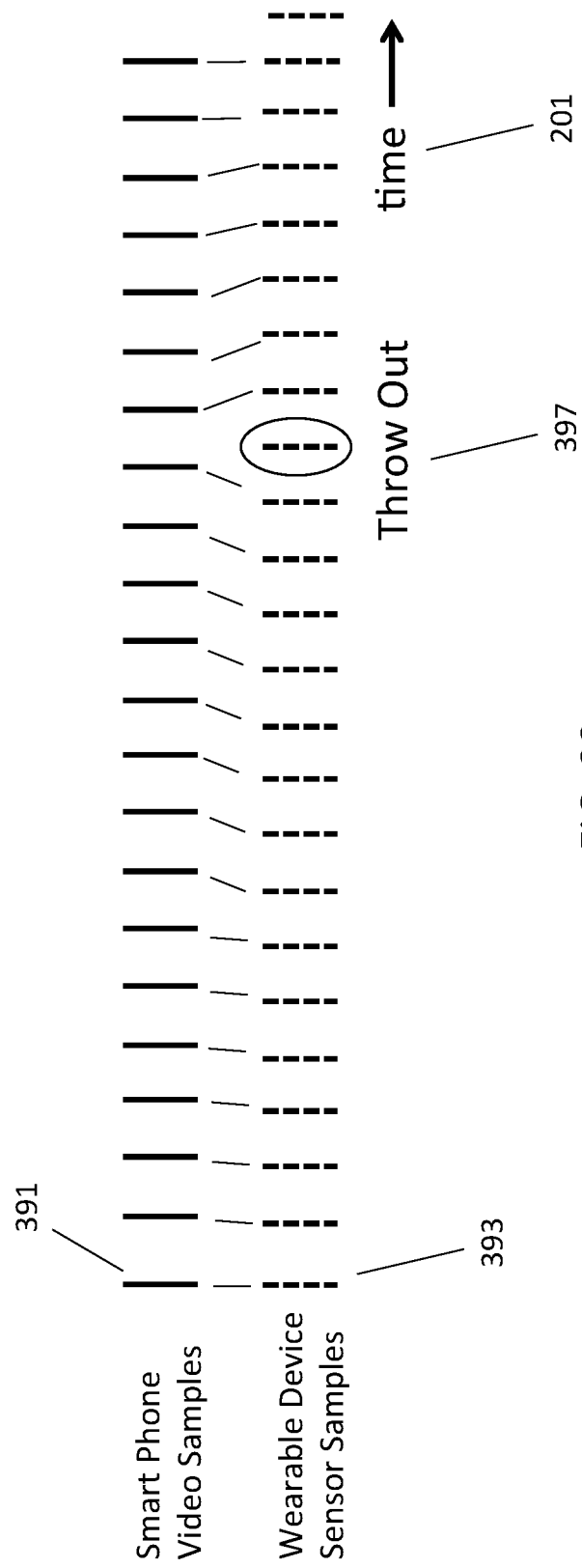
FIG. 32 illustrates sample instants for smart phone video samples and wearable device sensor samples are shown over time.

With reference to FIG. 32, sample instants for smart phone video samples 391 and wearable device sensor samples 393 are shown over time 201 (horizontal X-axis). Due to the wearable device timing reference being at a higher frequency than the smart device timing reference, after several samples are output the smart phone video samples 391 will be out of synchronization with the wearable device sensor samples 393 and there is an extra sample of sensor samples 393. The algorithm may choose one of the wearable device sensor samples 393 and throw it out or not use it. For example, the wearable device sensor sample 397 may be thrown out to result in the same number of samples of sensor samples 393 and video samples 391.

With reference to FIG. 31, there are a number of ways to implement the system to accommodate the scenario where the wearable device 103 and smart device 313 lose the communication link during the recorded event or movement. In one embodiment, at the start of recording, the smart device 313 sends a start signal command to the wearable device 103. At the same time, smart device 313 may start a first timer counter. Upon receiving the strobe, wearable device 103 may start recording sensor data and also may start a second timer counter. Both devices may store time-stamp or SMPTE data along with sensor data samples 393 and video frame samples 391 (Shown in FIG. 32). At the end of the recording, the smart device 313 may send out a stop signal command to the wearable device 103 and may stop the first timer counter. Upon receiving the stop signal command, the wearable device 103 may stop recording data and may stop the second timer counter. The wearable device 103 may then send recorded data associated with samples taken during the recording period, time-stamp or SMPTE data may also be sent to the smart device 313. In addition, the wearable device 103 may send the ending second timer counter value to the smart device 313. The algorithm controlling playback may use the difference between the ending first time counter and ending second timer counter values to determine if any frequency difference correction is required. If the frequency difference is determined to be small considering the length of the recording, no frequency difference correction may be applied. If the frequency difference and length of recording result in frequency difference correction being applied, then the technique described for frequency difference correction, or a similar technique, or an equivalent technique may be utilized.

Figure 33:
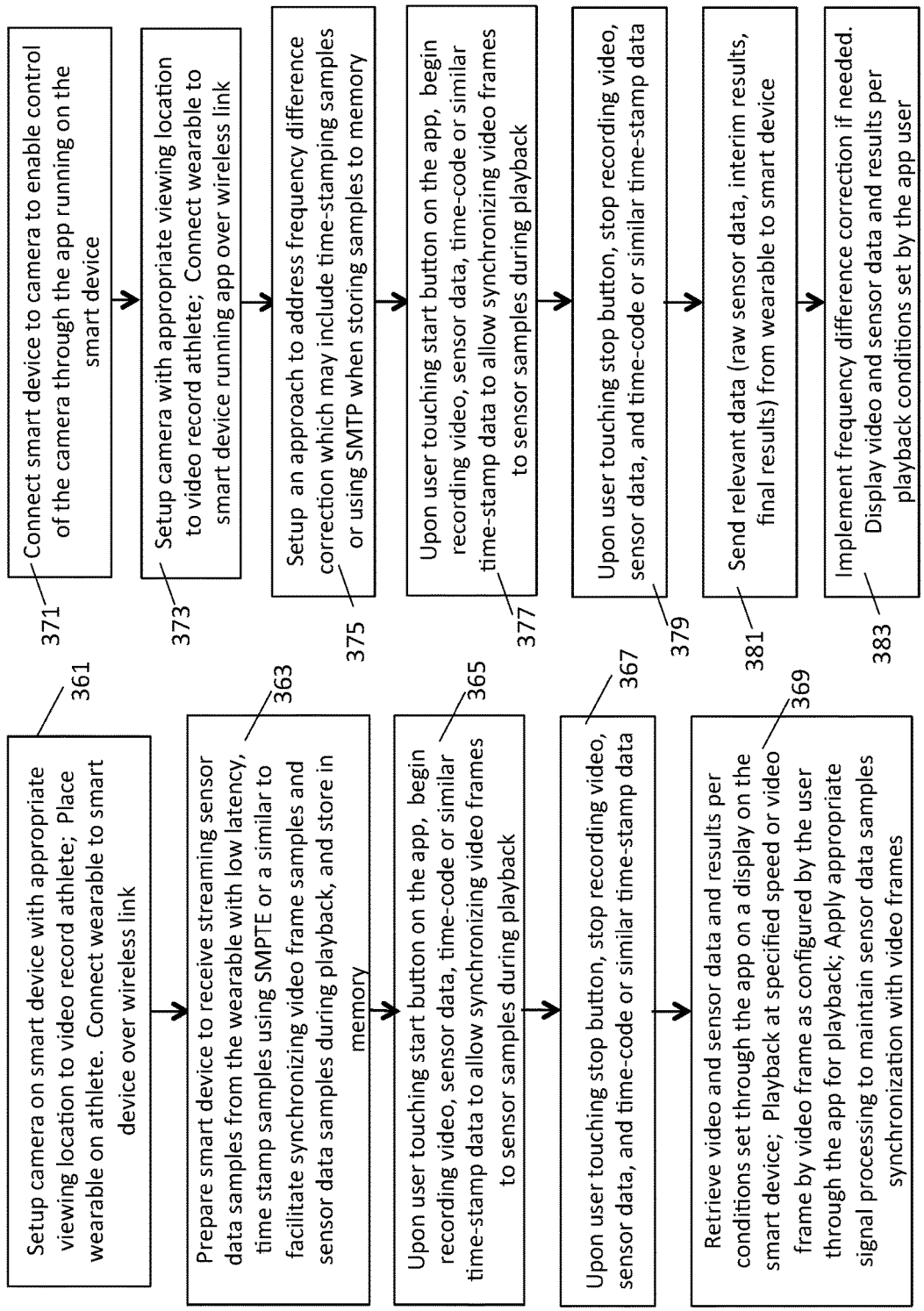
FIG. 33a illustrates a flow diagram for a scenario where the wearable device and smart device are in communication throughout the recorded movement duration.
FIG. 33b illustrates a flow diagram for a scenario where the wearable device and smart device are not in communication throughout the recorded movement duration.

A flow diagram for an embodiment of the system where the wearable device 103 and smart device 313 are connected over a communication link or wireless link throughout the duration of a movement is shown in FIG. 33a. Begin with system setup 361 by placing the camera in a location to view the athlete during the event or movement, place the wearable device 103 on the athlete, and connect the wearable device to the smart device 313 over a communication link which may be a wireless link. The smart device 313 may be prepared to receive streaming data from the wearable device 363. When the user touches a start button or equivalent on the app, begin recording video, sensor data, and time-stamp data 365. When the user touches the stop button or equivalent on the app, stop recording video, sensor data, and time-stamp data 367. Retrieve video and sensor data and results can be performed per conditions set by the user through the app on a display on the smart device 369. Playback of the data can be at a specified speed, for example in slow motion, or video frame by video frame as configured by the user through the app. Appropriate signal processing can be applied by the system to maintain sensor data samples synchronization with video frames.

A flow diagram for an embodiment of the system where the wearable device 103 and smart device 313 may not be connected over a communication link or wireless link throughout the duration of a movement or athletic event such as a running event is shown in FIG. 33b. In an embodiment, the wearable device stores data during the movement in a memory on the wearable device and transfers this data to the smart device after the end of the movement. The wearable device 103 and smart device 313 may have communication at the start and end of the movement or athletic event. Begin with system setup 371 by connecting the camera to the smart device. In an embodiment, the camera on the smart device is utilized. Next, place the camera in a location to view the athlete during the event or movement, place the wearable device 103 on the athlete, and connect the wearable device to the smart device 313 over a communication link which may be a wireless link 373. Setup an approach to address frequency difference correction which may include time-stamping samples or using SMTP when storing samples to memory 375. When the user touches a start button or equivalent on the app, begin recording video, sensor data, and time-stamp data 377. When the user touches the stop button or equivalent on the app, stop recording video, sensor data, and time-stamp data 379. Send relevant data (raw sensor data, interim results, final results) from the wearable device to the smart device 381. Implement frequency difference correction if needed. Display video and sensor data and results per playback conditions set by the app user 383.

Figure 34:
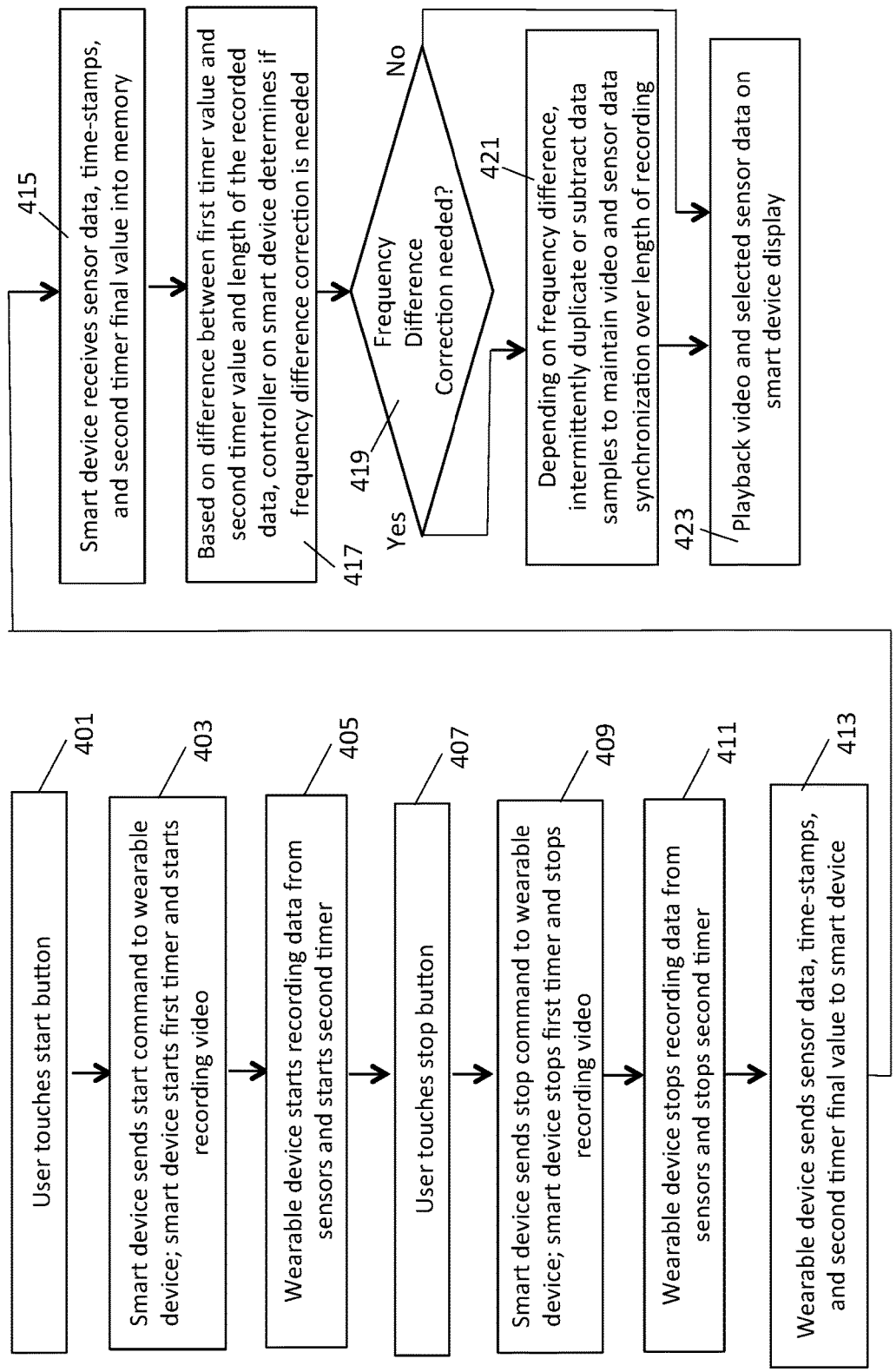
FIG. 34 illustrates a flow diagram for an embodiment of frequency difference correction.

A flow diagram for an embodiment of the frequency difference correction algorithm is shown in FIG. 34. Begin when the user touches a start button or similar in the app 401. Smart device may send a start command to the wearable device. The smart device may then start a first timer and may start recording video 403. Wearable device starts recording data from the sensors and starts a second timer 405. User touches stop button or equivalent 407. Smart device sends stop command to wearable device. Smart device stops first timer and stops recording video 409. Wearable device stops recording data from the sensors and stops second timer 411. Wearable device sends sensor data, time-stamps, and second timer final value to smart device 413. Smart device receives sensor data, time-stamps, and second timer final value into memory 415. Based on difference between first timer value and second timer value and length of the recorded data, controller on smart device may use a look-up table to determine if frequency difference correction is needed 417. If 419 frequency difference correction is not needed, proceed ahead to 423. If 419 frequency difference correction is needed, proceed to 421. Depending on frequency difference, intermittently duplicate data samples or subtract data samples to maintain video and sensor data synchronzation over length of the recording 421. Playback video and selected sensor data on smart device display 423.

Figure 35:
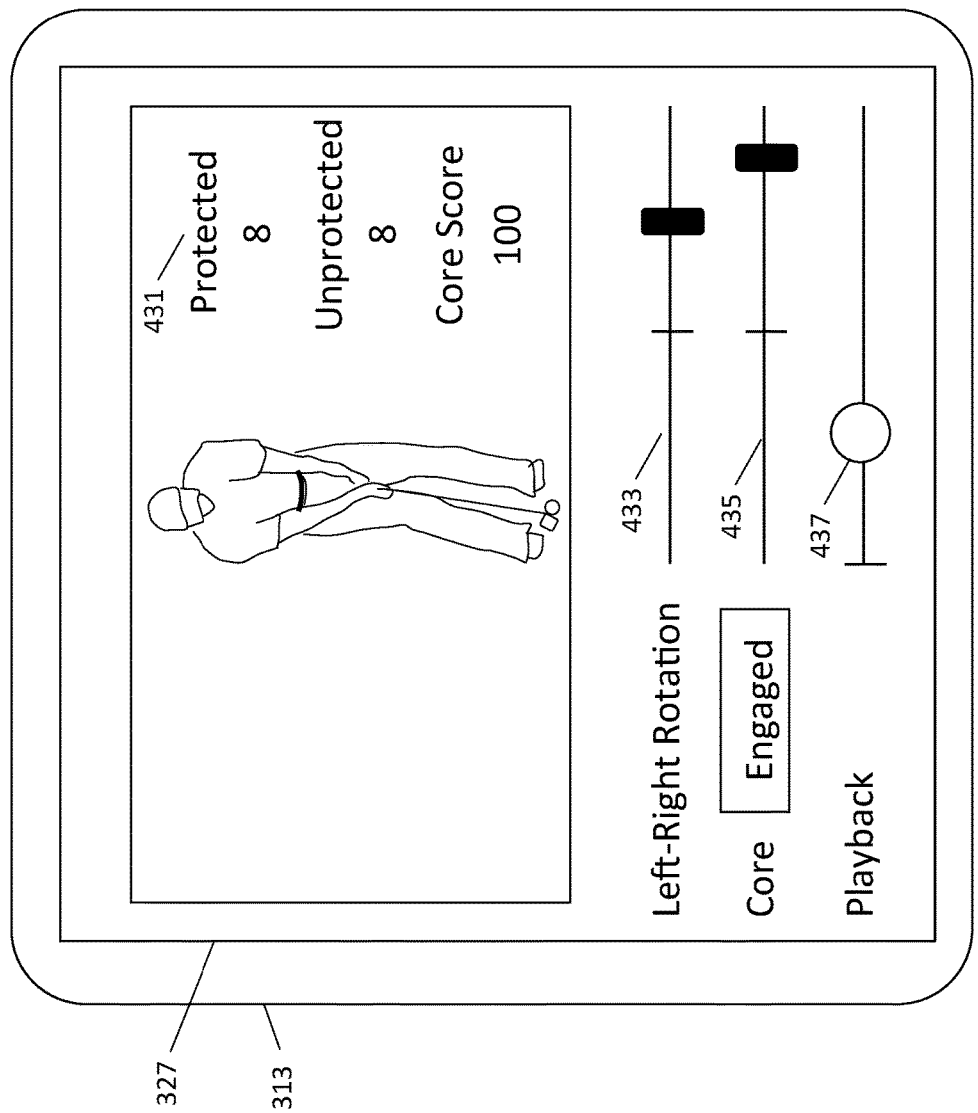
FIG. 35 illustrates a smart device display playback view including video of the user, sensor data, and a playback control slider.

An embodiment of a smart device 313 display 317 showing a video playback of the athlete 327, a display of a core engagement sensor 435, a display of a movement sensor 433, and a playback control slider 437 is illustrated in FIG. 35. The core score showing the number of protected and unprotected movements for a number of athletic movements is illustrated in the upper right corner 431. Protected movements may include in this example, golf swings in which the core is engaged prior to and through the hip turn of the golf swing. The identification of an engaged core may be shown associated with the display of the core engagement sensor 435. During playback, the user may place a finger on the playback control slider 437 and slide to the left or right. As the user slides to the right, the app may step progressively through the video recording and sensor data to show the timing of the movement proportional to the speed that the user slides the slider to the right. Sliding the playback control slider 437 to the left may result in the video recording and sensor data to be shown in reverse. In an embodiment, different data may be selected via the app for playback. For example, instead of left-right rotation, up-down movement or movement left-right may be selected.

In some applications, the user may record a number of similar movements in succession. For example, the user may desire to record 10 successive golf chip shots. Instead of run the recorder for the entire duration of the 10 chip shots and the time in between, it may be desirable to record only the data associated from the start to end of each shot. In an embodiment, the system may use data from the core sensor and movement sensor to determine moments of pause by the athlete, and the start of movements and end of movements by the athlete. These pauses and identified movement starts and movement ends may be used to determine the start and stop times for recording the sensor and video data. In an embodiment, if the duration between a start and stop is less than a minimum duration, the recording may be discarded. In an embodiment, if no movement is detected by the movement sensors, the recording may be discarded. In another embodiment, if a core contraction is not identified during the movement, the recording may be discarded.

In many applications, for maximum benefit and performance, body positioning, posture, rotation and orientation may be performed with engaging the core. Good posture generally positions the spine to minimize stress on the spine. The contracted core then further benefits the spine by providing support around a well positioned spine. The combination of posture and body positioning together with a well-timed core contraction may be desirable objectives for movements in athletics, training, and rehab. The preferred execution of a movement is generally comprised of a sequence of shorter movements, each executed in a preferred manner. When the execution of a movement takes on an undesirable trajectory, a compensatory movement is often needed to get the movement back on the track of a preferred movement. In many applications, the undesirable trajectory results in inefficiency in the movement, which may degrade performance. The position of the upper body in relation to the lower body during a movement may be critical to maintain balance throughout the movement. The identification of jerky movements with the movement sensor may be useful to help identify compensatory movements during a movement so that the action causing the compensatory movement may be identified, minimized, or eliminated. In some applications, recording video, core contraction data, and movement data may be used after a successful movement has been performed to view and analyze the timing of the elements of the movement to provide the athlete and coach information to improve consistency and performance. In such an instance, the system may help identify the preferred timing of certain movements and timing of a core contraction for preferred execution of a movement.

In a volleyball float serve, the orientation of the torso or body position is predominantly upright and movement of the torso is predominantly forward, with minimal hip rotation prior to and during the ball strike. Excessive hip rotation or body rotation may affect the direction of the serve and may cause forward energy during the body weight shift in the direction of the serve to be lost. This may be an example in which body positioning and rotation with the core contraction may be parameters of the movement that may be desirable for an athlete and coach to track and display.

The inventive system can monitor the core contraction and compare the core contraction to the body position for specific athletic movements. The user can then review the video footage, body position and core contraction. For example, in a preferred method of kicking a soccer ball, in preparation for the kick, the athlete may plant the foot opposite the kicking foot down on the ground near the side of the ball as the athlete prepares to pull the kicking foot forward to kick though the ball. The athlete may contract the core just before the opposite foot strikes the ground and throughout the forward movement of the kick in order to support the lumbar spine and help control body movement during the kick.

By viewing the video playback with body position and core contraction information, the user can learn the timing of the core contraction and the body position for specific athletic actions. The position and rotation of the user's body can be detected by body position sensors such as accelerometers and/or gyroscopes in a wearable device as described above Body positions and body postures for which support from contraction of the core muscles may be beneficial to the lumbosacral junction and lumbar spine can be known as Qualifying Positions or Qualifying Postures (QP). When a QP is identified, the system can determine whether or not the Qualifying Position and/or Qualifying Posture is protected or not protected based on the status of the user's core before, during, and after the QP. The system can provide information to the user about when to contract their core muscles during the time the stress on the lumbar spine and lumbosacral junction is greatest during a QP through the video playback. By learning the proper times to contract the core muscles during QPs, the user develop the habit of contracting their core muscles during QPs such that they may continue this beneficial practice even without the system. In general, if the core is contracted before and during the QP, the QP may be considered a protected QP. In contrast, if the core is not contracted during the QP, this can be known as an unprotected QP.

Some user movements are body rotations that can be detected by the wearable device sensors. A Qualifying Rotation (QR) is a body rotation for which support from contraction of the core muscles may be beneficial to the lumbosacral junction and lumbar spine. When a QR is identified, the system determines whether or not the QR is protected or not protected based on the status of the user's core before, during, and after the QR. Objectives of the system include: having the user contract their core muscles during the time the stress on the lumbar spine and lumbosacral junction is greatest during a QR; and having the user develop the habit of contracting their core muscles during QRs such that they continue this beneficial practice even without the system. In general, if the core is contracted before and during the QR, the QRmay be considered a protected QR and if the core is not contracted during the QR, this can be known as an unprotected QR.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Some embodiments of the invention are implemented as a program product for use with an embedded processor. The program(s) of the program product defines functions of the embodiments (including the methods described herein) and can be contained on a variety of signal-bearing media. Illustrative signal-bearing media include, but are not limited to: (i) information permanently stored on non-writable storage media; (ii) alterable information stored on writable storage media; and (iii) information conveyed to a computer by a communications medium, such as through a computer or telephone network, including wireless communications. The latter embodiment specifically includes information downloaded from the Internet and other networks. Such signal-bearing media, when carrying computer-readable instructions that direct the functions of the present invention, represent embodiments of the present invention.

In general, the routines executed to implement the embodiments of the invention, may be part of an operating system or a specific application, component, program, module, object, or sequence of instructions. The computer program of the present invention typically is comprised of a multitude of instructions that will be translated by the native computer into a machine-accessible format and hence executable instructions. Also, programs are comprised of variables and data structures that either reside locally to the program or are found in memory or on storage devices. In addition, various programs described hereinafter may be identified based upon the application for which they are implemented in a specific embodiment of the invention. However, it should be appreciated that any particular program nomenclature that follows is used merely for convenience, and thus the invention should not be limited to use solely in any specific application identified and/or implied by such nomenclature.

The present invention and some of its advantages have been described in detail for some embodiments. It should be understood that although the process is described with reference to a device, system, and method for developing core contraction procedural memory, the process may be used in other contexts as well. It should also be understood that various changes, substitutions and alterations can be made herein without departing from the spirit and scope of the invention as defined by the appended claims. An embodiment of the invention may achieve multiple objectives, but not every embodiment falling within the scope of the attached claims will achieve every objective. Moreover, the scope of the present application is not intended to be limited to the particular embodiments of the process, machine, manufacture, composition of matter, means, methods and steps described in the specification. A person having ordinary skill in the art will readily appreciate from the disclosure of the present invention that processes, machines, manufacture, compositions of matter, means, methods, or steps, presently existing or later to be developed are equivalent to, and fall within the scope of, what is claimed. Accordingly, the appended claims are intended to include within their scope such processes, machines, manufacture, compositions of matter, means, methods, or steps.

What is claimed is:

1. A method for improving the timing of a core engagement with a body movement to improve performance, comprising:
  providing a contraction sensor, a movement sensor, a video camera, and a display in communication with a processor and a memory coupled to the processor, wherein the contraction sensor having a bumper core sensor interface extending from the contraction sensor;
  placing the bumper core sensor interface of the contraction sensor against core muscles of a user;
  detecting core contractions of the user with the contraction sensor;
  detecting body movements of the user with the movement sensor;
  recording the body movements of the user with the video camera;
  transmitting core contraction signals from the contraction sensor to the processor;
  determining by the processor a contraction status of the core muscles that is either contracted when the core contraction signal is greater than a threshold value or relaxed when the core contraction signal is less than the threshold value;

transmitting body movement signals from the movement sensor to the processor;
transmitting video signals from the video camera to the processor;
storing the core contraction signals, the body movement signals and the video signals in the memory;
determining by the processor timing relationships between the core contraction signals and the body movement signals;
immediately outputting by the processor the video signals and the timing relationships of the core contraction signals and the body movement signals to the display; and
simultaneously displaying on a visual display a user movement from the video signals and the contraction status of the core muscles for the user movement.

2. The method of claim 1 wherein the video signals are displayed on the display in slow motion.

3. The method of claim 1 wherein the display is a touch screen and a playback speed of the video signals is controlled by a slider control on the display.

4. The method of claim 3 wherein the slider may be controlled by a finger in contact with the slider control on the display.

5. The method of claim 1 wherein the recording of the body movements of the user starts after the processor receives the body movement signals which include a first body movement signal following a first pause in movement and a first core contraction signal for a minimum predetermined period of time; and the recording of the body movements ends after the processor detects a second pause in movement and core contraction following a movement where one or both of a movement or core contraction is detected by the processor.

6. The method of claim 5 wherein a minimum duration between the pause before and pause following a movement is detected in order to keep the recorded data.

7. The method of claim 1 wherein the core contraction signals are received by the processor in real time from the contraction sensor and the movement signals are received by the processor in real time from the movement sensor, and the video camera, the display, the processor, and the memory are located on a smart device, and the core contraction signals, the movement signals, and the video signals are simultaneously stored in the memory and time stamps are applied to cumulative data groups wherein each of the cumulative data groups includes include some of the core contraction signals, the movement signals, and the video signals.

8. The method of claim 1 wherein the core contraction signals and the movement signals are stored in a first memory and the video signals are stored in a second memory, and wherein the core contraction signals, the movement signals and the video signals are combined prior to the outputting of the core contraction signals, the movement signals and the video signals by the processor.

9. A method for development of core muscles based support, comprising:
providing a contraction sensor and a movement sensor in communication with a first processor coupled to a first memory on a first device, wherein the contraction sensor having a bumper core sensor interface extending from the contraction sensor;
placing the bumper core sensor interface of the contraction sensor against core muscles of a user;
providing a video camera in communication with a second processor coupled to a second memory on a second device;
providing a display;
detecting core contractions of the user with the contraction sensor;
detecting body movements of the user with the movement sensor;
recording the body movements of the user with the video camera;
transmitting core contraction signals from the contraction sensor to the first processor;
determining by the first processor a contraction status of the core muscles that is either contracted when the core contraction signal is greater than a threshold value or relaxed when the core contraction signal is less than the threshold value;
transmitting body movement signals from the movement sensor to the first processor;
storing the core contraction signals and the body movement signals sent to the first processor in the first memory;
transmitting video signals of the body movements of the user from the video camera to the second processor;
storing video signals of the body movements of the user in the second memory; and
immediately outputting the core contraction signals and the movement signals from the first memory and some of the video signals from the second memory to the display to illustrate timing relationships of the core contractions and the body movements wherein an image of the user movement from the video signals and the contraction status of the core muscles for the image of the user movement are displayed simultaneously.

10. The method of claim 9 wherein time stamps are applied to the core contraction signals, the movement signals, and the video signals and the time stamps are used to synchronize the core contraction signals, the movement signals, and the video signals before the outputting of the core contraction signals, the movement signals and the video signals.

11. The method of claim 9 further comprising:
providing a user interface and a touchscreen that is part of the display;
wherein the user interface includes a slider shown on the display and the playback is controlled by the slider.

12. The method of claim 9 wherein the core contraction signals, the movement signals and the video signals are combined as a plurality of data groups and the plurality of data groups are stored in the first memory or the second memory and each of the plurality of data groups are labeled.

13. The method of claim 12 further comprising:
displaying a listing of the plurality of data groups on the display;
selecting one of the plurality of the plurality of data groups; and
playing the one of the plurality of the plurality of data groups.

14. The method of claim 9 wherein the display is part of the video camera.

15. The method of claim 9 further comprising:
detecting body orientations of the user with the movement sensor;
transmitting body orientation signals from the movement sensor to the first processor; and
storing the body orientation signals in the first memory.

16. The method of claim 15 further comprising:
outputting the body orientation signals from the first memory to the display to illustrate timing relationships between the core contractions and the body orientations.

17. The method of claim 9 further comprising:
detecting body postures of the user with the movement sensor;
transmitting body posture signals from the movement sensor to the first processor; and
storing the body posture signals in the first memory.

18. The method of claim 17 further comprising:
outputting the body posture signals from the first memory to the display to illustrate timing relationships between the core contractions and the body postures.

19. The method of claim 9 further comprising:
detecting body rotation of the user with the movement sensor;
transmitting body rotation signals from the movement sensor to the first processor; and
storing the body rotation signals in the first memory.

20. The method of claim 19 further comprising:
outputting the body rotation signals from the first memory to the display to illustrate timing relationships between the core contractions and the body rotations.

* * * * *